(12) United States Patent
Vraspir et al.

(10) Patent No.: US 9,394,266 B2
(45) Date of Patent: Jul. 19, 2016

(54) SOLID STATE FORMS OF CABAZITAXEL AND PROCESSES FOR PREPARATION THEREOF

(71) Applicant: IVAX International GmbH, Rapperswil-Jona (CH)

(72) Inventors: Pavel Vraspir, Rymarov (CZ); Alexandr Jegorov, Dobra Voda (CZ); Roman Gabriel, Olomouc (CZ); Ales Gavenda, Ostrava-Ihotka (CZ)

(73) Assignee: Ivax International GmBh, Rapperswil (CH)

( * ) Notice: Subject to any disclaimer, the term of this patent is extended or adjusted under 35 U.S.C. 154(b) by 42 days.

(21) Appl. No.: 14/382,958

(22) PCT Filed: Mar. 7, 2013

(86) PCT No.: PCT/US2013/029664
§ 371 (c)(1),
(2) Date: Sep. 4, 2014

(87) PCT Pub. No.: WO2013/134534
PCT Pub. Date: Sep. 12, 2013

(65) Prior Publication Data
US 2015/0038564 A1    Feb. 5, 2015

Related U.S. Application Data

(60) Provisional application No. 61/608,471, filed on Mar. 8, 2012, provisional application No. 61/650,197, filed on May 22, 2012.

(51) Int. Cl.
*C07D 305/14* (2006.01)

(52) U.S. Cl.
CPC ........... *C07D 305/14* (2013.01); *C07B 2200/13* (2013.01)

(58) Field of Classification Search
CPC ........................... C07D 305/14; C07B 200/13
USPC .................................................... 549/510, 511
See application file for complete search history.

(56) References Cited

U.S. PATENT DOCUMENTS

| 5,847,170 | A | 12/1998 | Bouchard et al. |
| 7,241,907 | B2 | 7/2007 | Didier et al. |

FOREIGN PATENT DOCUMENTS

| CN | 102503913 | 6/2012 | |
| CN | 102675257 | 9/2012 | |
| CN | 102746258 | 10/2012 | |
| CN | 102898406 | 1/2013 | |
| CN | 103058960 | 4/2013 | |
| WO | WO 2005/028462 A1 | 3/2005 | |
| WO | WO 2009/115655 A2 | 9/2009 | |
| WO | WO 2012/142117 A1 | 10/2012 | |
| WO | WO 2013/034979 A2 | 3/2013 | |
| WO | WO 2013/080217 A1 | 6/2013 | |
| WO | WO 2013/088335 | * 6/2013 | ........... C07D 305/14 |
| WO | WO 2013/088335 A1 | 6/2013 | |

OTHER PUBLICATIONS

Sriram et al "Process for Preparing Crystalline Cabazitaxel and it's Solvents", 2012, 3 pgs.

* cited by examiner

*Primary Examiner* — Erich A Leeser
(74) *Attorney, Agent, or Firm* — Baker & Hostetler LLP

(57) ABSTRACT

The invention relates to solid state forms of Cabazitaxel and processes for preparing the solid state forms. The invention further relates to pharmaceutical compositions and formulations comprising one or more of the solid state forms.

33 Claims, 54 Drawing Sheets

SOLID STATE FORMS OF CABAZITAXEL AND PROCESSES FOR PREPARATION THEREOF

CROSS-REFERENCE TO RELATED APPLICATIONS

This application is the National Stage of International Application No. PCT/US2013/029664, filed Mar. 7, 2013, which claims the benefit of U.S. application No. 61/608,471, filed Mar. 8, 2012, and U.S. application No. 61/650,197, filed May 22, 2012, the disclosures of which are incorporated herein by reference in their entirety.

FIELD OF THE INVENTION

The present invention relates to solid state forms of Cabazitaxel, processes for preparing the solid state forms as well as pharmaceutical compositions and formulations comprising one or more of the solid state forms.

BACKGROUND OF THE INVENTION

Cabazitaxel, (αR,βS)-α-hydroxy-β-[[(1,1-dimethylethoxy) carbonyl]amino]benzene-propanoic acid (2aR,4S,4aS,6R,9S,11S,12S,12aR,12bS)-12b-(acetyloxy)-12-(benzoyloxy)-2a,3,4,4a,5,6,9,10,11,12,12a,12b-dodecahydro-11-hydroxy-4,6-dimethoxy-4a,8,13,13-tetramethyl-5-oxo-7,11-methano-1H-cyclodeca[3,4]benz[1,2-b]oxet-9-yl ester, has the following chemical structure:

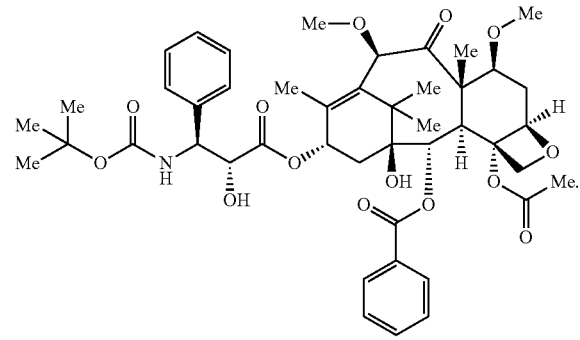 [SMILES: CO[C@H]1C(=O)[C@]2(C)[C@@H](OC)C[C@H]3OC[C@@]3(OC(C)=O)[C@H]2[C@H](OC(=O)c2ccccc2)[C@]2(O)C[C@H](OC(=O)[C@H](O)[C@@H](NC(=O)OC(C)(C)C)c3ccccc3)C(C)=C1C2(C)C]

Cabazitaxel is a semi-synthetic taxoid derivative. It is marketed under the trade name JEVTANA® for the treatment of hormone-refractory prostate cancer.

Cabazitaxel and a process for its preparation are disclosed in U.S. Pat. No. 5,847,170. Cabazitaxel acetone solvate is disclosed in U.S. Pat. No. 7,241,907. Several solid state forms of Cabazitaxel are furthermore disclosed in WO2009/115655 and in WO2012/142117.

Polymorphism, the occurrence of different crystal forms, is a property of some molecules and molecular complexes. A single molecule, like Cabazitaxel, may give rise to a variety of polymorphs having distinct crystal structures and physical properties like melting point, thermal behaviors (e.g. measured by thermogravimetric analysis—"TGA", or differential scanning calorimetry—"DSC"), powder X-ray diffraction (PXRD) pattern, infrared absorption fingerprint, and solid state NMR spectrum. One or more of these techniques may be used to characterize a particular polymorph and to distinguish different polymorphic forms of a compound.

Different solid state forms (including solvated forms) of an active pharmaceutical ingredient may possess different properties. Such variations in the properties of different solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different solid state forms may also offer improvements to the final dosage form, for instance, if they serve to improve bioavailability. Different solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new polymorphic forms and solvates of a pharmaceutical product can provide materials having, inter alia, desirable processing properties, such as ease of handling, ease of processing, chemical and polymorphic stability upon storage and processing, and ease of purification or are useful as advantageous intermediate crystal forms that facilitate conversion to other solid state forms (including other solvates) of said pharmaceutical product. New polymorphic forms and solvates of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, or improved shelf-life. Lastly, new polymorphic forms may be prepared with improved reliability and reproducibility compared to other forms, for example in terms of crystallinity or polymorphic purity.

SUMMARY OF THE INVENTION

The present invention provides solid state forms of Cabazitaxel, processes for preparing these solid state forms, pharmaceutical compositions and formulations comprising one or more of the solid state forms of Cabazitaxel, and processes for the preparation thereof.

The present invention also provides the use of said solid state forms of Cabazitaxel the manufacture of pharmaceutical compositions and formulations. The present invention thus further provides a pharmaceutical composition comprising one or more of the solid state forms of Cabazitaxel of the present invention. This pharmaceutical composition may additionally comprise at least one pharmaceutically acceptable excipient, thereby forming a pharmaceutical formulation that can, for example, be administered to patients in need of such treatment.

The present invention comprises a process for preparing the above-mentioned pharmaceutical compositions. The process comprises combining the solid state forms of Cabazitaxel with at least one pharmaceutically acceptable excipient.

The solid state forms as defined herein as well as the pharmaceutical compositions of Cabazitaxel can be used as medicaments, particularly for the treatment of prostate cancer, particularly hormone-refractory prostate cancer. The present invention also provides a method of treating hormone-refractory prostate cancer comprising administering a therapeutically effective amount of the solid state forms of Cabazitaxel of the present invention, or a therapeutically effective amount of at least one of the pharmaceutical compositions of the present invention comprising one or more of the solid state forms of Cabazitaxel of the present invention to a patient in need thereof.

The present invention also provides the use of the solid state forms of Cabazitaxel of the present invention, or at least one of the above pharmaceutical compositions for the manufacture of a medicament for treating of prostate cancer, particularly hormone-refractory prostate cancer.

DETAILED DESCRIPTION OF THE INVENTION

Figure 1:
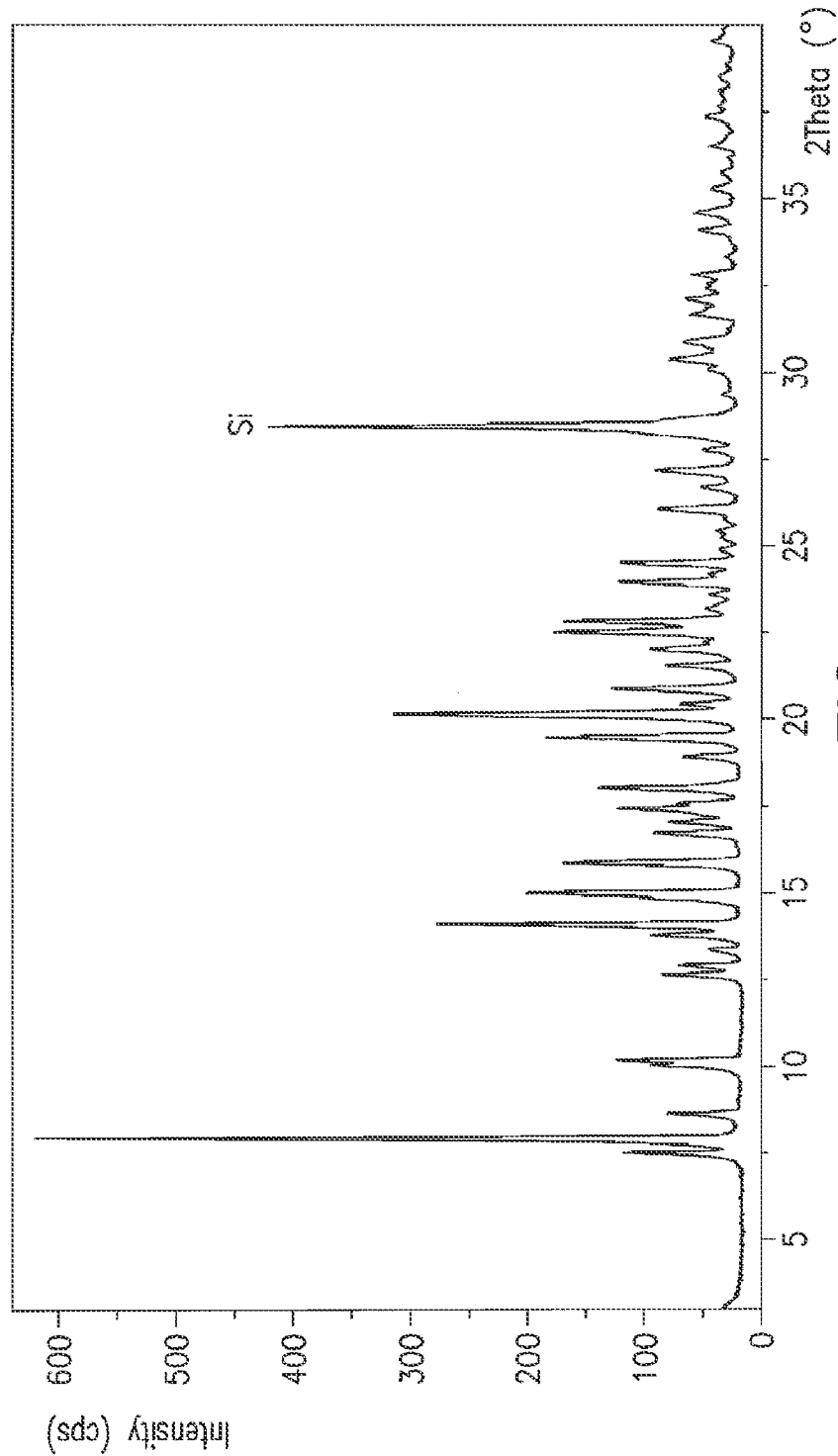
FIG. 1 shows a PXRD pattern for crystalline Cabazitaxel form VII.

The present invention provides solid state forms of Cabazitaxel, processes for preparing the solid state forms, as well as pharmaceutical compositions comprising one or more of the solid state forms.

Depending on which other solid state form they are compared with, the solid state forms of the present invention may have advantageous properties selected from at least one of: chemical or polymorphic purity, increased crystallinity, flowability, solubility, dissolution rate, bioavailability, morphology or crystal habit, specific surface and pycnometric density, bulk/tap density, stability—such as chemical stability as well as thermal and mechanical stability with respect to polymorphic conversion, stability towards dehydration and/ or storage stability, a lower degree of hygroscopicity, low content of residual solvents and advantageous processing and handling characteristics such as compressibility, and bulk density.

Solid state forms of Cabazitaxel comprise crystal forms, or crystalline forms, of Cabazitaxel. As used herein, solid state forms, crystal forms, crystalline forms, polymorphs and polymorphic forms are used interchangeably.

A crystal form may be referred to herein as being characterized by graphical data "substantially as depicted in" a Figure. Such data include, for example, powder X-ray diffractograms and solid state NMR spectra. The graphical data potentially provides additional technical information to further define the respective solid state form which can not necessarily or easily be described by reference to numerical values for peak positions and/or relative intensities. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

As used herein, the expression "chemical shift difference" refers to the difference in chemical shifts between a reference signal and another signal in the same NMR spectrum. These chemical shift differences serve to provide an additional analytical measurement for a substance, for example a Cabazitaxel crystal form of the present invention, which will compensate for a phenomenon that may occur in NMR spectroscopy wherein a shift in the solid-state NMR "fingerprint" is observed. Such a shift in the NMR peaks may occur, for example as a result of variations in the instrumentation, the temperature, or the calibration method used in the NMR analysis. This shift in the solid-state NMR "fingerprint", having chemical shift resonances at a certain positions, is such that even though the individual chemical shifts of signals have moved, all the peaks in the spectrum are moved be the same amount, such that the difference between chemical shifts of each signal and another is retained. Thus, this shift may be used as a reliable characterization of the material being analyzed.

In the present patent application the chemical shift differences were calculated by subtracting the chemical shift value of the signal exhibiting the lowest chemical shift (reference signal) in the solid state $^{13}C$ NMR spectrum in the range of 0 to 180 ppm from chemical shift value of another (observed) signal in the same $^{13}C$ NMR spectrum in the range of 100 to 180 ppm.

A crystal form (or polymorph) may be referred to herein as substantially free of any other crystalline (or polymorphic) forms. As used herein in this context, the expression "substantially free of any other forms" will be understood to mean that the crystalline form contains 20% or less, 10% or less, 5% or less, 2% or less, or 1% or less of any other forms of the subject compound as measured, for example, by PXRD. Thus, polymorphs of Cabazitaxel described herein as substantially free of any other polymorphic forms would be understood to contain greater than 80% (w/w), greater than 90% (w/w), greater than 95% (w/w), greater than 98% (w/w), or greater than 99% (w/w) of the subject polymorphic form of Cabazitaxel. Accordingly, in some embodiments of the invention, the described polymorphs of Cabazitaxel may contain from 1% to 20% (w/w), from 5% to 20% (w/w), or from 5% to 10% (w/w) of one or more other crystal forms of Cabazitaxel.

As used herein, the expression "room temperature" refers to a temperature between about 20° C. and about 30° C. Usually, room temperature ranges from about 20° C. to about 25° C.

As used herein, the term "overnight" refers to a period of between about 15 and about 20 hours, typically between about 16 to about 20 hours.

As used herein, the expression "wet crystalline form" refers to a polymorph that was not dried using any conventional techniques to remove residual solvent. Such conventional techniques include, but are not limited to, evaporation, vacuum drying, oven drying, drying under nitrogen flow etc.

As used herein, the expression "dry crystalline form" refers to a polymorph that was dried using any conventional techniques to remove residual solvent. Such conventional techniques include, but are not limited to, evaporation, vacuum drying, oven drying, drying under nitrogen flow, etc.

As used herein, and unless stated otherwise, the term "anhydrous" in relation to crystalline Cabazitaxel relates to a crystalline Cabazitaxel which contains not more than 1% (w/w) of either water or organic solvents as measured by TGA. An anhydrous form of the solid states of Cabazitaxel of the present invention refers to a form that does not contain crystalline water (or other solvents) in a defined, stoichiometric amount within the crystal.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, and unless stated otherwise, the terms "powder" or "powdery" refer to a solid compound in the forms of particles or granules, wherein the particles or granules can be poured. Preferably, the powders are solid, loose and dry particles.

As used herein, and unless indicated otherwise, the term "polymorphic stability" in relation to the crystalline forms of Cabazitaxel means that there is less than 20%, 10%, 5%, 1%, 0.5% or 0.1% conversion of crystalline Cabazitaxel to any other solid state form of Cabazitaxel under the specified conditions, as measured by PXRD. In some embodiments, the conversion is 0.5%-20%, 0.5%-10% or 0.5%-5% or 0.5%-1% or 0.1%-1%, or 0.1%-0.5%.

Figure 31:
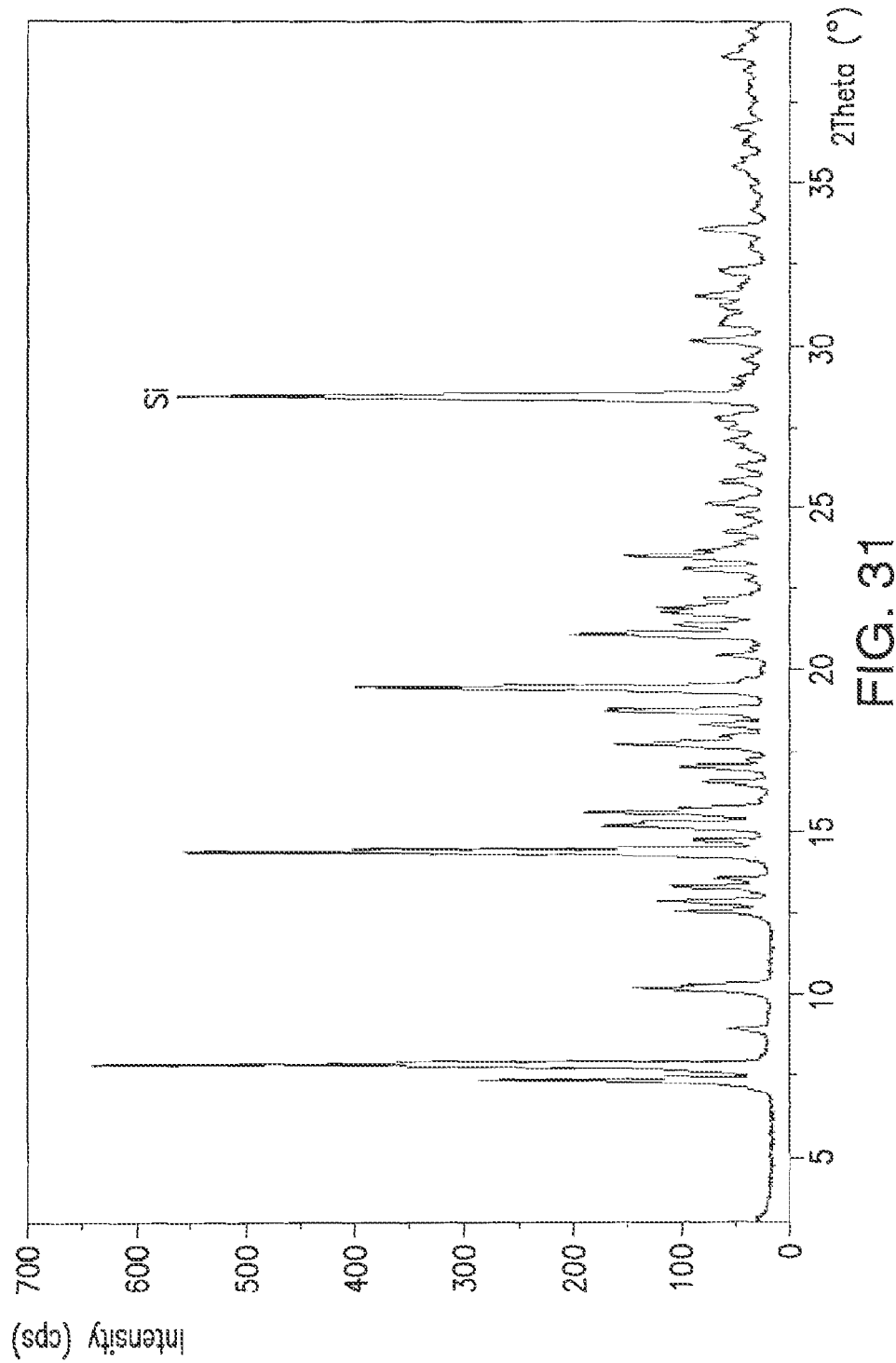
FIG. 31 shows a powder X-ray diffraction pattern for crystalline Cabazitaxel form III. The peak marked "Si" corresponds to the silicon internal standard.
Figure 32:
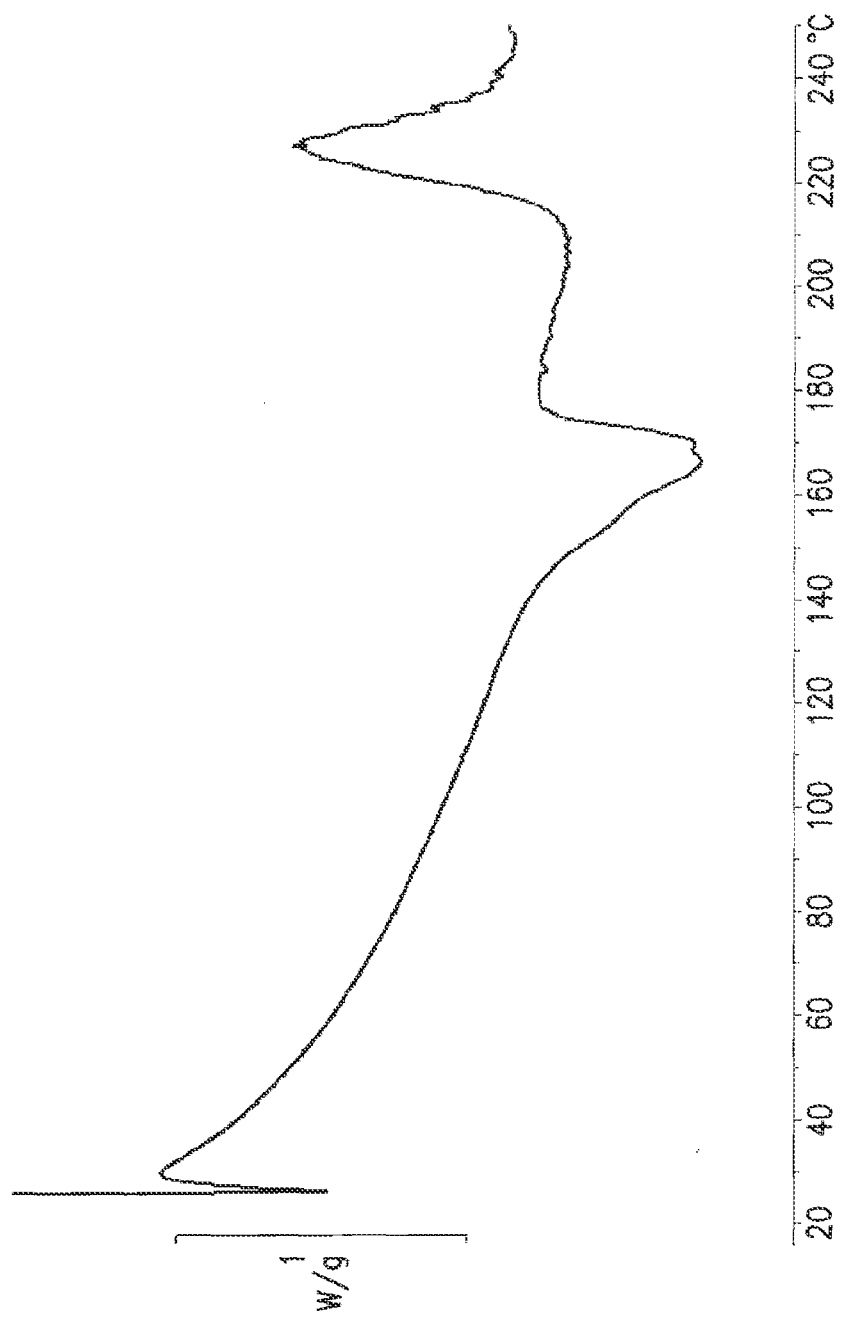
FIG. 32 shows a DSC thermogram for crystalline Cabazitaxel form III.
Figure 33:
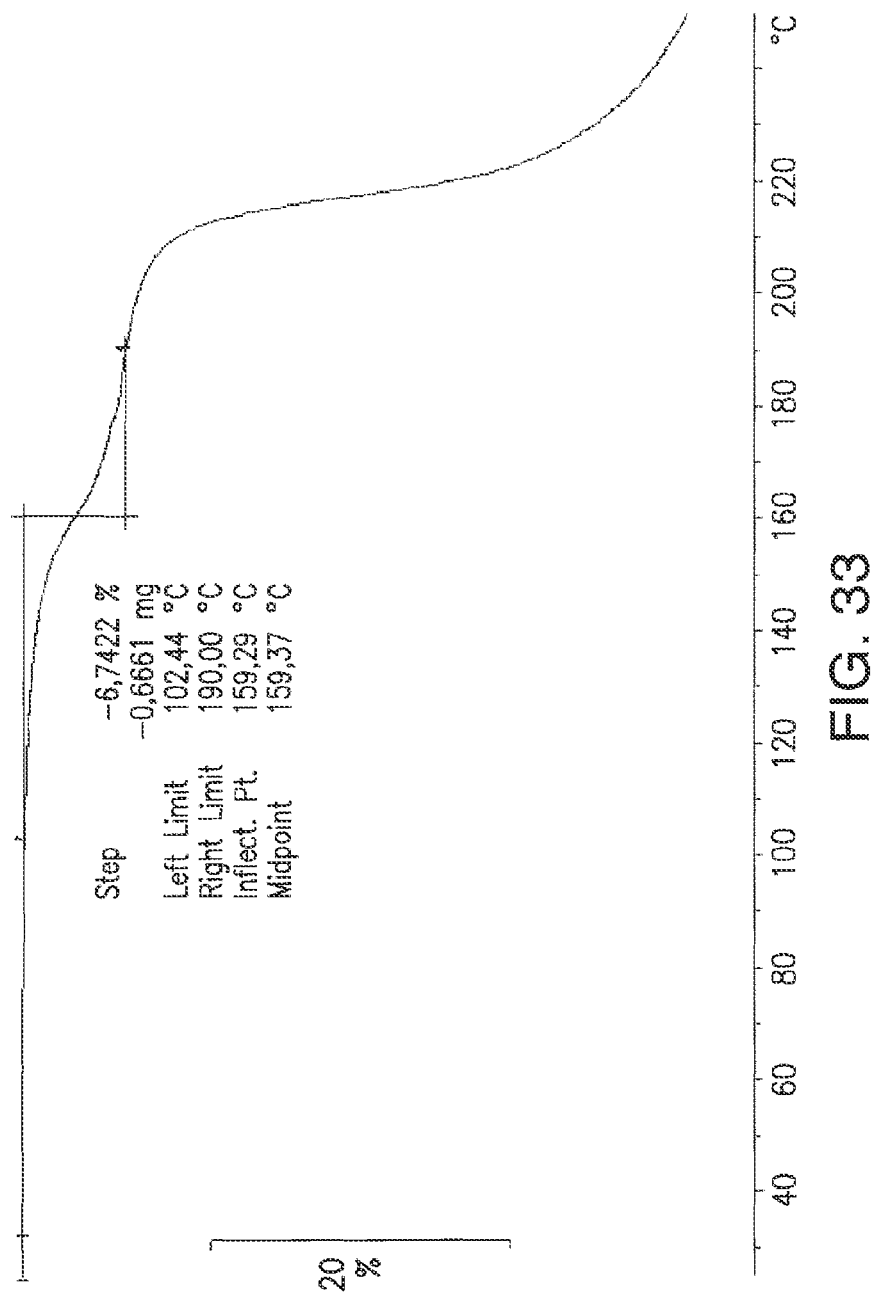
FIG. 33 shows a TGA thermogram for crystalline Cabazitaxel form III.
Figure 34:
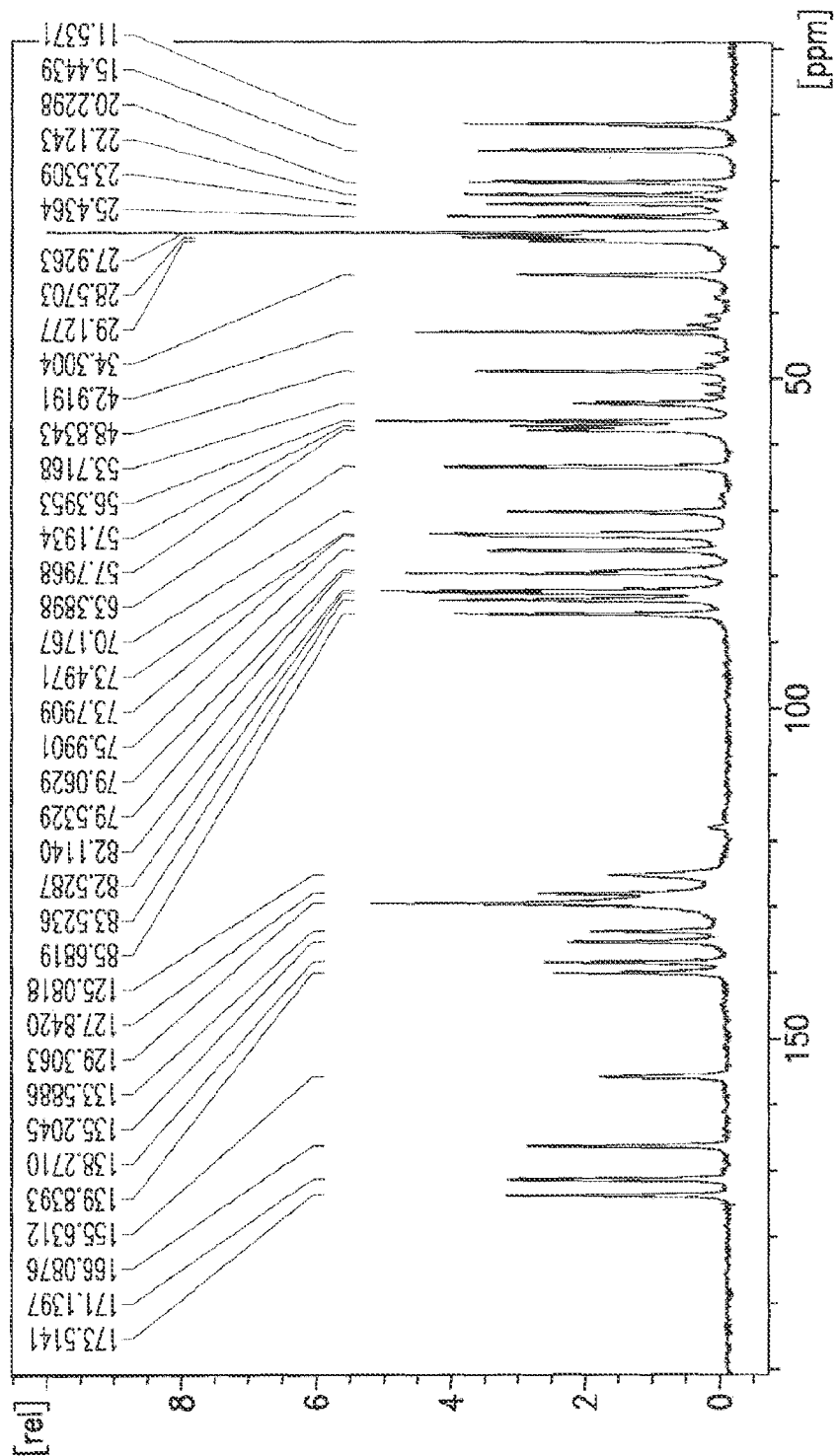
FIG. 34 shows a full-width solid state $^{13}$C NMR spectrum for crystalline Cabazitaxel form III.
Figure 35:
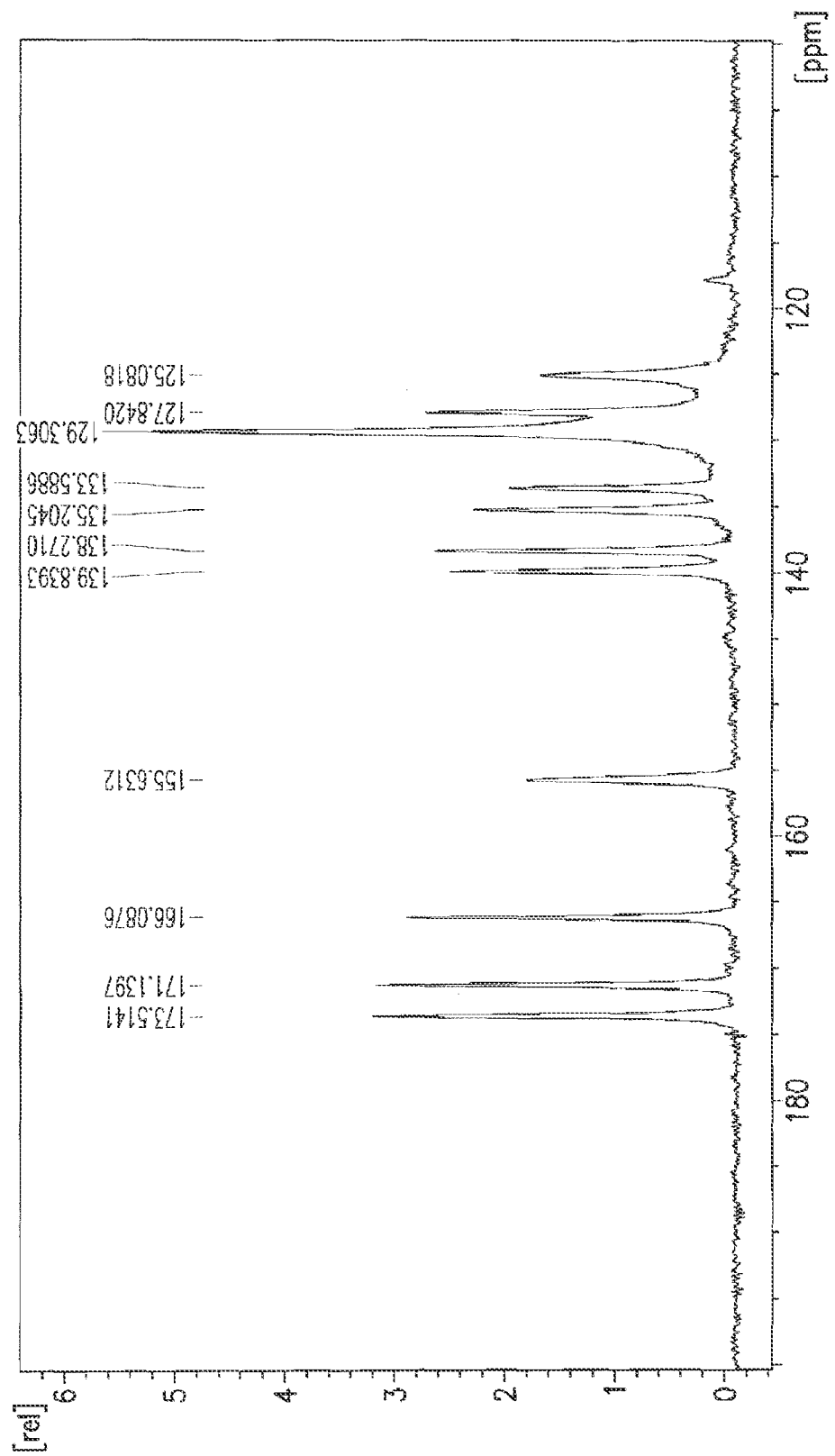
FIG. 35 shows an expanded solid state $^{13}$C NMR spectrum for crystalline Cabazitaxel form III in the range 200-100 ppm.
Figure 36:
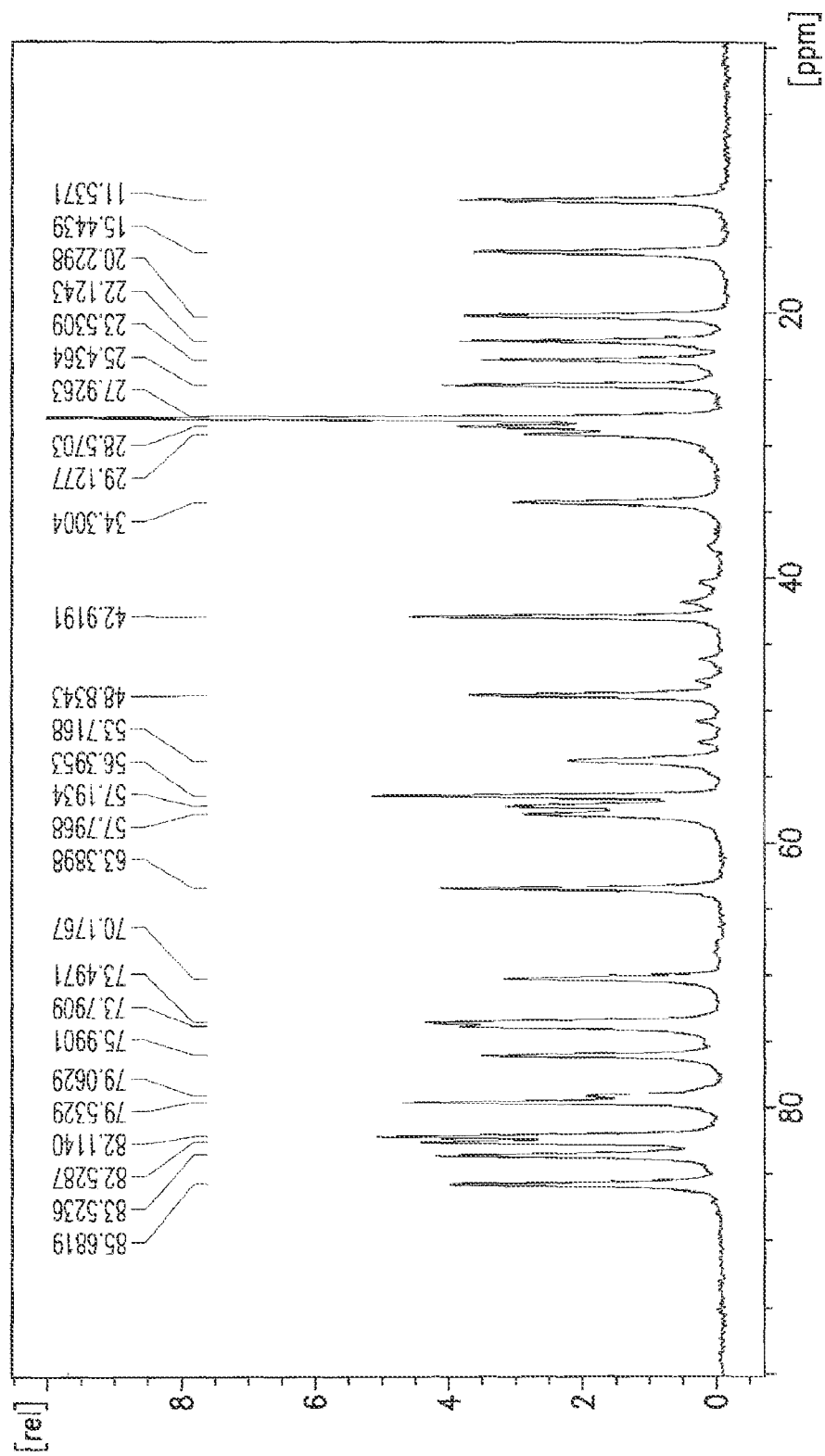
FIG. 36 shows an expanded solid state $^{13}$C NMR spectrum for crystalline Cabazitaxel form III in the range 100-0 ppm.

As used herein, the term crystalline Cabazitaxel isopropanol solvate form III refers to crystalline Cabazitaxel isopropanol solvate characterized by data selected from: a powder X-ray diffraction pattern having peaks at 7.4, 9.0, 10.3, 13.3 and 13.6 degrees two theta±0.1 degrees two theta, and having no peak in the area from 10.5 to 12.1 degrees two theta; by a powder X-ray diffraction pattern substantially as depicted in FIG. 31; and by a combination of these data. Form III can be further characterized by an X-ray powder diffraction pattern having peaks at 7.4, 9.0, 10.3, 13.3 and 13.6 degrees two theta±0.1 degrees two theta, and having no peak in the area from 10.5 to 12.1 degrees two theta, and also having an additional one, two, three, four or five peaks selected from 7.9, 12.9, 15.2, 15.3 and 19.5 degrees 2-theta±0.1 degrees 2-theta. Crystalline Cabazitaxel isopropanol solvate is described in WO2012142117 which is herein incorporated by reference in its entirety.

The present invention encompasses alkyl acetate solvates of Cabazitaxel. The present invention further encompasses an ethyl acetate solvate of Cabazitaxel. Particularly, the present invention encompasses crystalline Cabazitaxel ethyl acetate solvate, designated as Form VII.

Form VII can be characterized by data selected from one or more of the following: a powder X-ray diffraction pattern having peaks at 7.9, 8.6, 10.0, 10.2 and 15.8 degrees two theta±0.1 degrees two theta, and also having no peak in the area from 10.5 to 12.1 degrees two theta; by a powder X-ray diffraction pattern substantially as depicted in FIG. 1; and by combinations of these data.

Form VII, characterized by a powder X-ray diffraction pattern having peaks at 7.9, 8.6, 10.0, 10.2 and 15.8 degrees two theta±0.1 degrees two theta, and also having no peak in the area from 10.5 to 12.1 degrees two theta, can be further characterized by an additional one, two, three, four or five PXRD peaks selected from 7.5, 13.8, 14.1, 15.0 and 18.0 degrees two theta±0.1 degrees two theta.

Figure 2:
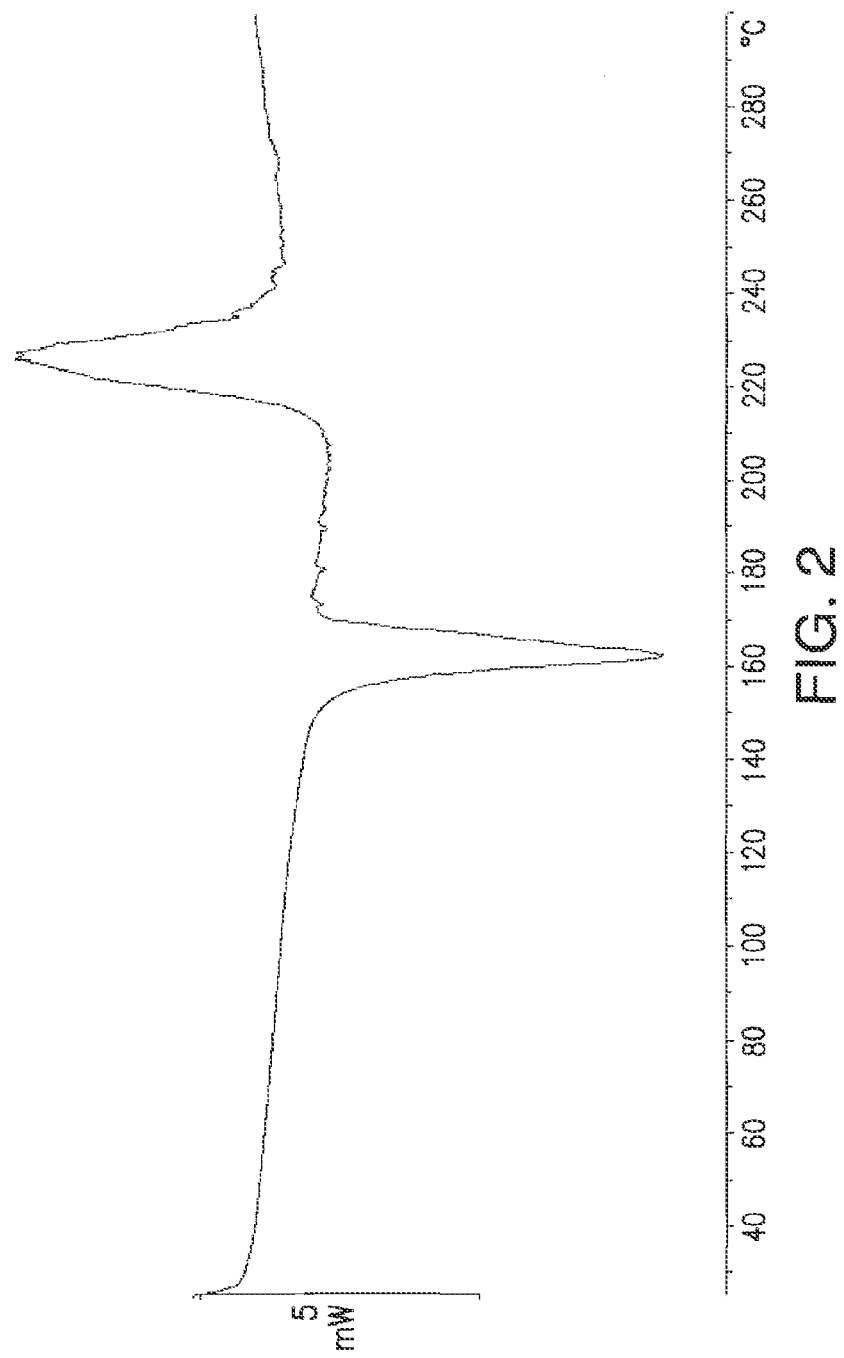
FIG. 2 shows a DSC thermogram for crystalline Cabazitaxel form VII.
Figure 3:
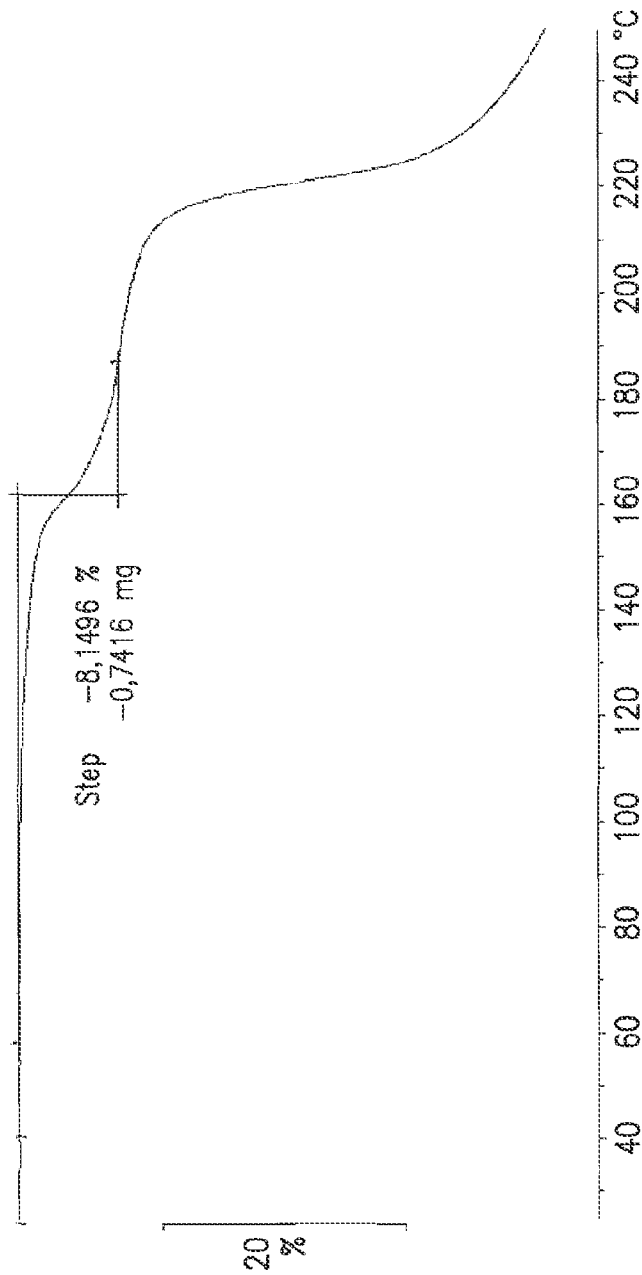
FIG. 3 shows a TGA thermogram for crystalline Cabazitaxel form VII.

Form VII can be further characterized by data selected from one or more of the following: a DSC thermogram substantially as depicted in FIG. 2; a DSC melting peak at about 162.0±4° C. and DSC melting onset at about 157.2±4° C.; a TGA thermogram substantially as depicted in FIG. 3; and by combinations of these data. The theoretical content of ethyl acetate for a monosolvate of cabazitaxel is about 9.5% w/w. For example, the content of the ethyl acetate can be about 8.1%±2 w/w as determined by TGA.

Form VII can be characterized by any combination of the above data.

As discussed above, Cabazitaxel Form VII has advantageous properties. In particular, the crystalline Cabazitaxel Form VII of the present invention is a low-hygroscopicity form, and it does not convert to any other form of Cabazitaxel in various relative humidity (RH) conditions, such as normal atmospheric humidity, 60%, 80% and 100% RH and at a temperature of about room temperature, when compared to the acetone solvate (as disclosed in WO2005/028462) that already transform to the anhydrous form B (as disclosed in WO2009/115655) after two days.

In another embodiment the present invention encompasses an isopropyl acetate solvate of cabazitaxel. Specifically, the present invention encompasses a crystalline Cabazitaxel isopropyl acetate solvate, designated as Form VIII.

Figure 4:
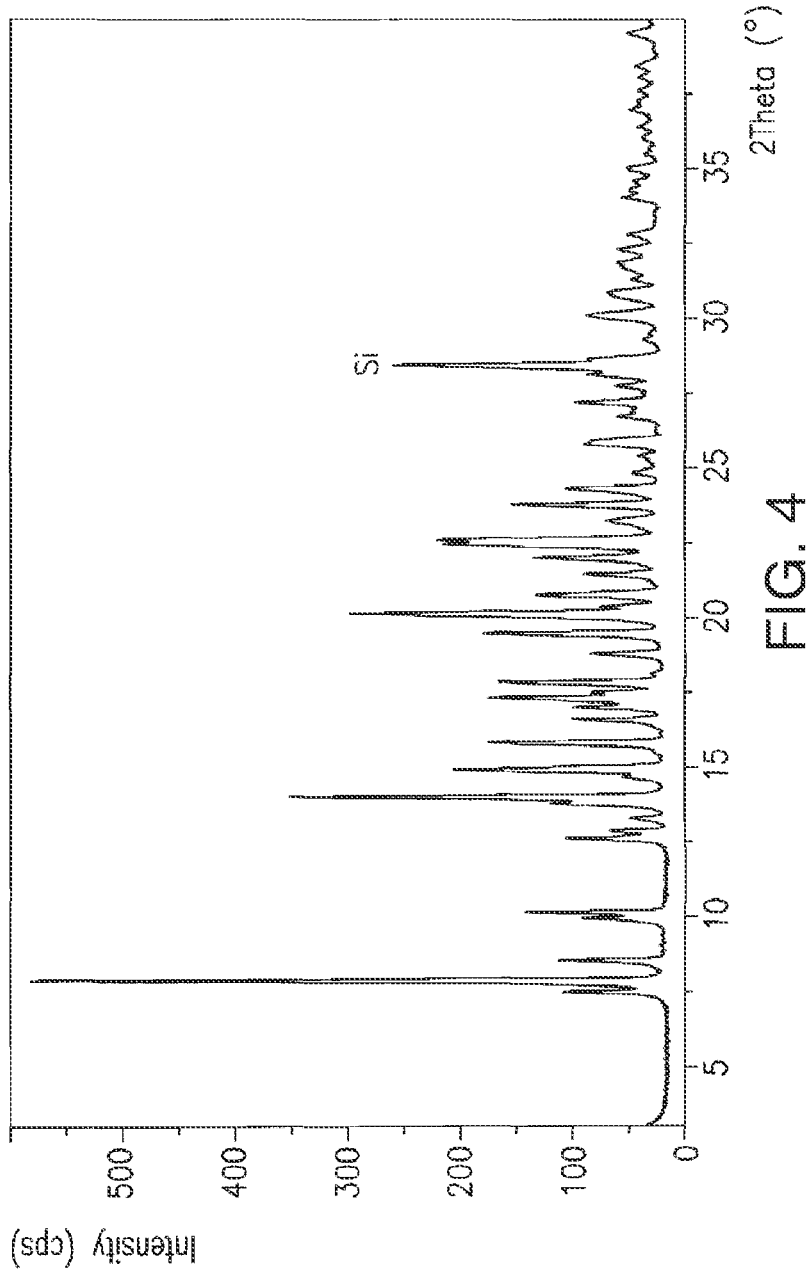
FIG. 4 shows a PXRD pattern for crystalline Cabazitaxel form VIII.

Form VIII can be characterized by data selected from one or more of the following: a powder X-ray diffraction pattern having peaks at 7.9, 8.6, 10.0, 10.2 and 16.6 degrees two theta±0.1 degrees two theta, and also having no peak in the area from 10.5 to 12.1 degrees two theta; and by a powder X-ray diffraction pattern substantially as depicted in FIG. 4; and by a combination of these data.

Form VIII, characterized by a powder X-ray diffraction pattern having peaks at 7.9, 8.6, 10.0, 10.2 and 16.6 degrees two theta±0.1 degrees two theta, and also having no peak in the area from 10.5 to 12.1 degrees two theta, can be further characterized by an additional one, two, three, four or five PXRD peaks selected from 7.5, 12.6, 14.0, 14.9 and 15.8 degrees two theta±0.1 degrees two theta.

Figure 5:
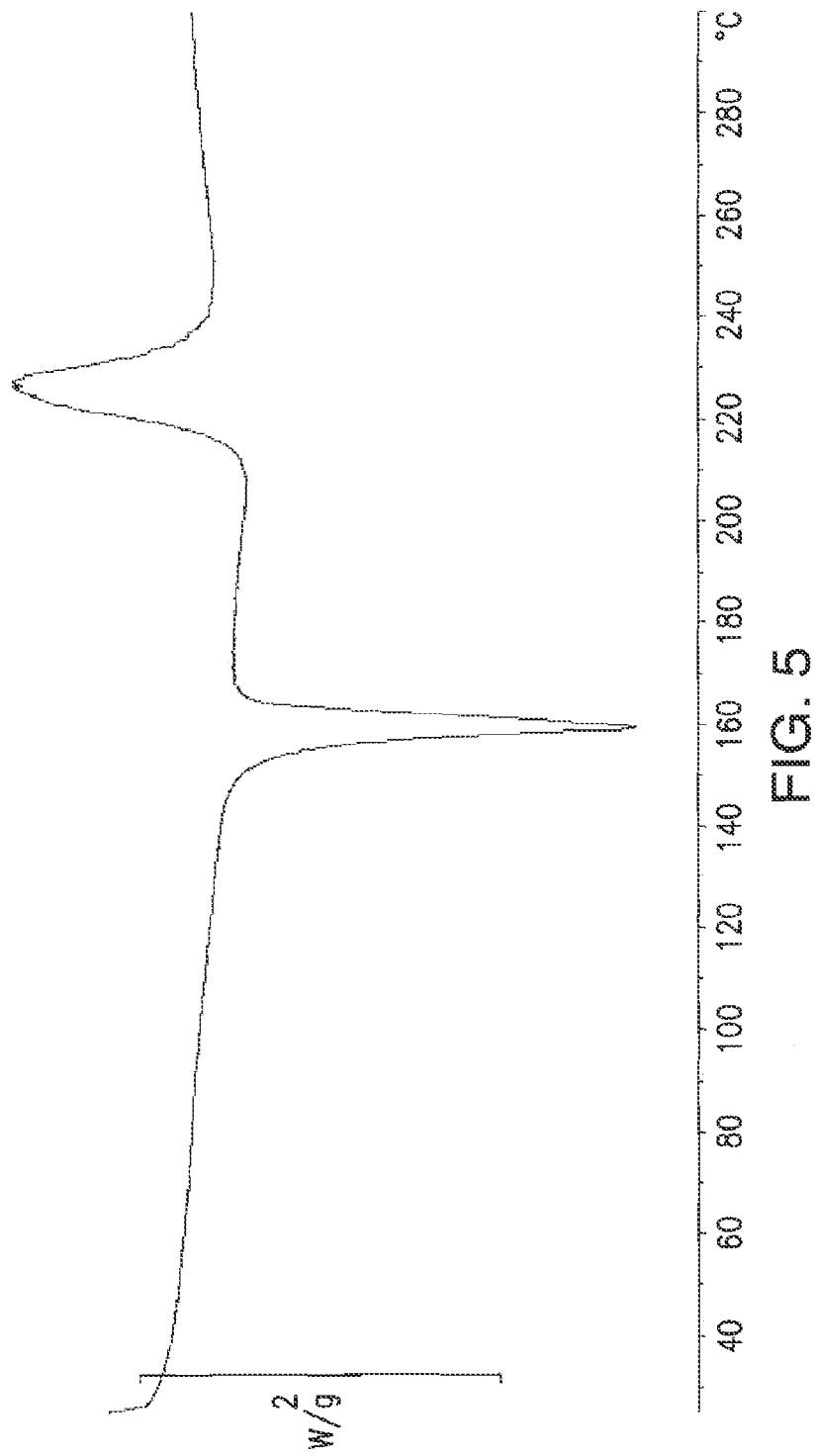
FIG. 5 shows a DSC thermogram for crystalline Cabazitaxel form VIII.
Figure 6:
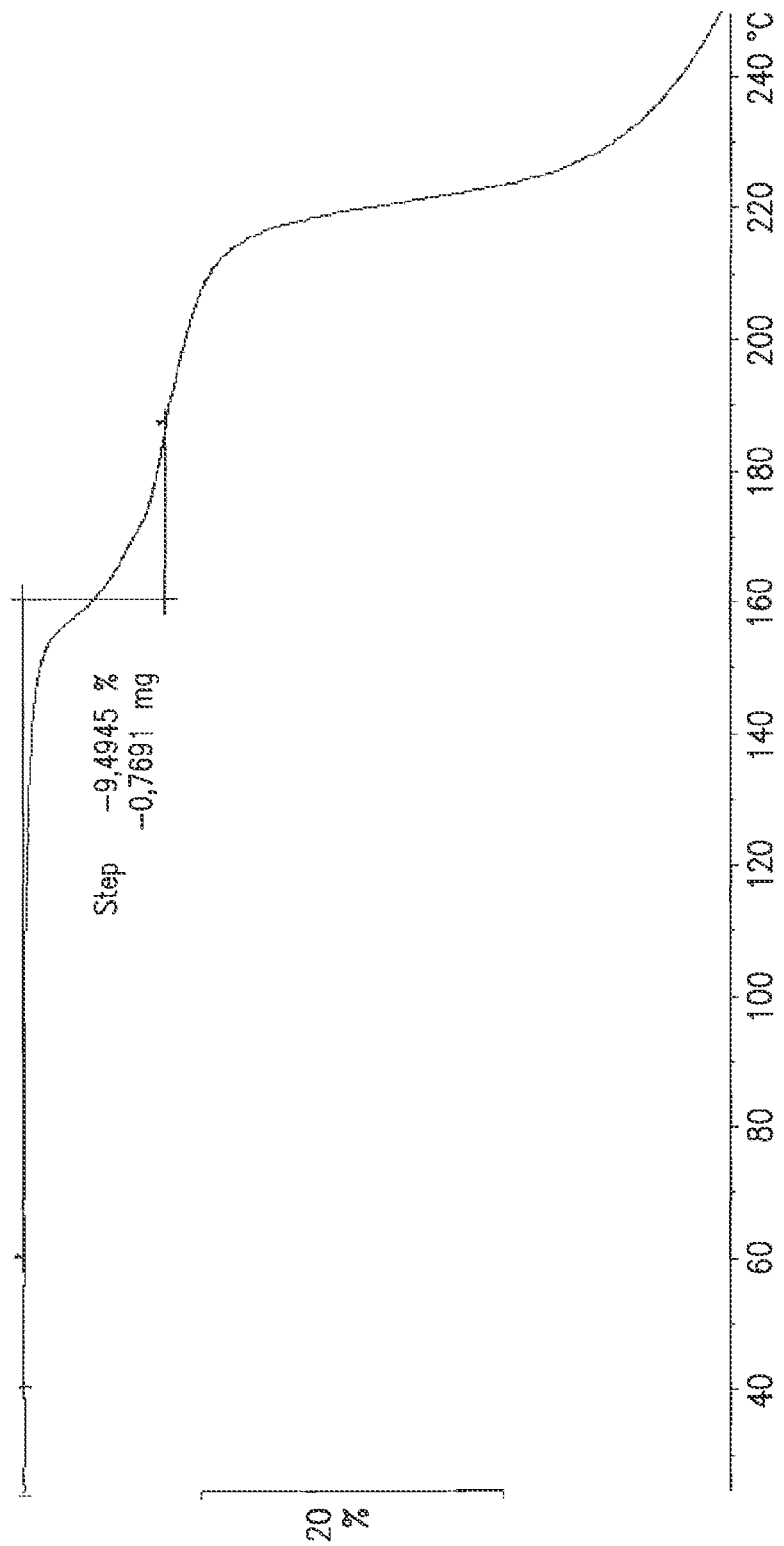
FIG. 6 shows a TGA thermogram for crystalline Cabazitaxel form VIII.

Form VIII can be further characterized by data selected from one or more of the following: a DSC thermogram substantially as depicted in FIG. 5; DSC melting peak at about 159.1±4° C. and DSC melting onset at about 155.7±4° C.; a TGA thermogram substantially as depicted in FIG. 6; and by combinations of these data. The theoretical content of isopropyl acetate for a monosolvate of cabazitaxel is about 10.9% w/w. For example, the content of the isopropyl acetate can be about 9.5%±2 w/w as determined by TGA.

Form VIII can be characterized by any combination of the above data.

The present invention encompasses ketone solvates of Cabazitaxel. In one embodiment, the present invention encompasses methyl ethyl ketone ("MEK") solvate. Particularly, the present invention encompasses crystalline Cabazitaxel methyl ethyl ketone solvate, designated as Form IX.

Figure 7:
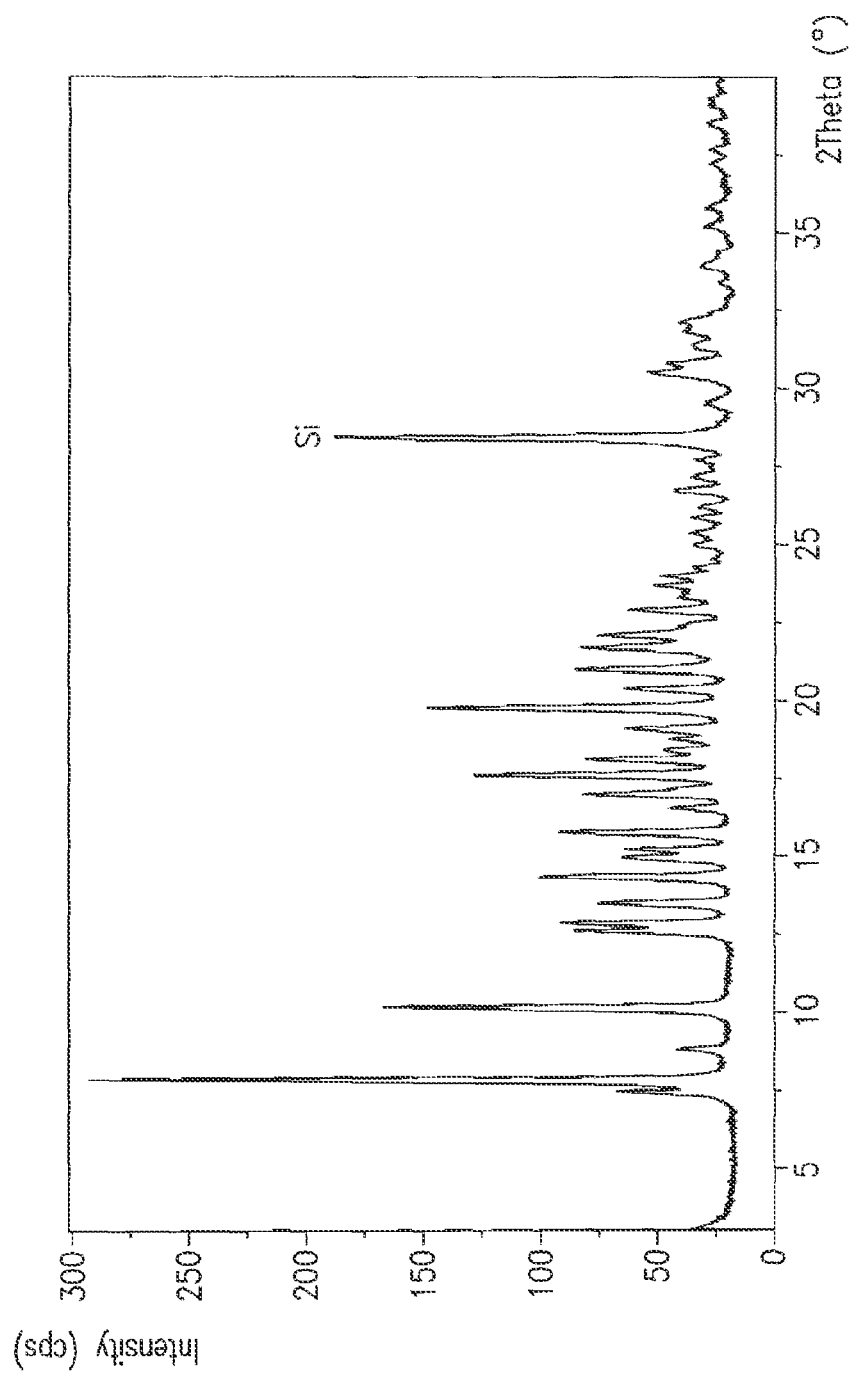
FIG. 7 shows a PXRD pattern for crystalline Cabazitaxel form IX.

Form IX can be characterized by data selected from one or more of the following: a powder X-ray diffraction pattern having peaks at 7.9, 8.8, 10.2, 13.5 and 19.8 degrees two theta±0.1 degrees two theta and also having no peak in the area from 10.5 to 12.1 degrees two theta; by a powder X-ray diffraction pattern substantially as depicted in FIG. 7; and by a combination of these data.

Form IX, characterized by a powder X-ray diffraction pattern having peaks at 7.9, 8.8, 10.2, 13.5 and 19.8 degrees two theta±0.1 degrees two theta and also having no peak in the area from 10.5 to 12.1 degrees two theta, can be further characterized by data selected from: an additional one, two, three, four or five PXRD peaks selected from 7.5, 12.6, 12.9, 15.2 and 17.0 degrees two theta±0.1 degrees two theta.

Figure 8:
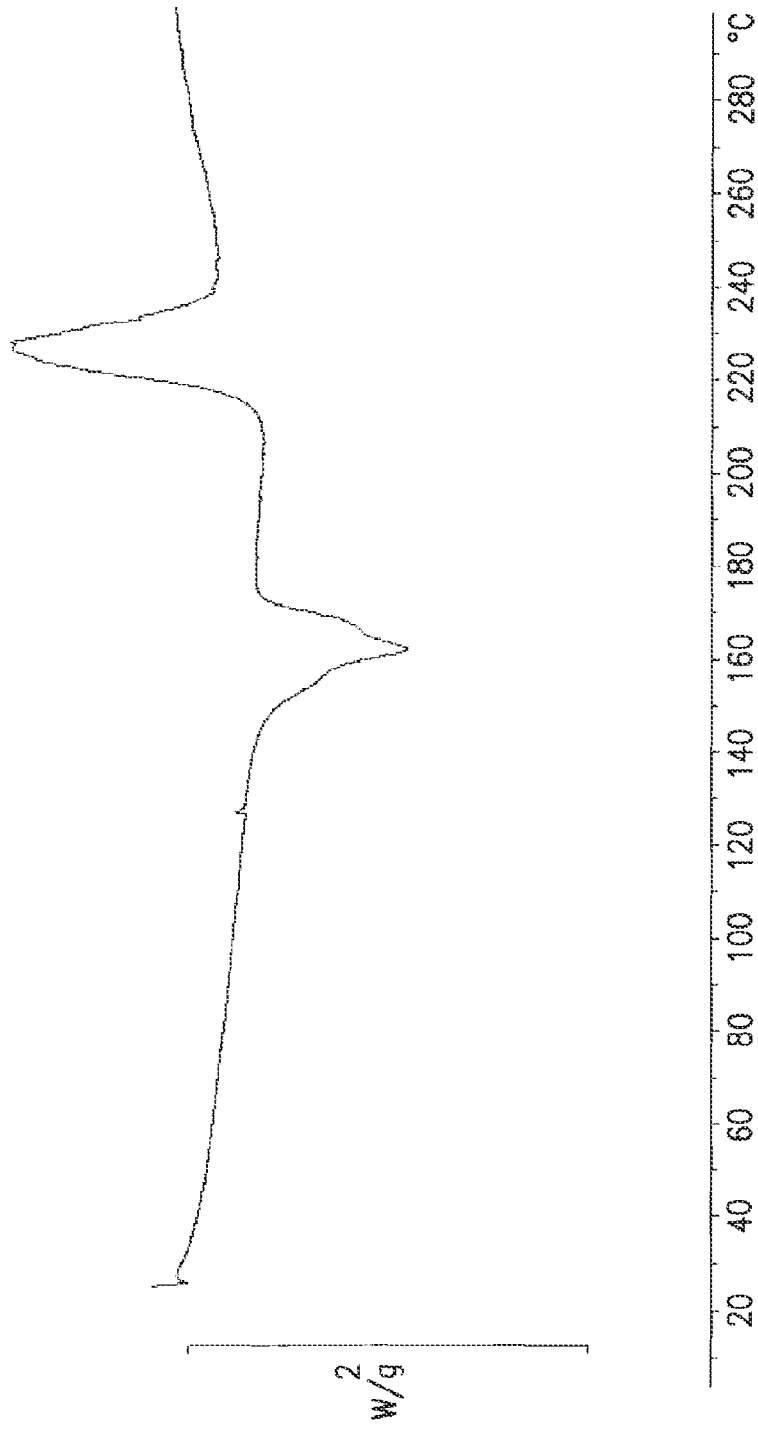
FIG. 8 shows a DSC thermogram for crystalline Cabazitaxel form IX.
Figure 9:
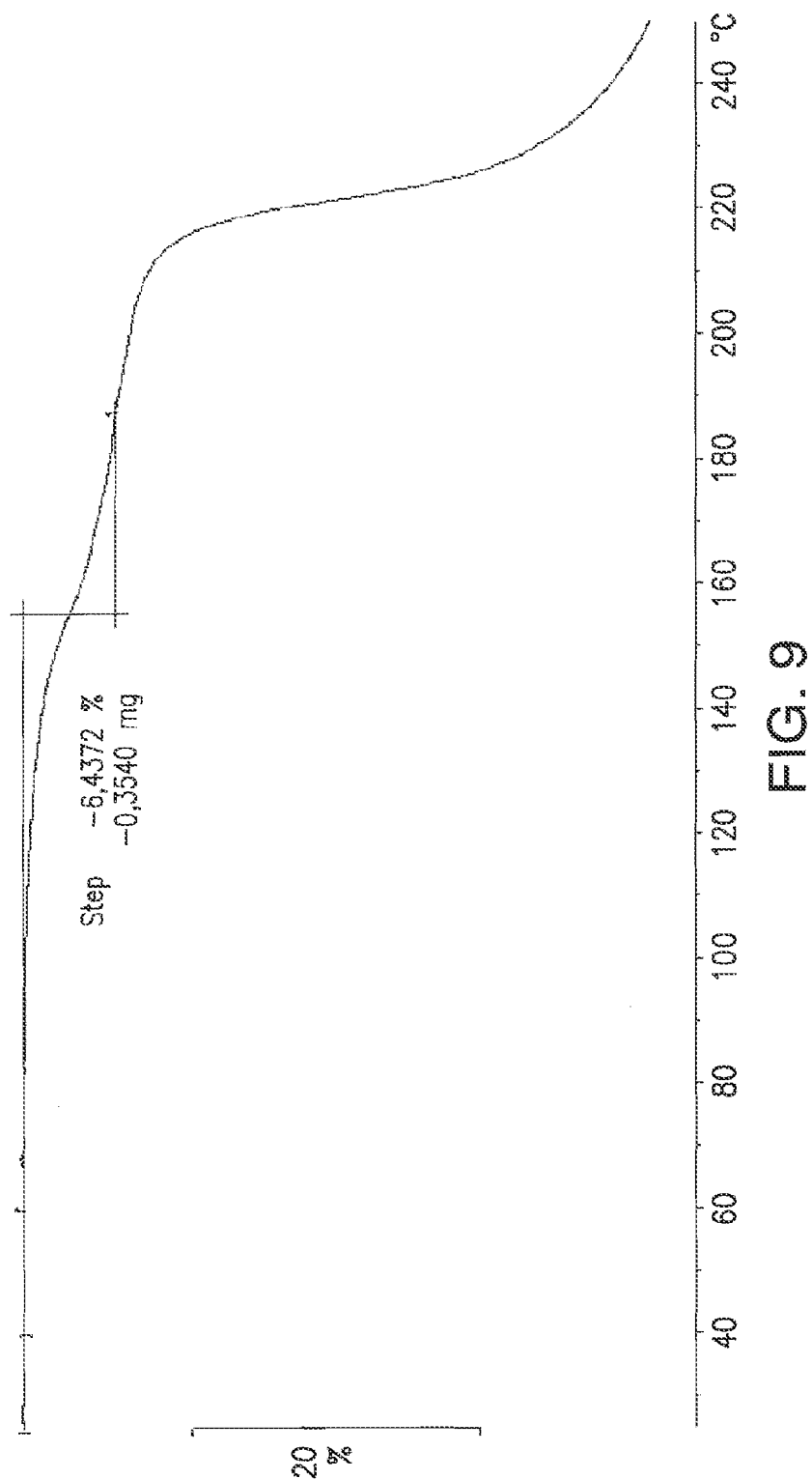
FIG. 9 shows a TGA thermogram for crystalline Cabazitaxel form IX.

Form IX can be further characterized by data selected from one or more of the following: a DSC thermogram substantially as depicted in FIG. 8; a DSC melting peak at about 162.1±4° C. and a DSC melting onset at about 154.6±4° C.; a TGA thermogram substantially as depicted in FIG. 9; and by combinations of these data. The theoretical content of methyl ethyl ketone for a monosolvate of cabazitaxel is about 7.9% w/w. For example, the content of the methyl ethyl ketone can be about 6.4%±2 w/w as determined by TGA.

Form IX can be characterized by any combination of the above data.

The present invention further encompasses a methyl isobutyl ketone ("MIBK") solvate of cabazitaxel. In particular, the present invention encompasses crystalline Cabazitaxel methyl isobutyl ketone solvate, designated as Form X.

Figure 10:
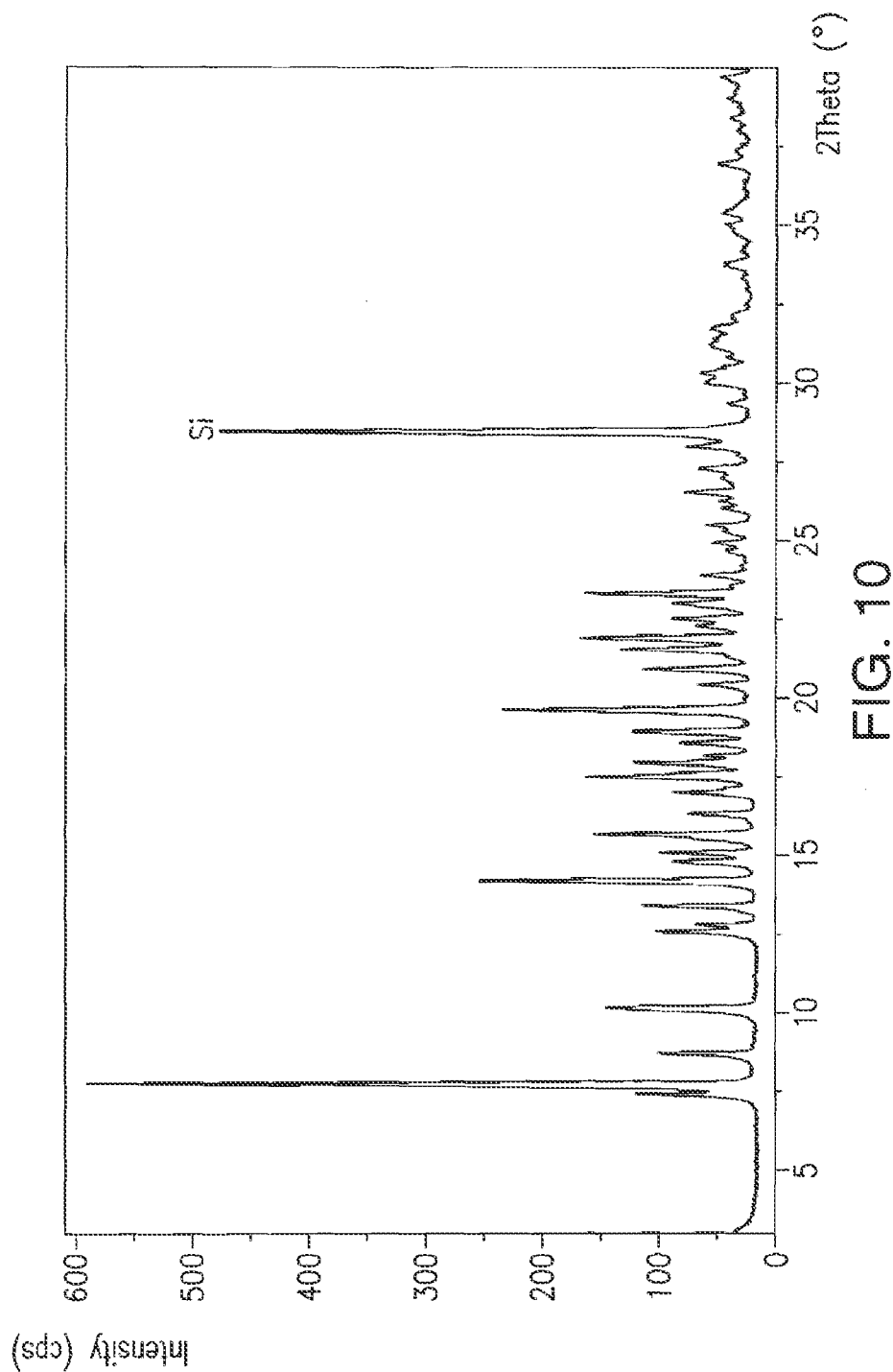
FIG. 10 shows a PXRD pattern for crystalline Cabazitaxel form X.

Form X can be characterized by data selected from one or more of the following: a powder X-ray diffraction pattern having peaks at 7.7, 8.7, 13.4, 14.2 and 15.6 degrees two theta±0.1 degrees two theta and also having no peak in the area from 10.5 to 12.1 degrees two theta; by a powder X-ray diffraction pattern substantially as depicted in FIG. 10; and by a combination of these data.

Form X, characterized by a powder X-ray diffraction pattern having peaks at 7.7, 8.7, 13.4, 14.2 and 15.6 degrees two theta±0.1 degrees two theta and also having no peak in the area from 10.5 to 12.1 degrees two theta, can be further characterized by an additional one, two, three, four or five PXRD peaks selected from 7.4, 10.2, 12.6, 12.8 and 18.9 degrees two theta±0.1 degrees two theta.

Figure 11:
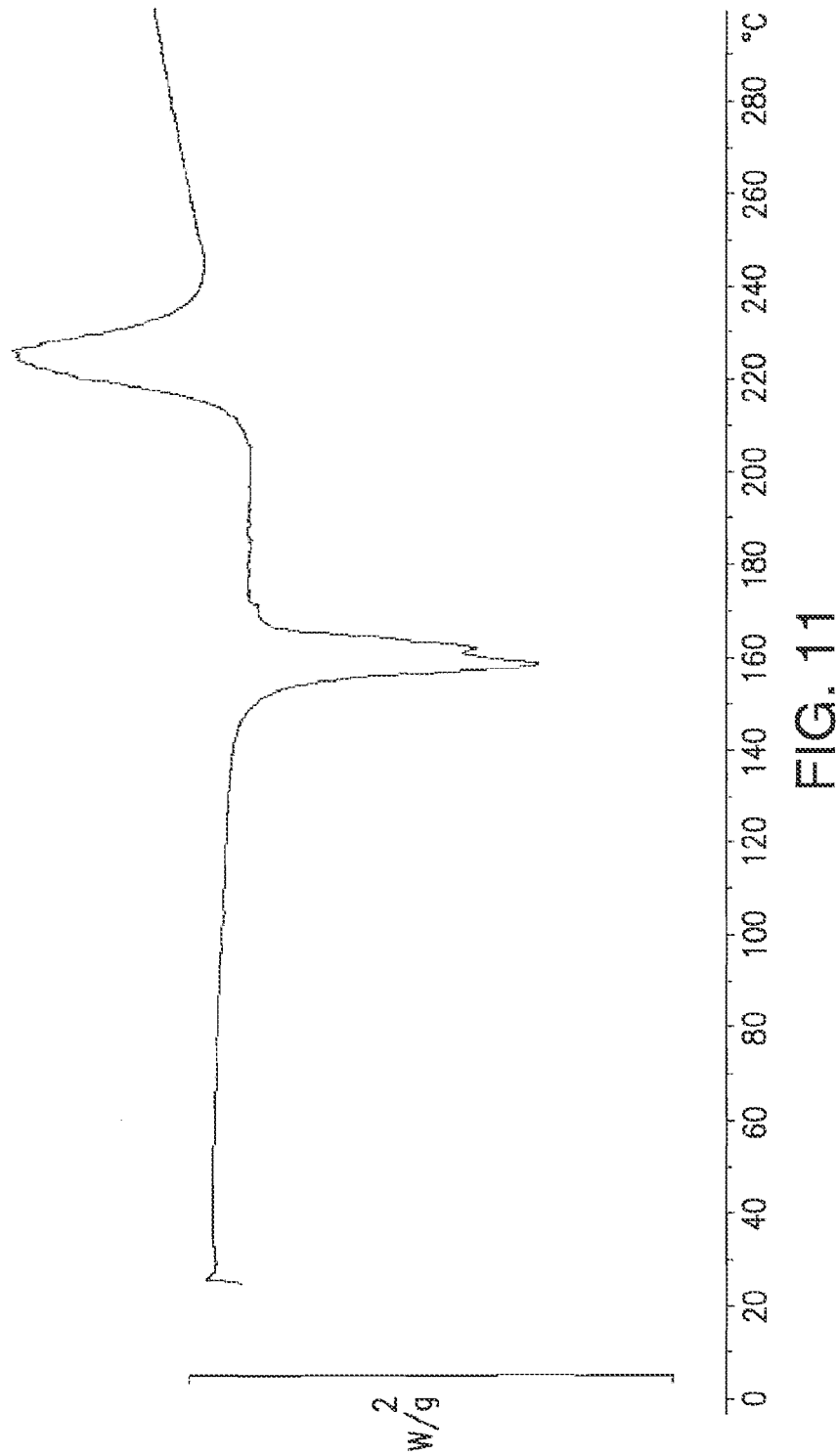
FIG. 11 shows a DSC thermogram for crystalline Cabazitaxel form X.
Figure 12:
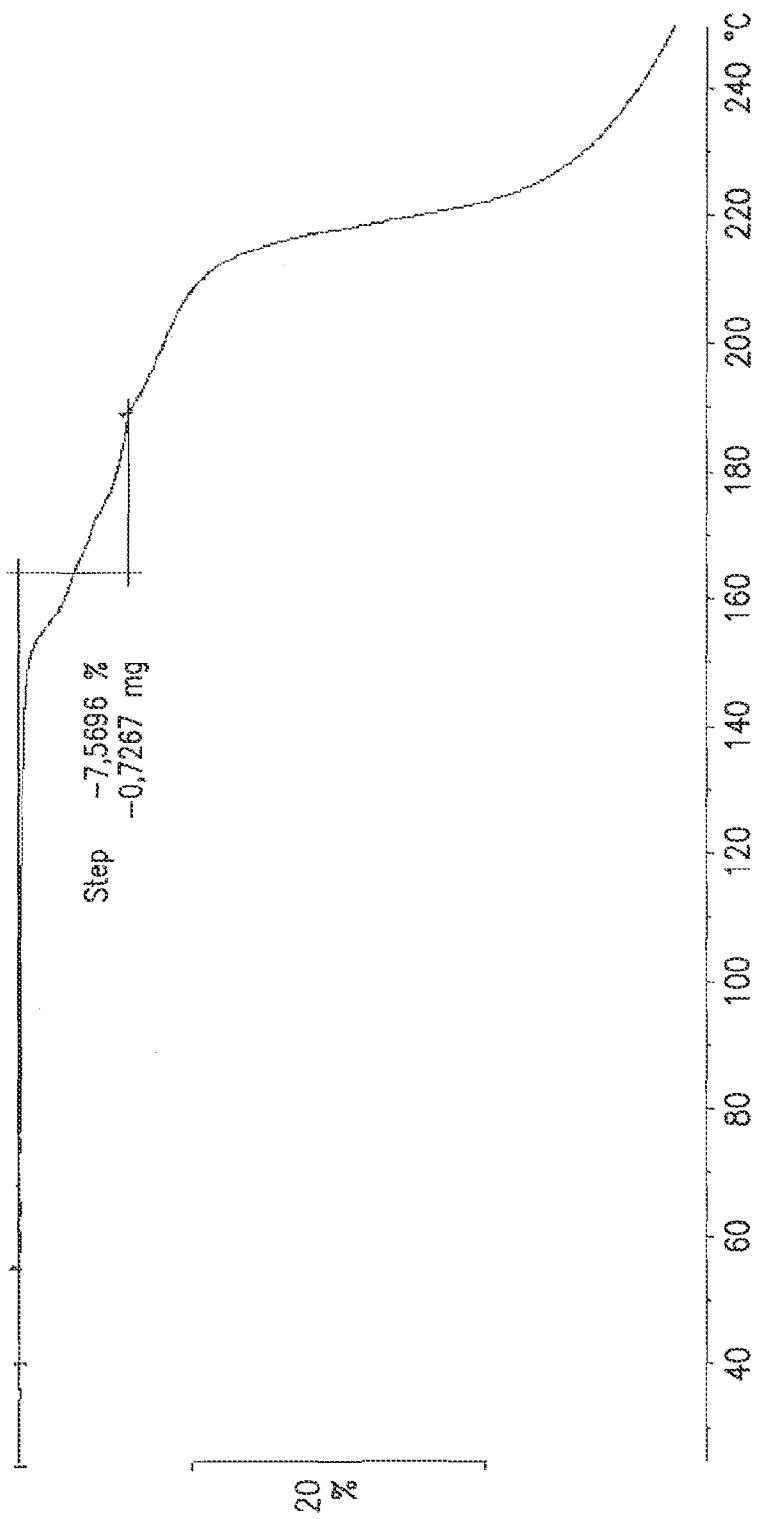
FIG. 12 shows a TGA thermogram for crystalline Cabazitaxel form X.

Form X can be further characterized by data selected from one or more of the following: a DSC thermogram substantially as depicted in FIG. 11; a DSC double peak having maxima at about 158.4±4° C. and 162.1±4° C. and a DSC melting onset at about 154.2±4° C.; a TGA thermogram substantially as depicted in FIG. 12; and by combinations of these data. The theoretical content of methyl isobutyl ketone for a monosolvate of cabazitaxel is about 10.7% w/w. For example, the content of the methyl isobutyl ketone can be about 7.6%±2 w/w as determined by TGA.

Form X can be characterized by any combination of the above data.

As discussed above, Cabazitaxel Form X has advantageous properties. In particular, the crystalline Cabazitaxel Form X of the present invention is a low-hygroscopicity form, and it does not convert to any other forms of Cabazitaxel in various relative humidity (RH) conditions, such as normal atmospheric humidity, 60%, 80% and 100% RH and at a temperature of about room temperature, when compared to the acetone solvate that already transform to the anhydrous form B after two days.

The present invention encompasses alcohol solvates of Cabazitaxel. In one embodiment, the present invention encompasses a 2-butanol solvate of cabazitaxel. Particularly, the present invention encompasses crystalline Cabazitaxel 2-butanol solvate, designated as Form XI.

Figure 13:
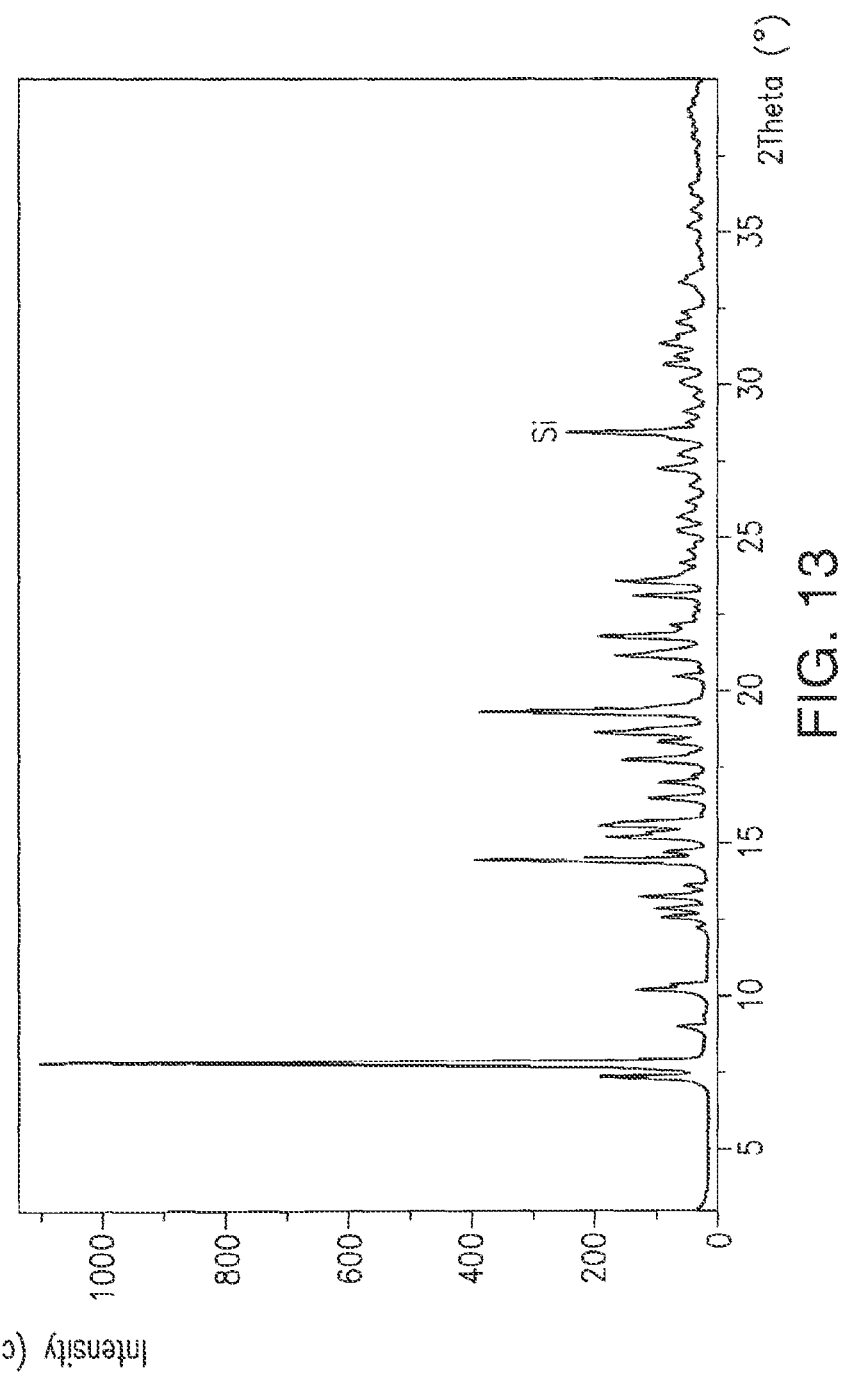
FIG. 13 shows a PXRD pattern for crystalline Cabazitaxel form XI.

Form XI can be characterized by data selected from one or more of the following: a powder X-ray diffraction pattern having peaks at 7.9, 10.2, 10.4, 12.6 and 16.5 degrees two theta±0.1 degrees two theta and also having no peak in the area from 10.5 to 12.1 degrees two theta; by a powder X-ray diffraction pattern substantially as depicted in FIG. 13; and by a combination of these data.

Figure 14:
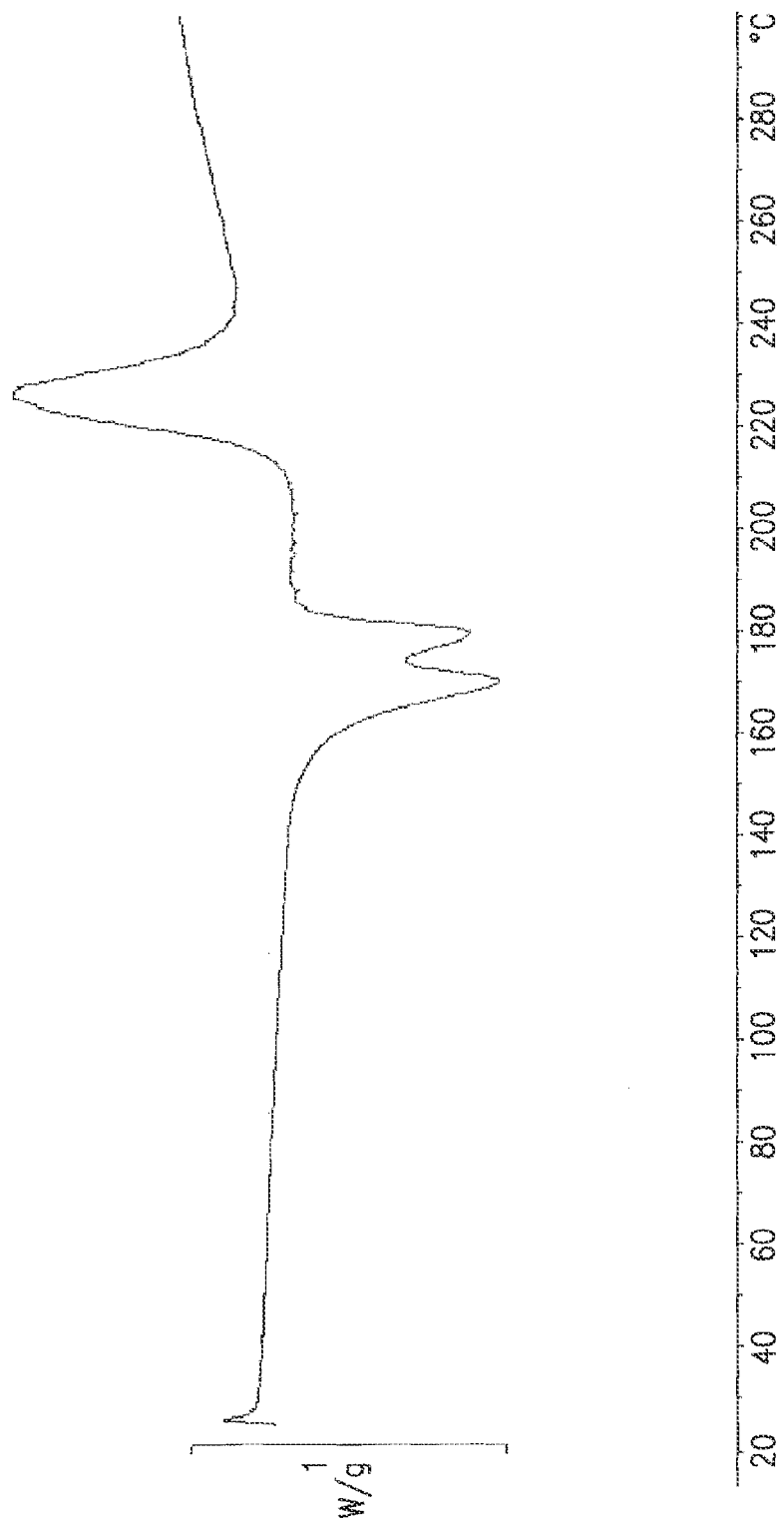
FIG. 14 shows a DSC thermogram for crystalline Cabazitaxel form XI.
Figure 15:
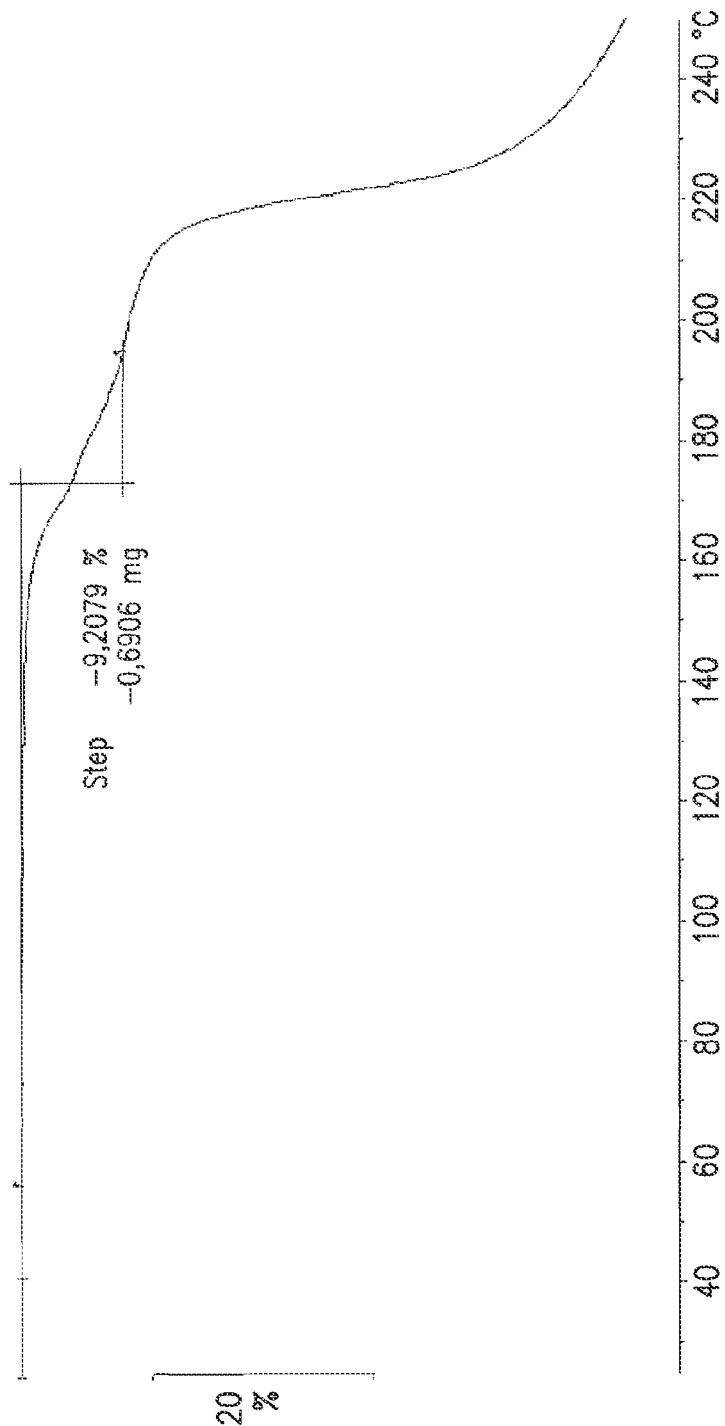
FIG. 15 shows a TGA thermogram for crystalline Cabazitaxel form XI.

Form XI, characterized by a powder X-ray diffraction pattern having peaks at 7.9, 10.2, 10.4, 12.6 and 16.5 degrees two theta±0.1 degrees two theta and also having no peak in the area from 10.5 to 12.1 degrees two theta, can be further characterized by an additional one, two, three, four or five PXRD peaks selected from 7.4, 9.0, 12.2, 13.3 and 14.5 degrees two theta±0.1 degrees two theta Form XI can be further characterized by data selected from one or more of the following: a DSC thermogram substantially as depicted in FIG. 14; a DSC double peak having maxima at about 170.1±4° C. and 179.6±4° C. and a DSC melting onset at about 160.4±4° C.; a TGA thermogram substantially as depicted in FIG. 15; and by combinations of these data. The theoretical content of 2-butanol for a monosolvate of cabazitaxel is about 8.1% w/w. For example, the content of the 2-butanol can be about 9.2%±2 w/w as determined by TGA.

Form XI can be characterized by any combination of the above data.

Figure 16:
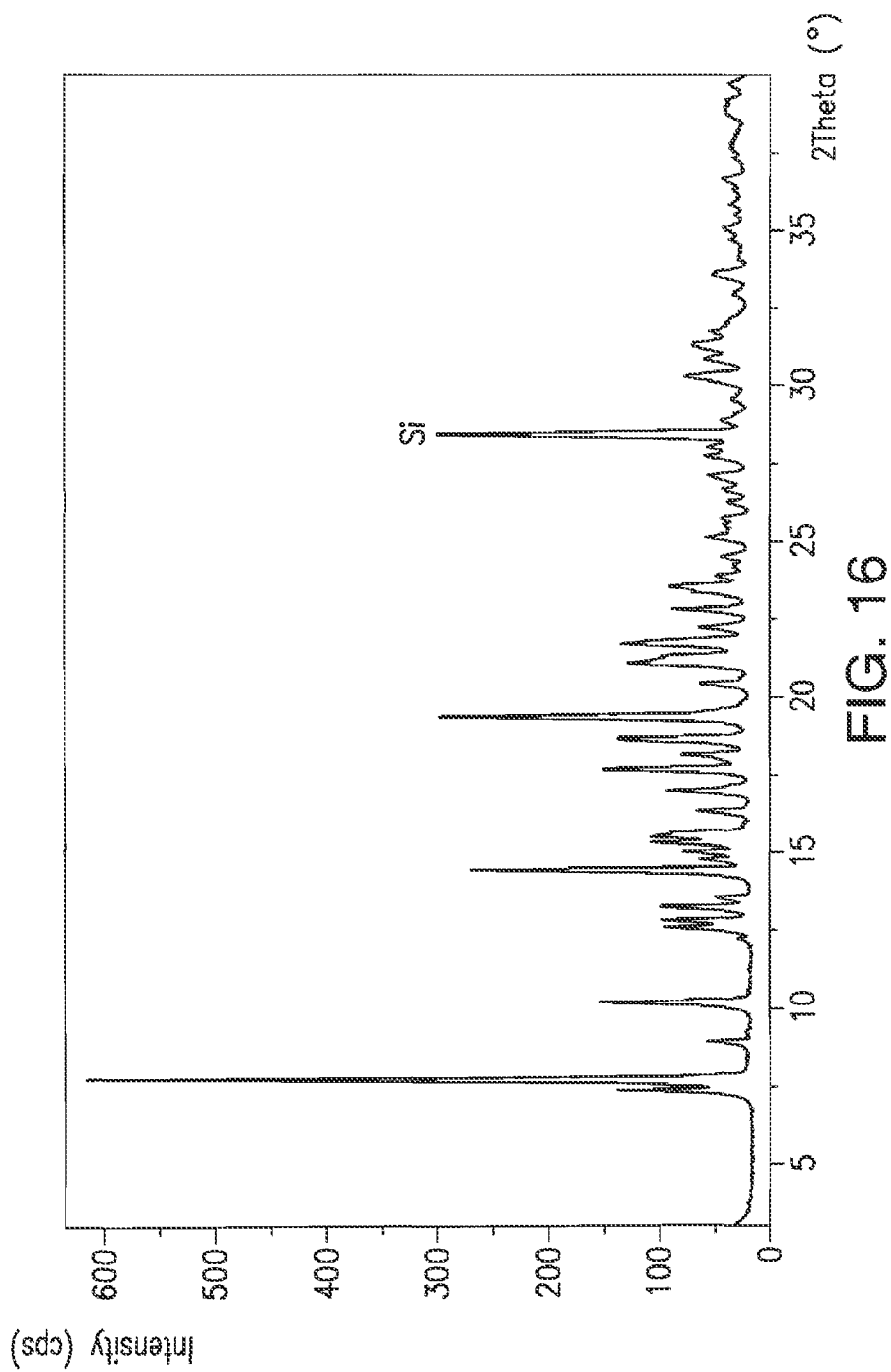
FIG. 16 shows a PXRD pattern for crystalline Cabazitaxel form XII.

In yet another embodiment the present invention encompasses an isobutanol solvate of cabazitaxel. Specifically, the present invention encompasses a crystalline Cabazitaxel isobutanol solvate, designated as Form XII. Form XII can be characterized by data selected from one or more of the following: a powder X-ray diffraction pattern having peaks at 7.8, 10.2, 13.3, 14.5 and 17.7 degrees two theta±0.1 degrees two theta and also having no peak in the area from 10.5 to 12.1 degrees two theta; by a powder X-ray diffraction pattern substantially as depicted in FIG. 16; and by combinations of these data.

Form XII, characterized by a powder X-ray diffraction pattern having peaks at 7.8, 10.2, 13.3, 14.5 and 17.7 degrees two theta±0.1 degrees two theta and also having no peak in the area from 10.5 to 12.1 degrees two theta, can be further characterized by an additional one, two, three, four or five PXRD peaks selected from 7.4, 9.0, 12.2, 12.6 and 19.4 degrees two theta±0.1 degrees two theta.

Figure 17:
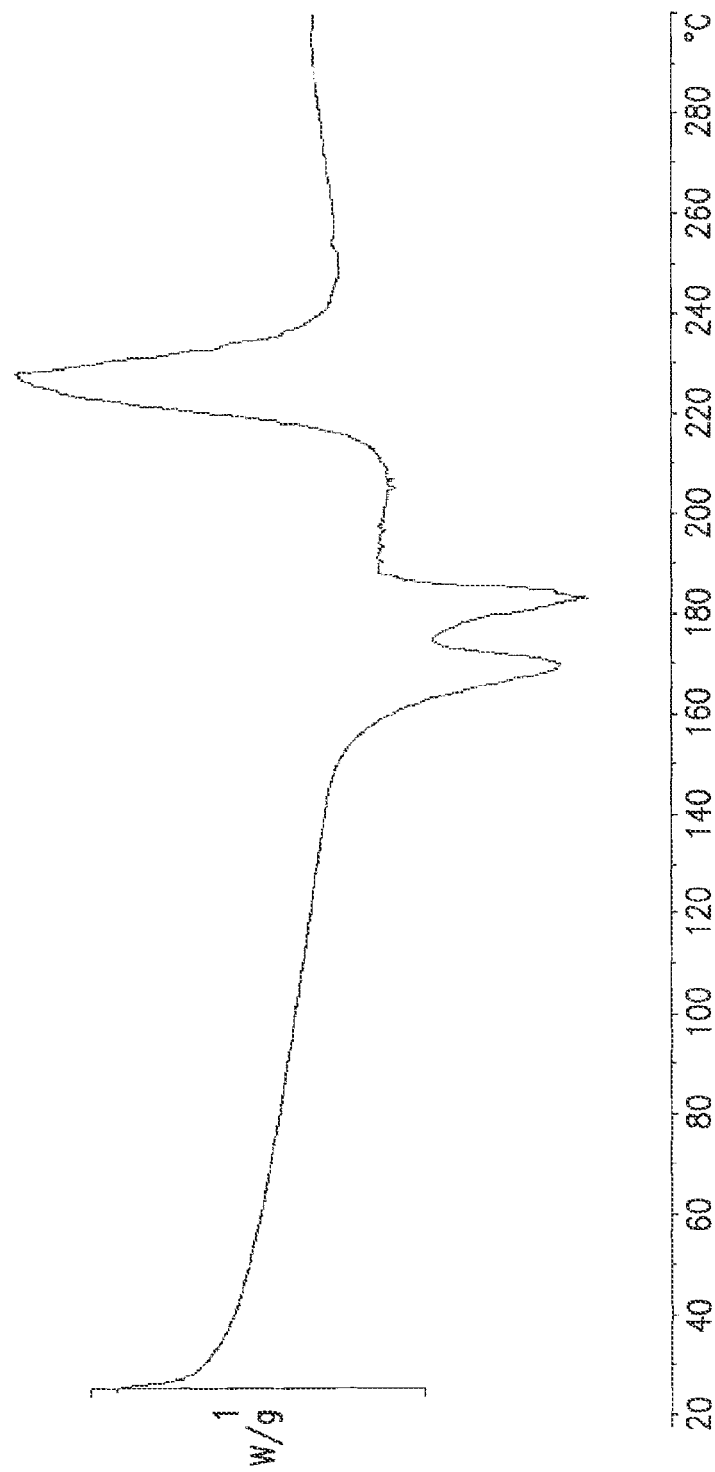
FIG. 17 shows a DSC thermogram for crystalline Cabazitaxel form XII.
Figure 18:
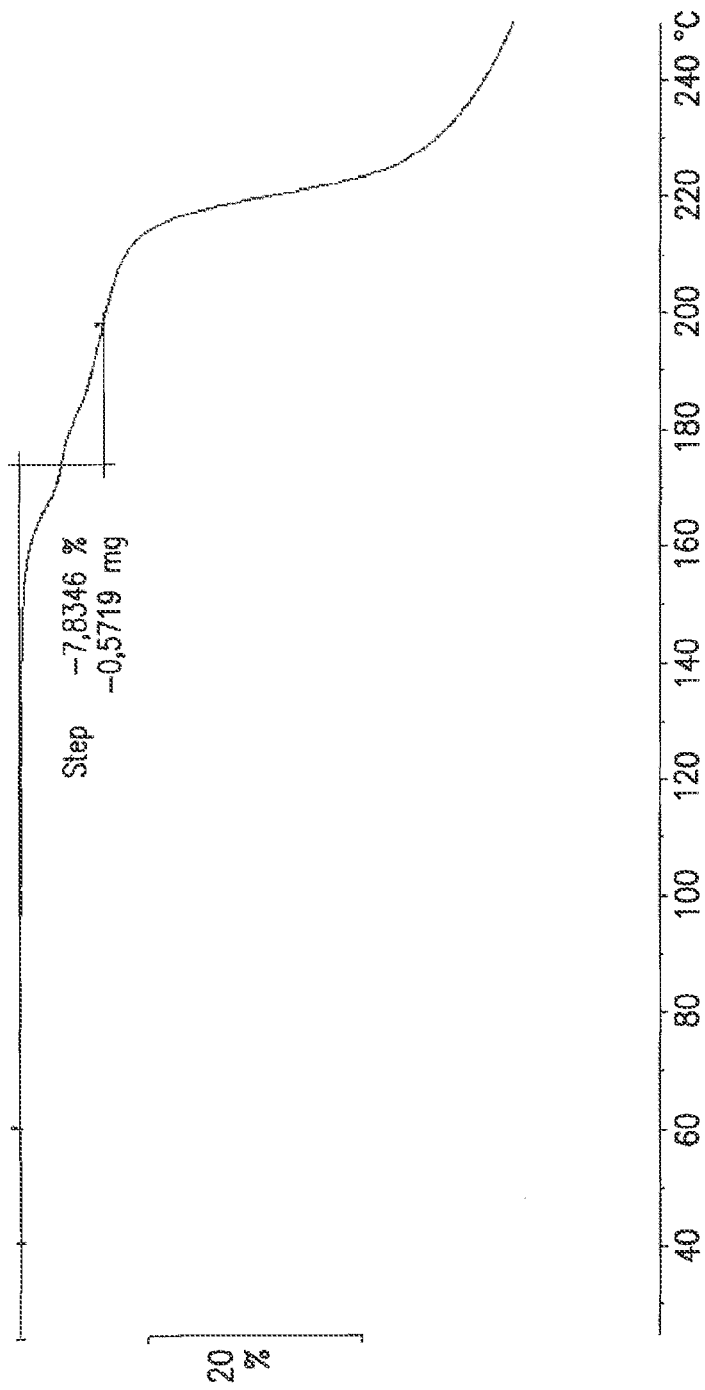
FIG. 18 shows a TGA thermogram for crystalline Cabazitaxel form XII.

Form XII can be further characterized by data selected from one or more of the following: a DSC thermogram substantially as depicted in FIG. 17; a DSC double peak having maxima at about 169.5±4° C. and 182.7±4° C. and a DSC melting onset at about 159.8±4° C.; a TGA thermogram substantially as depicted in FIG. 18; and by combinations of these data. The theoretical content of isobutanol for a monosolvate of cabazitaxel is about 8.1% w/w. For example, the content of the isobutanol can be about 7.8%±2 w/w as determined by TGA.

Form XII can be characterized by any combination of the above data.

Figure 19:
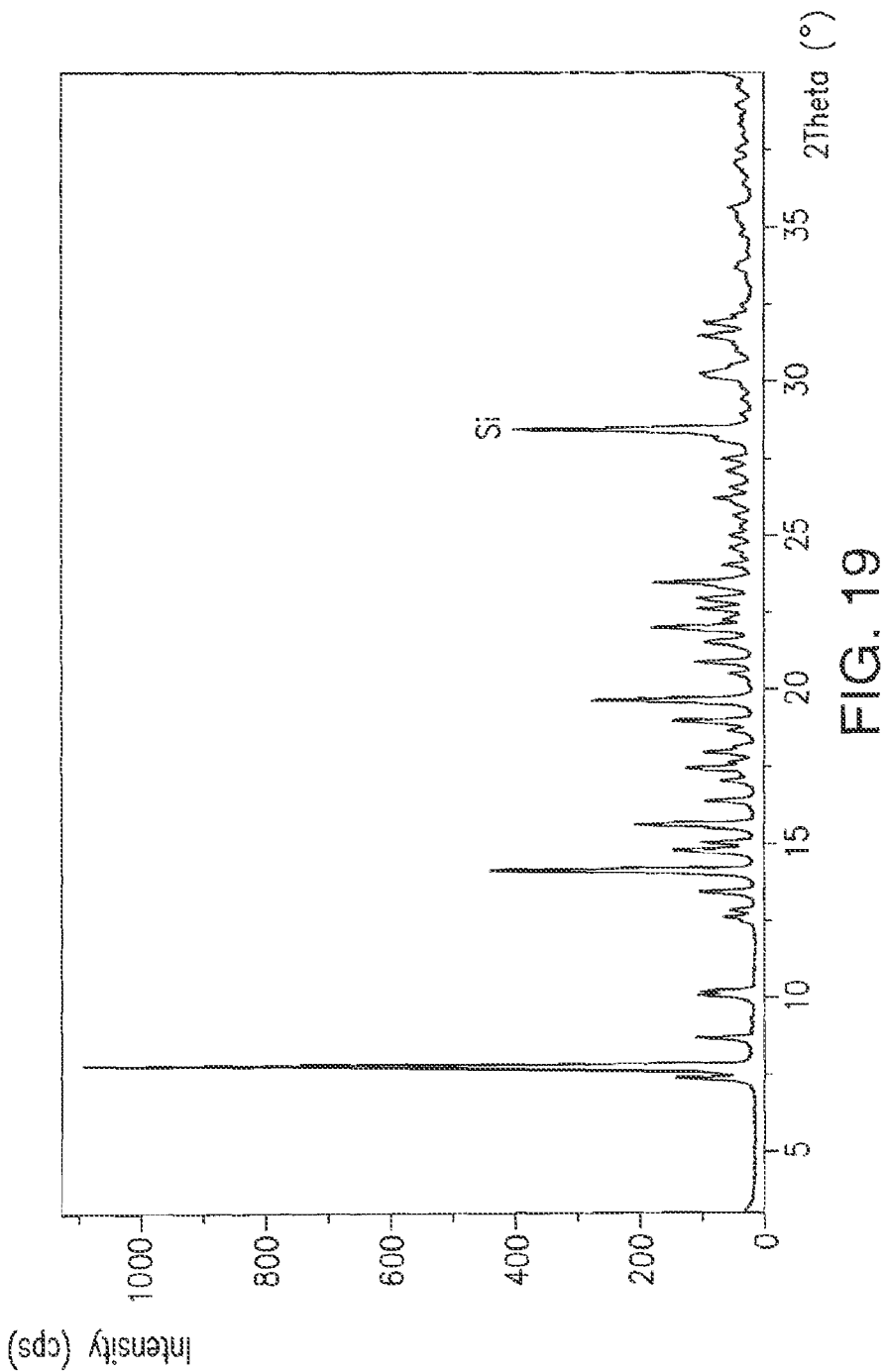
FIG. 19 shows a PXRD pattern for crystalline Cabazitaxel form XIII.

The present invention encompasses an amyl alcohol solvate of cabazitaxel. Particularly, the present invention encompasses a crystalline Cabazitaxel amyl alcohol solvate, designated as Form XIII. Form XIII can be characterized by data selected from one or more of the following: a powder X-ray diffraction pattern having peaks at 7.8, 10.1, 10.2, 13.4 and 14.4 degrees two theta±0.1 degrees two theta and also having no peak in the area from 10.5 to 12.1 degrees two theta; by a powder X-ray diffraction pattern substantially as depicted in FIG. 19; and by a combination of these data.

Form XIII, characterized by a powder X-ray diffraction pattern having peaks at 7.8, 10.1, 10.2, 13.4 and 14.4 degrees two theta±0.1 degrees two theta and also having no peak in the area from 10.5 to 12.1 degrees two theta, can be further characterized by an additional one, two, three, four or five PXRD peaks selected from 7.4, 8.7, 12.6, 15.6 and 19.7 degrees two theta±0.1) degrees two theta.

Figure 20:
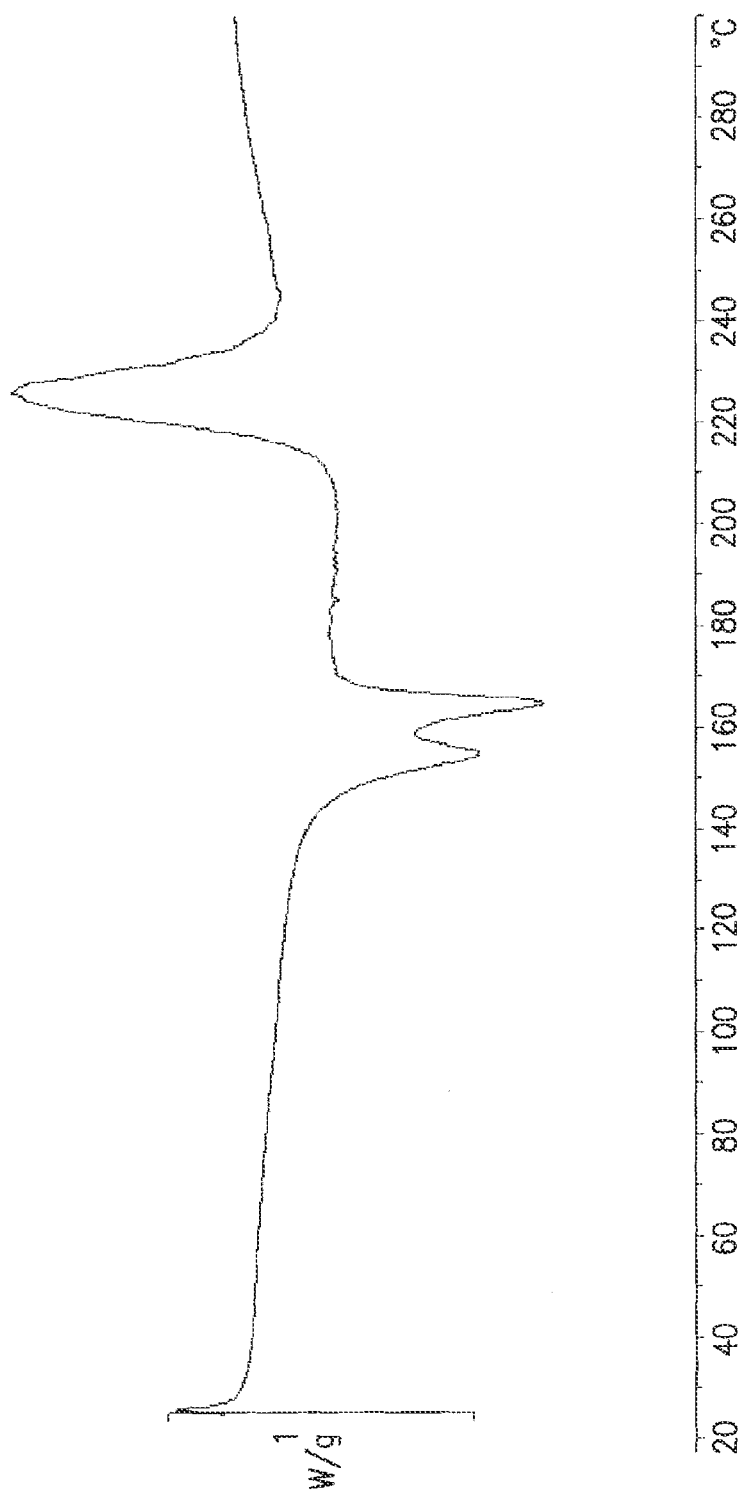
FIG. 20 shows a DSC thermogram for crystalline Cabazitaxel form XIII.
Figure 21:
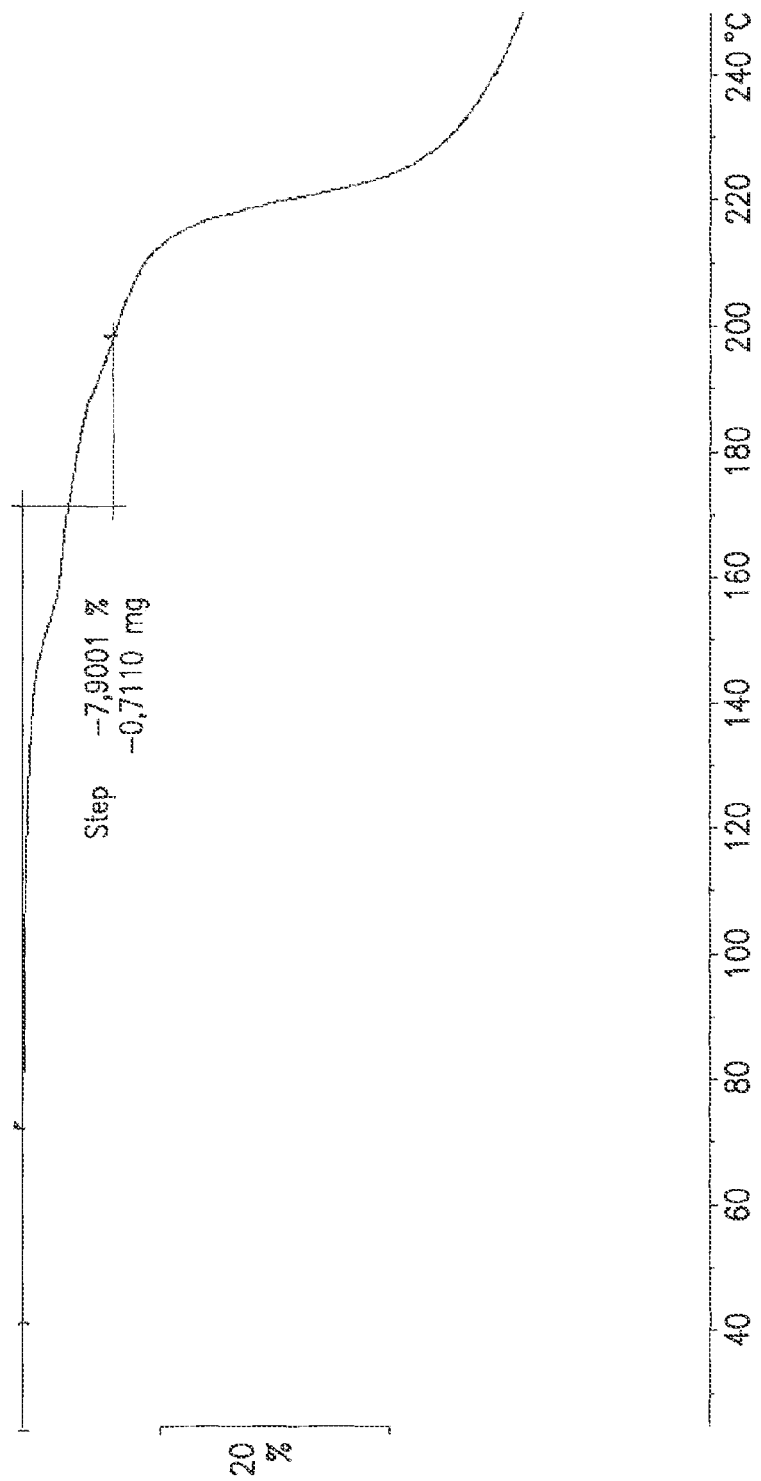
FIG. 21 shows a TGA thermogram for crystalline Cabazitaxel form XIII.

Form XIII can be further characterized by additional data selected from one or more of the following: a DSC thermogram substantially as depicted in FIG. 20; a DSC double peak having maxima at about 154.8±4° C. and 164.7±4° C. and a DSC melting onset at about 147.3±4° C.; a TGA thermogram substantially as depicted in FIG. 21; and by combinations of these data. The theoretical content of amyl alcohol for a monosolvate of cabazitaxel is about 9.5% w/w.

Form XIII can be characterized by any combination of the above data.

Figure 22:
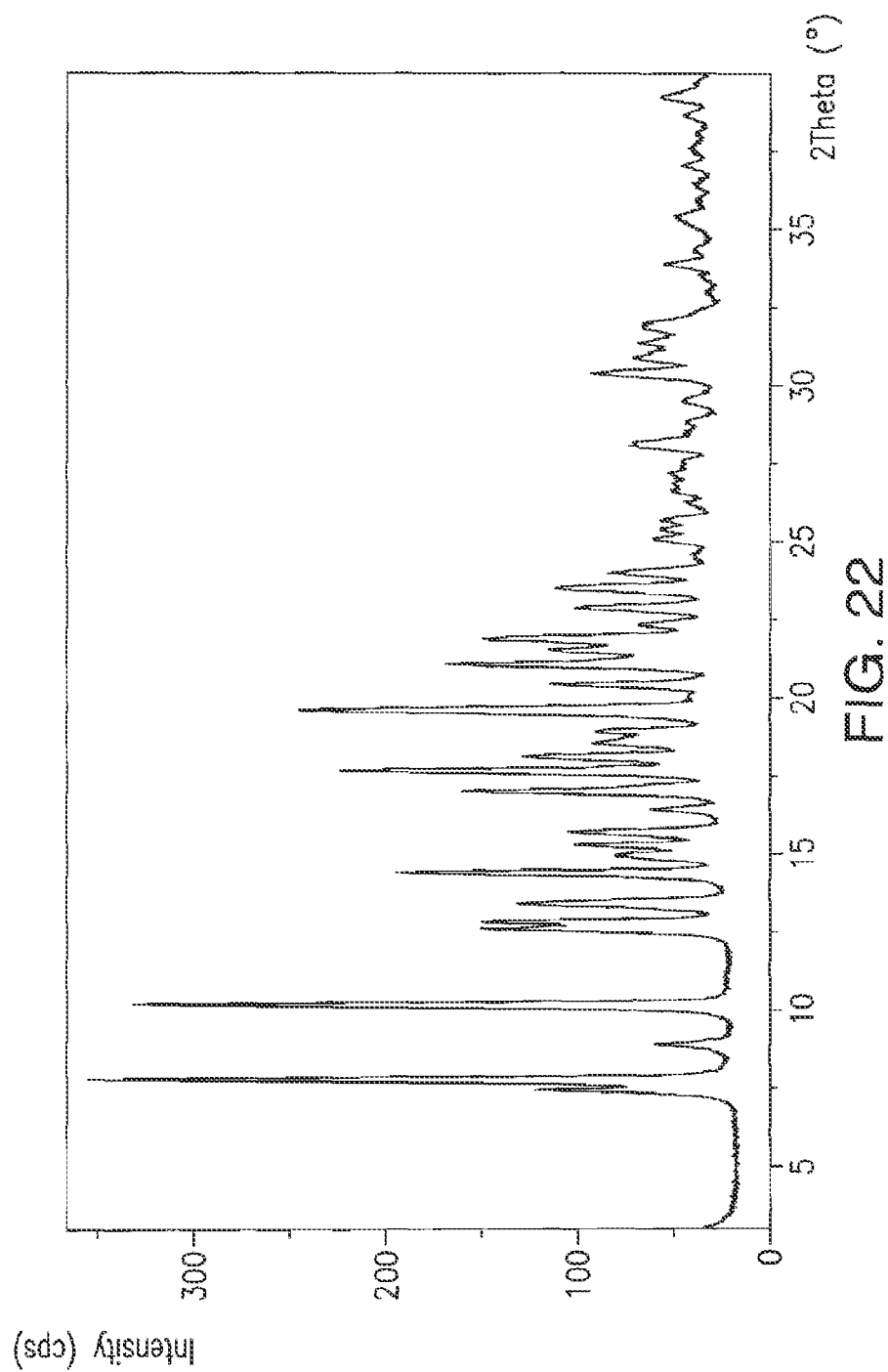
FIG. 22 shows a PXRD pattern for crystalline Cabazitaxel form XIV.

The present invention also encompasses a dioxolane solvate of cabazitaxel. Particularly, the present invention encompasses a crystalline Cabazitaxel dioxolane solvate, designated as Form XIV. Form XIV can be characterized by data selected from one or more of the following: a powder X-ray diffraction pattern having peaks at 7.8, 10.2, 12.6, 13.4 and 17.0 degrees two theta±0.1 degrees two theta and also having no peak in the area from 10.5 to 12.1 degrees two theta; by a powder X-ray diffraction pattern substantially as depicted in FIG. 22; and by a combination of these data.

Figure 23:
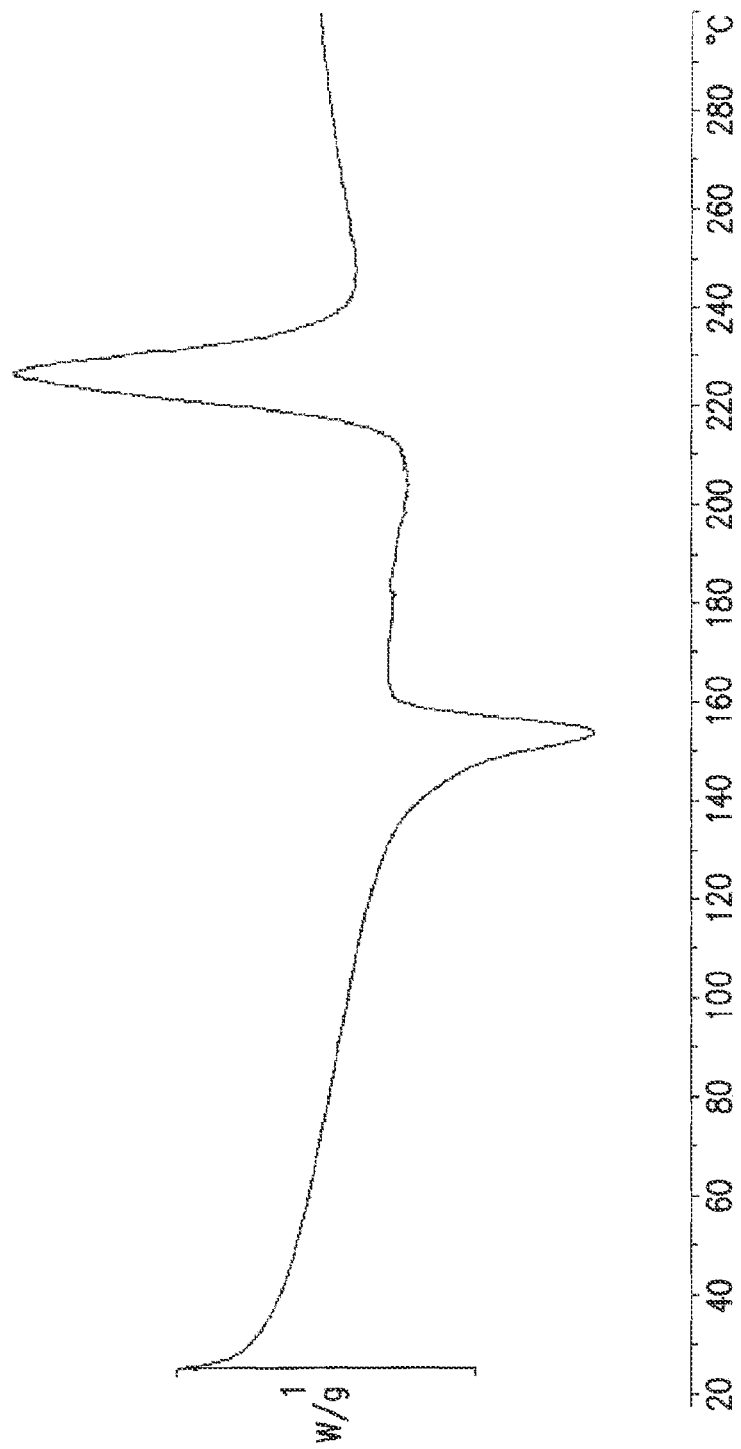
FIG. 23 shows a DSC thermogram for crystalline Cabazitaxel form XIV.
Figure 24:
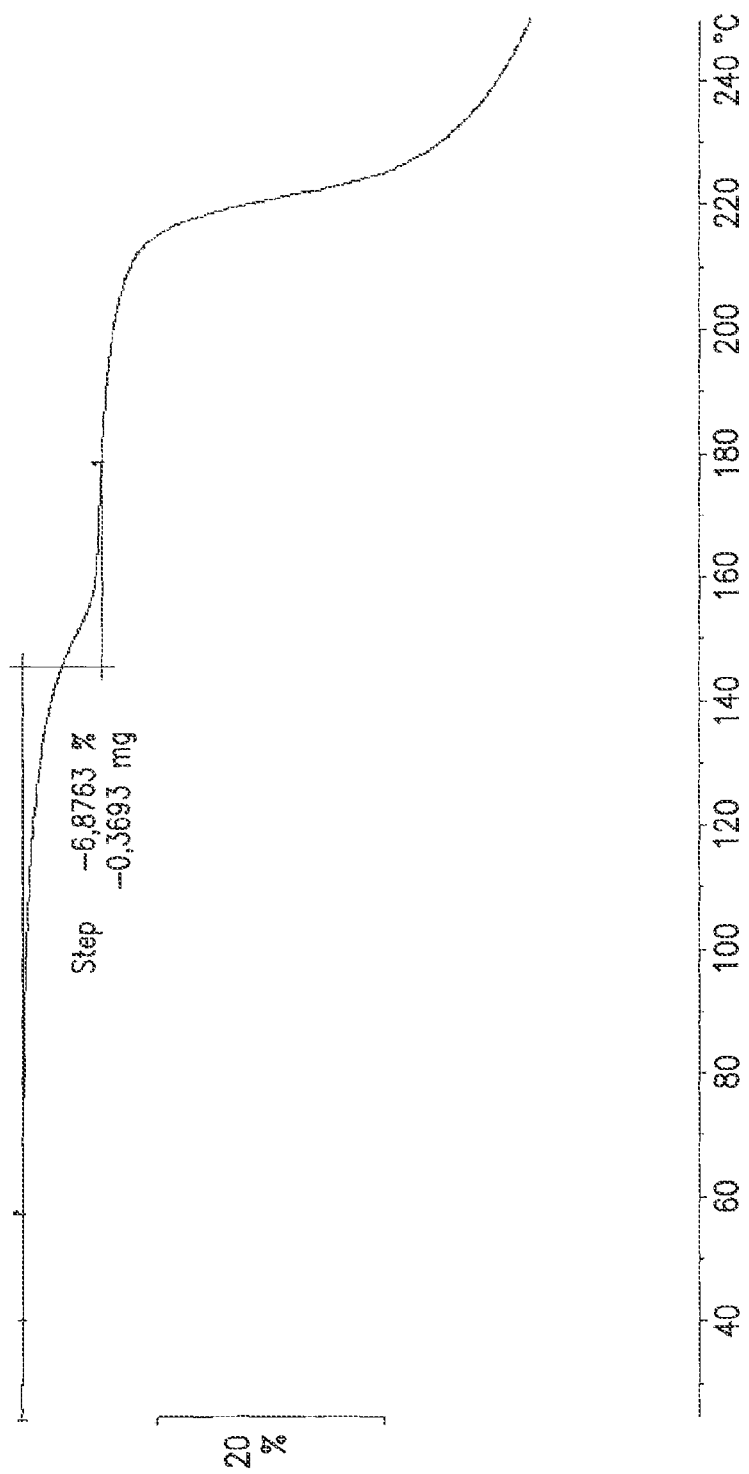
FIG. 24 shows a TGA thermogram for crystalline Cabazitaxel form XIV.

Form XIV, characterized by a powder X-ray diffraction pattern having peaks at 7.8, 10.2, 12.6, 13.4 and 17.0 degrees two theta±0.1 degrees two theta and also having no peak in the area from 10.5 to 12.1 degrees two theta, can be further characterized by an additional one, two, three, four or five PXRD peaks selected from 7.5, 8.9, 12.8, 17.7 and 19.6 degrees two theta±0.1 degrees two theta Form XIV can be further characterized by data selected from one or more of the following: a DSC thermogram substantially as depicted in FIG. 23; a DSC melting peak at about 153.7±4° C. and a DSC melting onset at about 144.0±4° C.; a TGA thermogram substantially as depicted in FIG. 24; and by combinations of these data. The theoretical content of isobutanol for a monosolvate of cabazitaxel is about 8.1% w/w. For example, the content of the isobutanol can be about 6.9%±2 w/w as determined by TGA.

Form XIV can be characterized by any combination of the above data.

Figure 25:
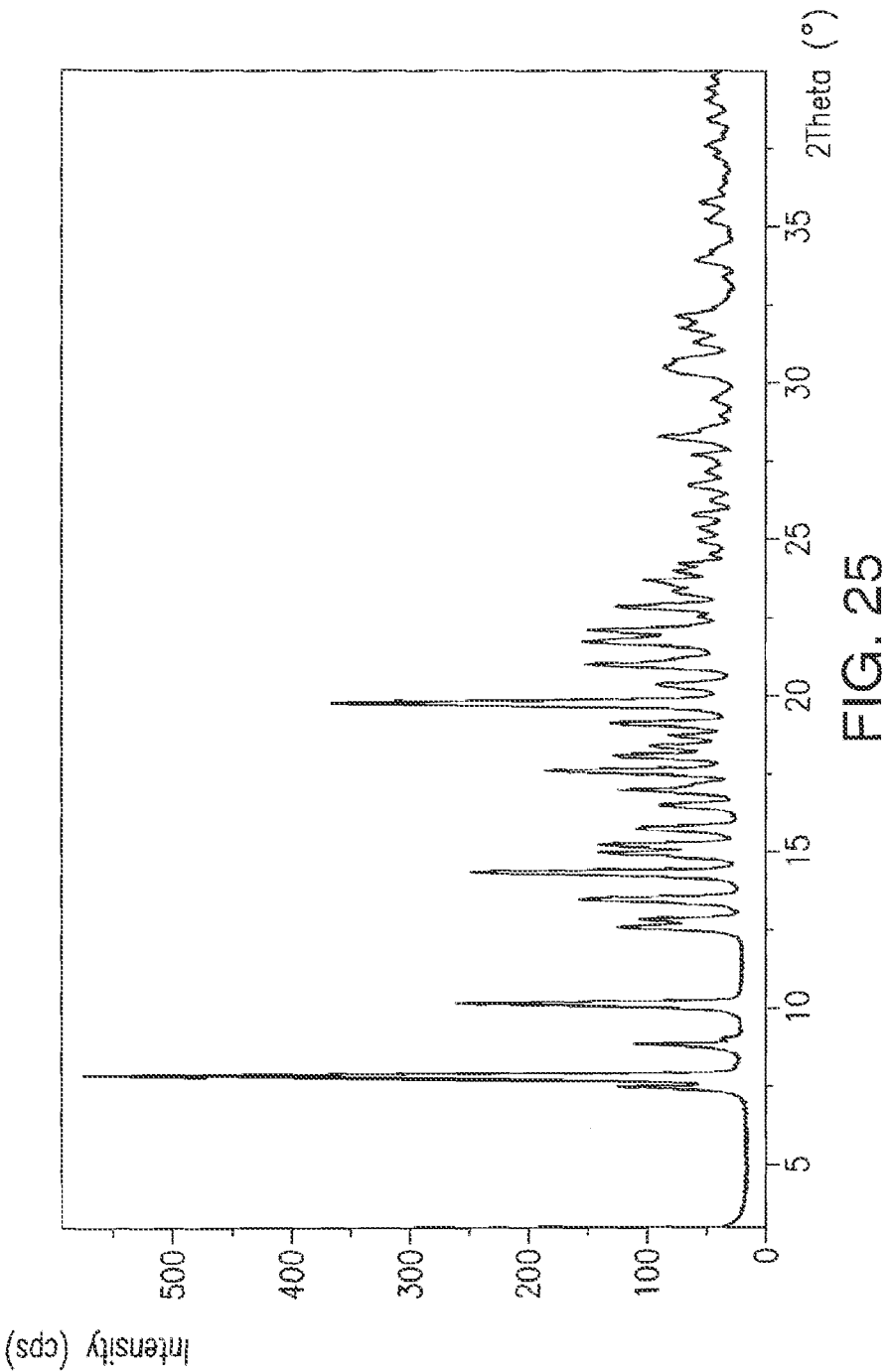
FIG. 25 shows a PXRD pattern for crystalline Cabazitaxel form XV.

The present invention also encompasses a 1,4-dioxane solvate of cabazitaxel. Particularly, the present invention encompasses a crystalline Cabazitaxel 1,4-dioxane designated as Form XV. Form XV can be characterized by data selected from one or more of the following: a powder X-ray diffraction pattern having peaks at 7.8, 10.1, 12.6, 13.5 and 14.3 degrees two theta±0.1 degrees two theta and also having no peak in the area from 10.5 to 12.1 degrees two theta; by a powder X-ray diffraction pattern substantially as depicted in FIG. 25, and by a combination of these data.

Form XV, characterized by a powder X-ray diffraction pattern having peaks at 7.8, 10.1, 12.6, 13.5 and 14.3 degrees two theta±0.1 degrees two theta and also having no peak in the area from 10.5 to 12.1 degrees two theta, can be further characterized by an additional one, two, three, four or five PXRD peaks selected from 7.4, 8.8, 12.8, 14.9 and 15.2 degrees two theta±0.1 degrees two theta.

Figure 26:
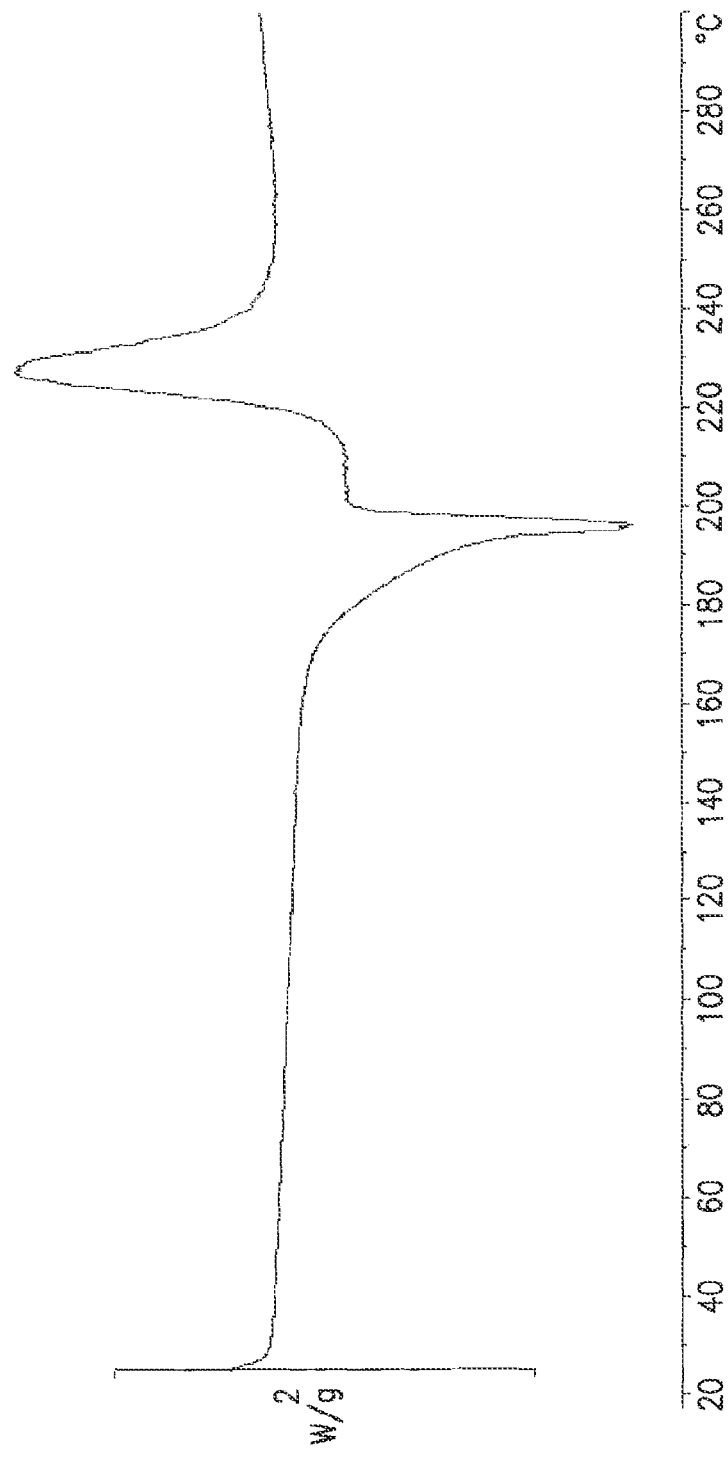
FIG. 26 shows a DSC thermogram for crystalline Cabazitaxel form XV.
Figure 27:
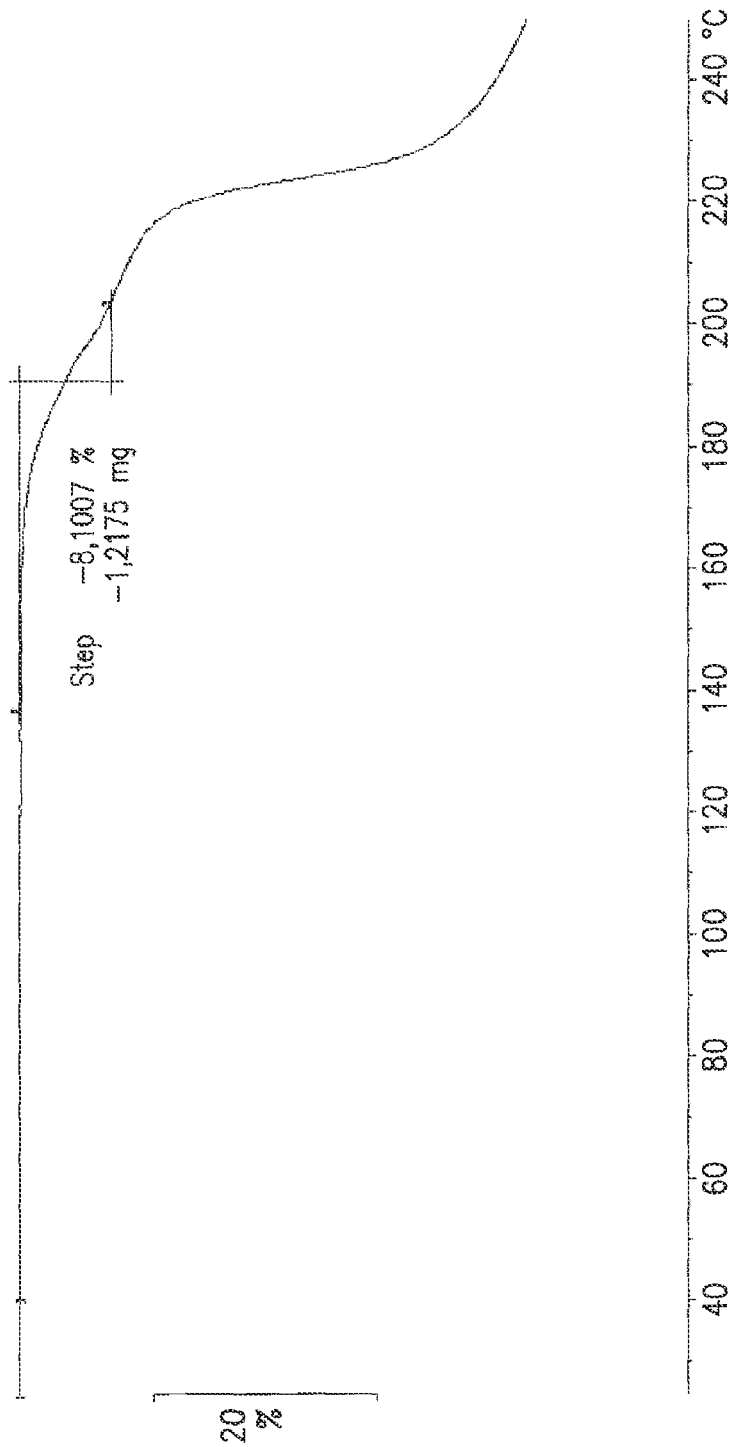
FIG. 27 shows a TGA thermogram for crystalline Cabazitaxel form XV.

Form XV can be further characterized by data selected from one or more of the following: a DSC thermogram substantially as depicted in FIG. 26; a DSC melting peak at about 195.4±4° C. and a DSC melting onset at about 191.8±4° C.; a TGA thermogram substantially as depicted in FIG. 27; and by combinations of these data. The theoretical content of 1,4-dioxane for a monosolvate of cabazitaxel is about 9.5% w/w. For example, the content of the 1,4-dioxane can be about 8.1%±2 w/w as determined by TGA.

Form XV can be characterized by any combination of the above data.

Figure 28:
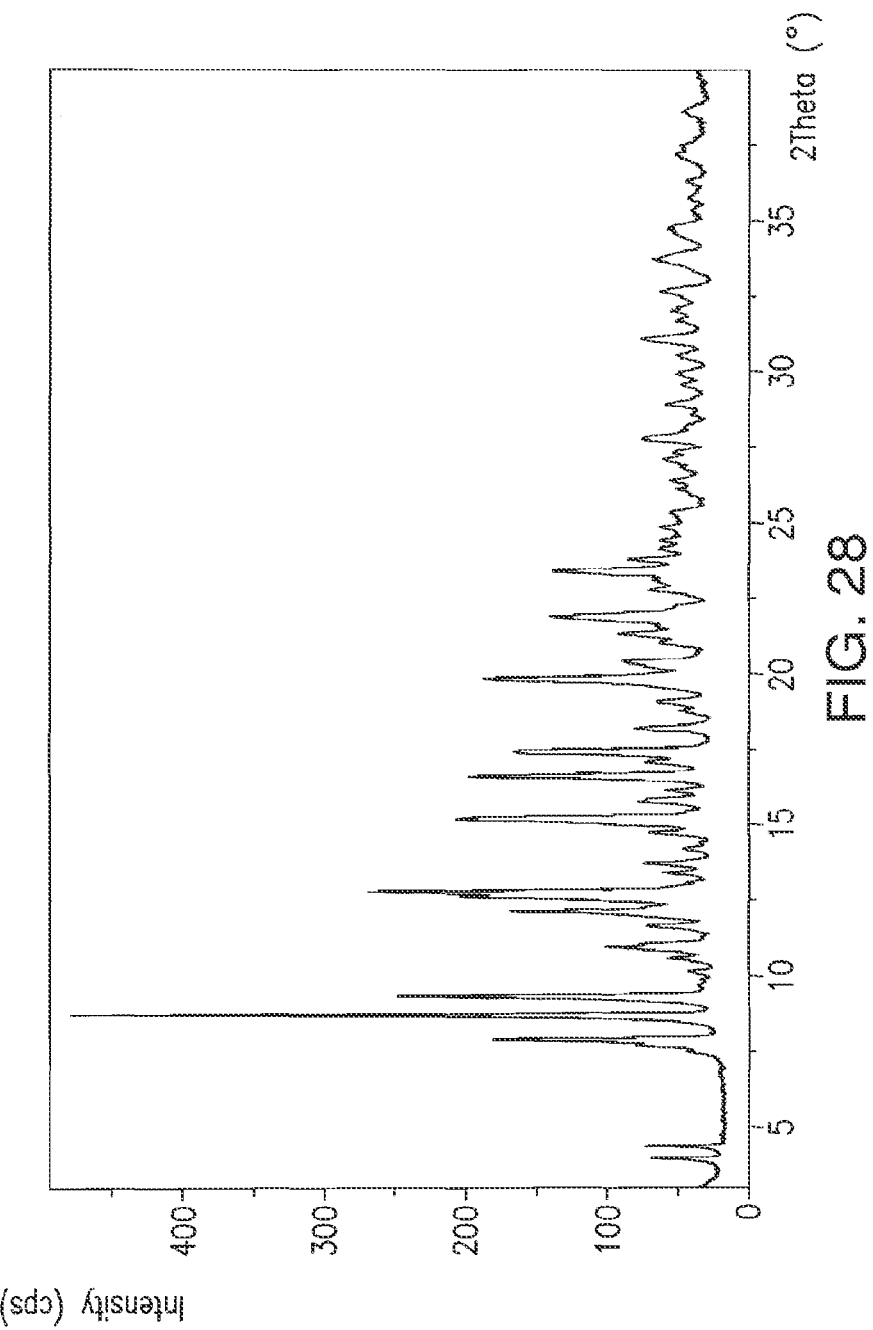
FIG. 28 shows a PXRD pattern for crystalline Cabazitaxel form XVI.

In another embodiment the present invention encompasses a crystalline Cabazitaxel designated as Form XVI. Form XVI can be characterized by data selected from one or more of the following: a powder X-ray diffraction pattern having peaks at 4.0, 4.4, 9.3, 11.6 and 14.7 degrees two theta±0.1 degrees two theta; by a powder X-ray diffraction pattern substantially as depicted in FIG. 28; and by a combination of these data.

Form XVI, characterized by a powder X-ray diffraction pattern having peaks at 4.0, 4.4, 9.3, 11.6 and 14.7 degrees two theta±0.1 degrees two theta, can be further characterized by an additional one, two, three, four or five PXRD peaks selected from 7.5, 7.7, 12.6, 12.8 and 13.7 degrees two theta±0.1 degrees two theta.

Figure 29:
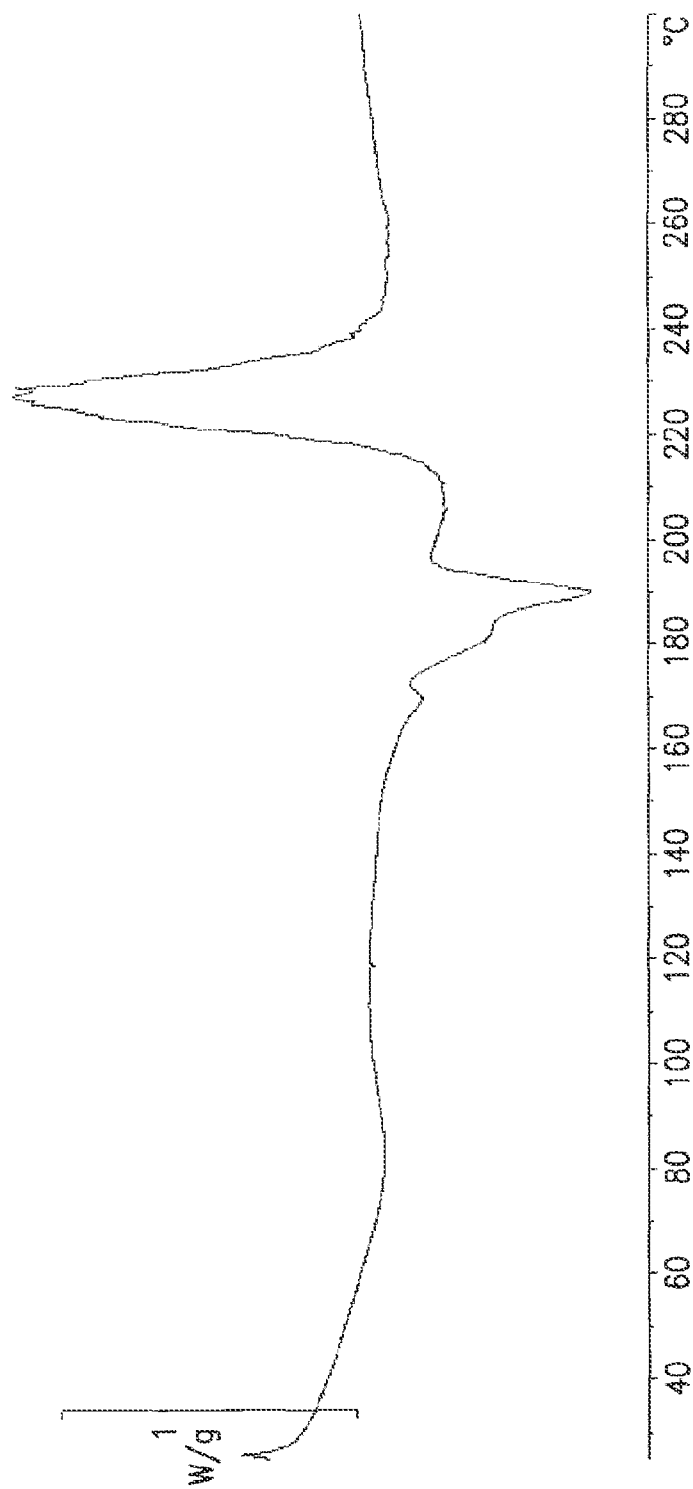
FIG. 29 shows a DSC thermogram for crystalline Cabazitaxel form XVI.
Figure 30:
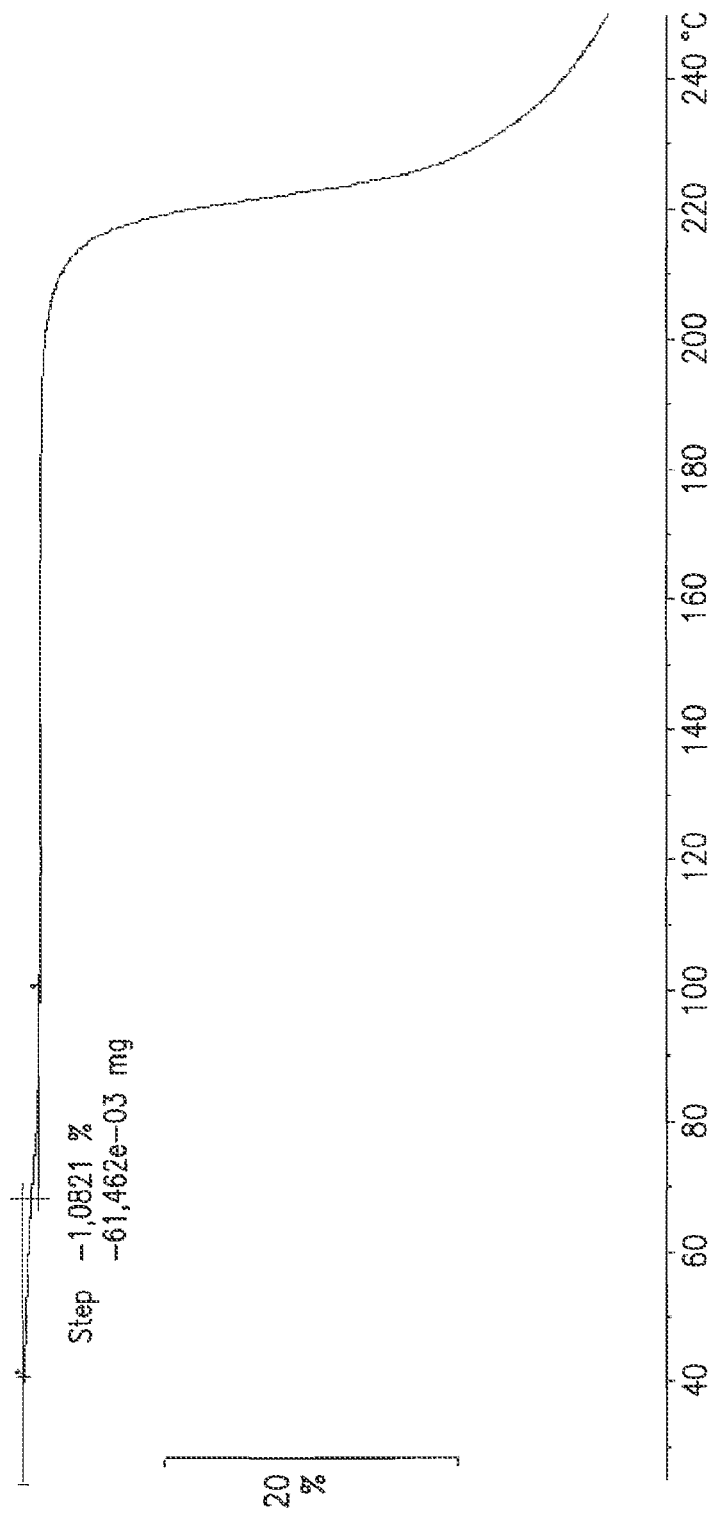
FIG. 30 shows a TGA thermogram for crystalline Cabazitaxel form XVI.

Form XVI can be further characterized by data selected from one or more of the following: a DSC thermogram substantially as depicted in FIG. 29; a DSC melting peak at about 189.7±4° C. and a DSC melting onset at about 183.0±4° C.; a TGA thermogram substantially as depicted in FIG. 30; and by combinations of these data.

Form XVI can be characterized by any combination of the above data.

The above form XVI can be anhydrous form.

The present invention also encompasses a methyl acetate solvate of cabazitaxel.

Figure 37:
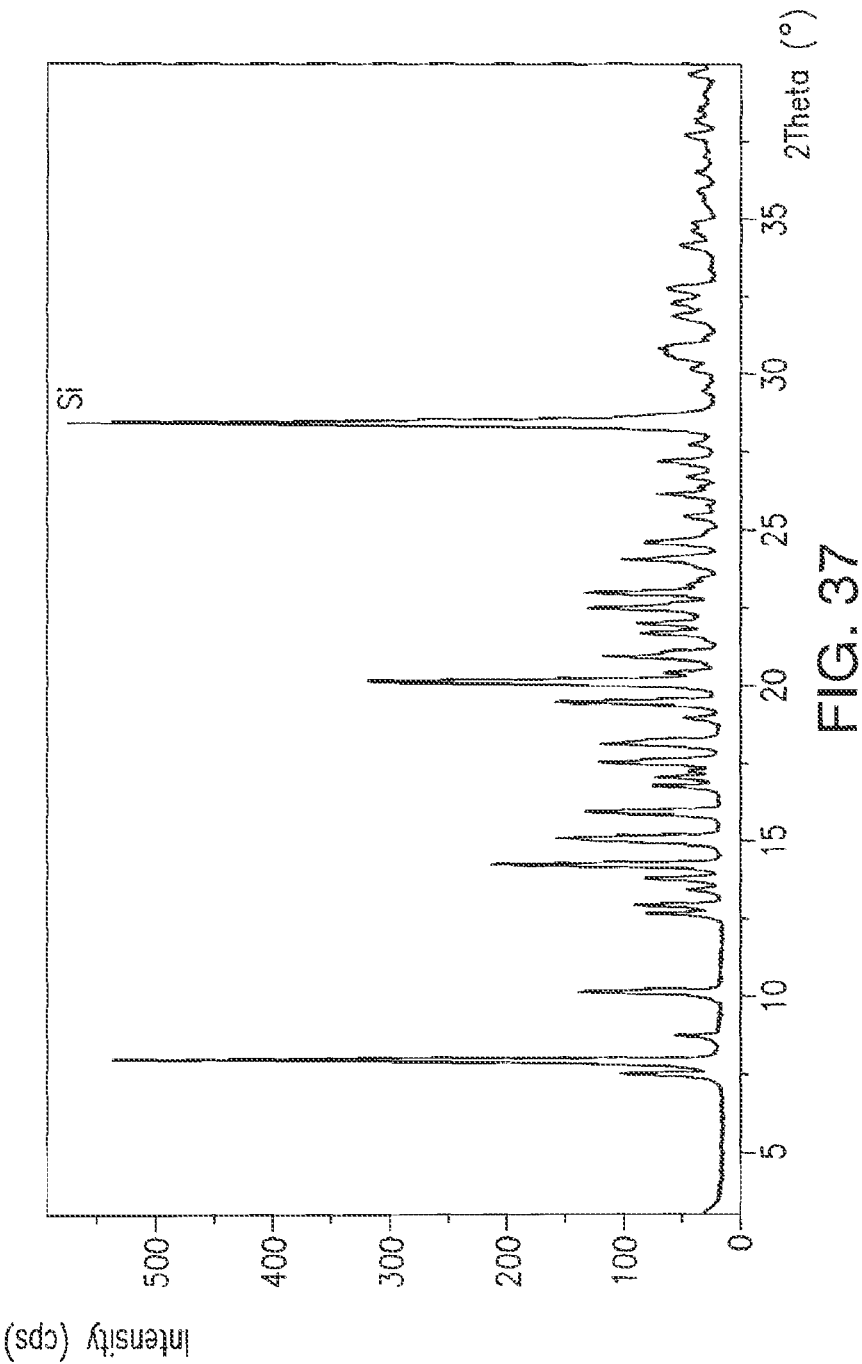
FIG. 37 shows a PXRD pattern for crystalline Cabazitaxel form XVII.

Particularly, the present invention encompasses a crystalline Cabazitaxel methyl acetate designated as Form XVII. Form XVII can be characterized by data selected from one or more of the following: a powder X-ray diffraction pattern having peaks at 8.0, 8.7, 14.2, 15.1 and 15.9 degrees two theta±0.1 degrees two theta; by a powder X-ray diffraction pattern substantially as depicted in FIG. 37, and by a combination of these data.

Form XVII, characterized by a powder X-ray diffraction pattern having peaks at 8.0, 8.7, 14.2, 15.1 and 15.9 degrees two theta±0.1 degrees two theta, can be further characterized by a powder X-ray diffraction pattern having no peak in the area from 10.5 to 12.1 degrees two theta.

Form XVII, characterized by a powder X-ray diffraction pattern having peaks at 8.0, 8.7, 14.2, 15.1 and 15.9 degrees two theta±0.1 degrees two theta, can be further characterized by an additional one, two, three, four or five PXRD peaks selected from 7.5, 10.1, 12.6, 12.9 and 20.1 degrees two theta±0.1 degrees two theta.

Figure 38:
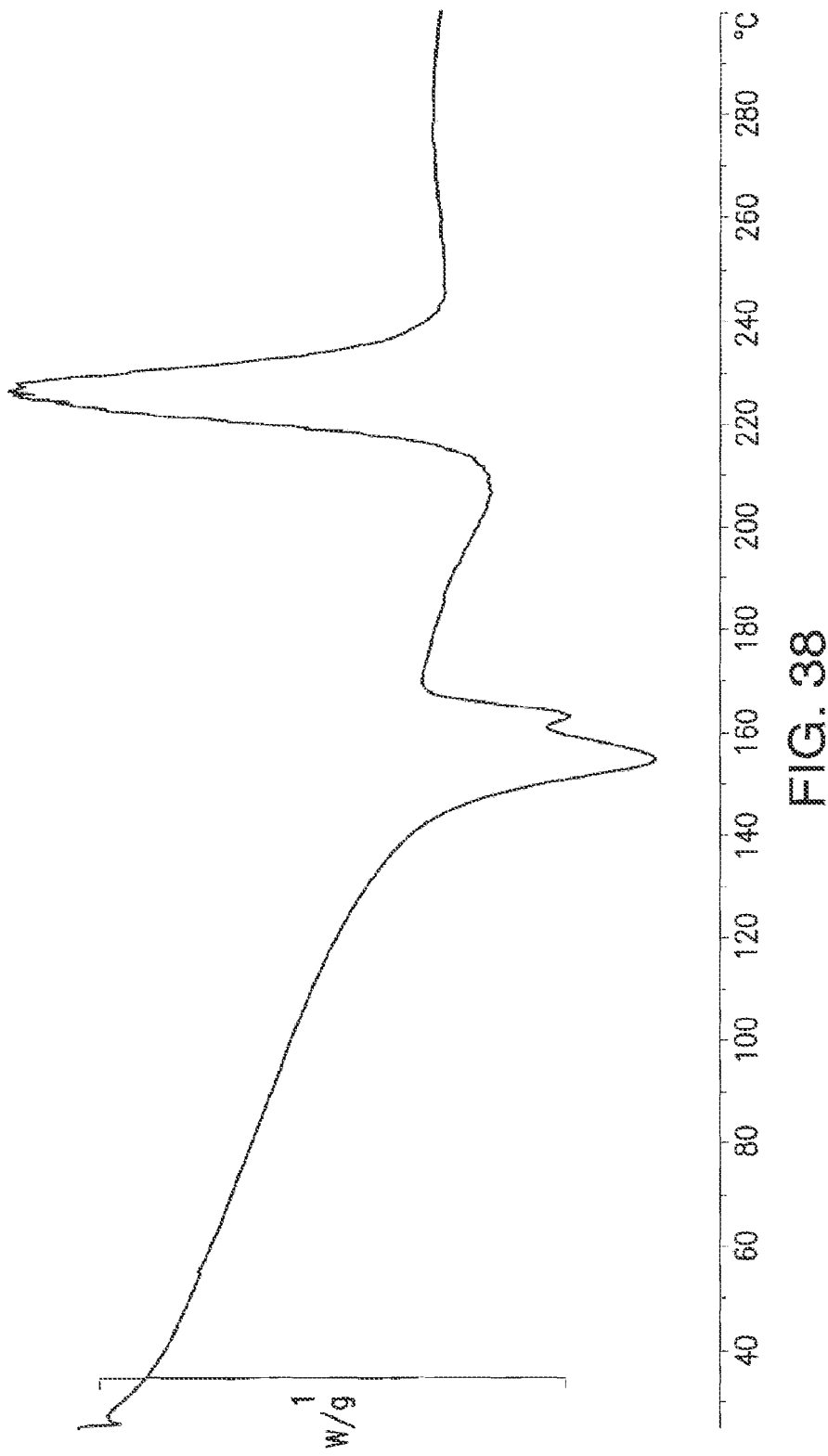
FIG. 38 shows a DSC thermogram for crystalline Cabazitaxel form XVII.
Figure 39:
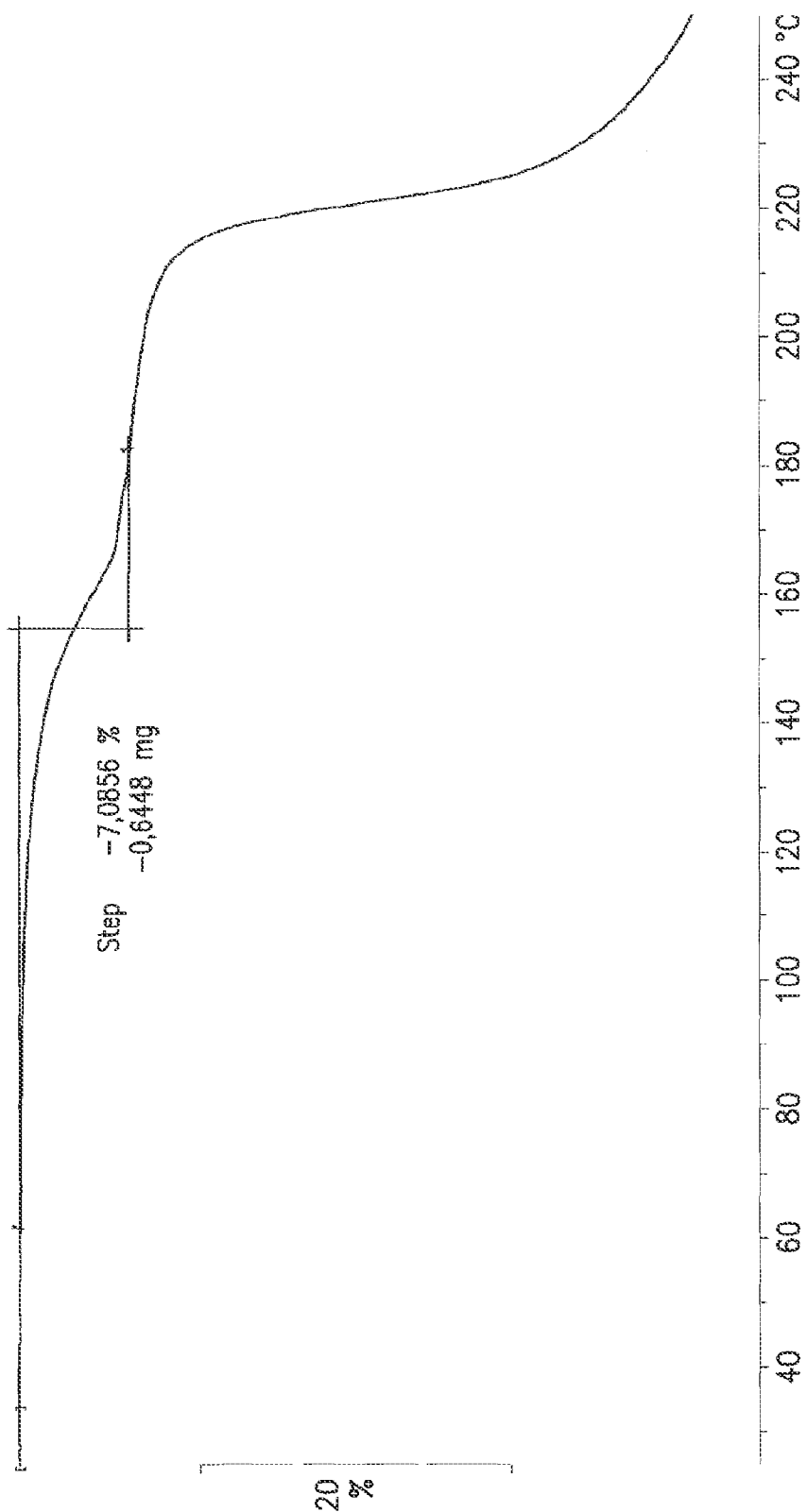
FIG. 39 shows a TGA thermogram for crystalline Cabazitaxel form XVII.

Form XVII can be further characterized by data selected from one or more of the following: a DSC thermogram substantially as depicted in FIG. 38; a DSC melting double peak at about 154.9±4° C. and 163.1±4° C.; a DSC melting onset at about 143.2±4° C.; a TGA thermogram substantially as depicted in FIG. 39; and by combinations of these data. The theoretical content of methyl acetate for a monosolvate of cabazitaxel is about 8.1% w/w. For example, the content of the methyl acetate can be about 7.1%±2 w/w as determined by TGA.

Form XVII can be characterized by any combination of the above data.

Figure 40:
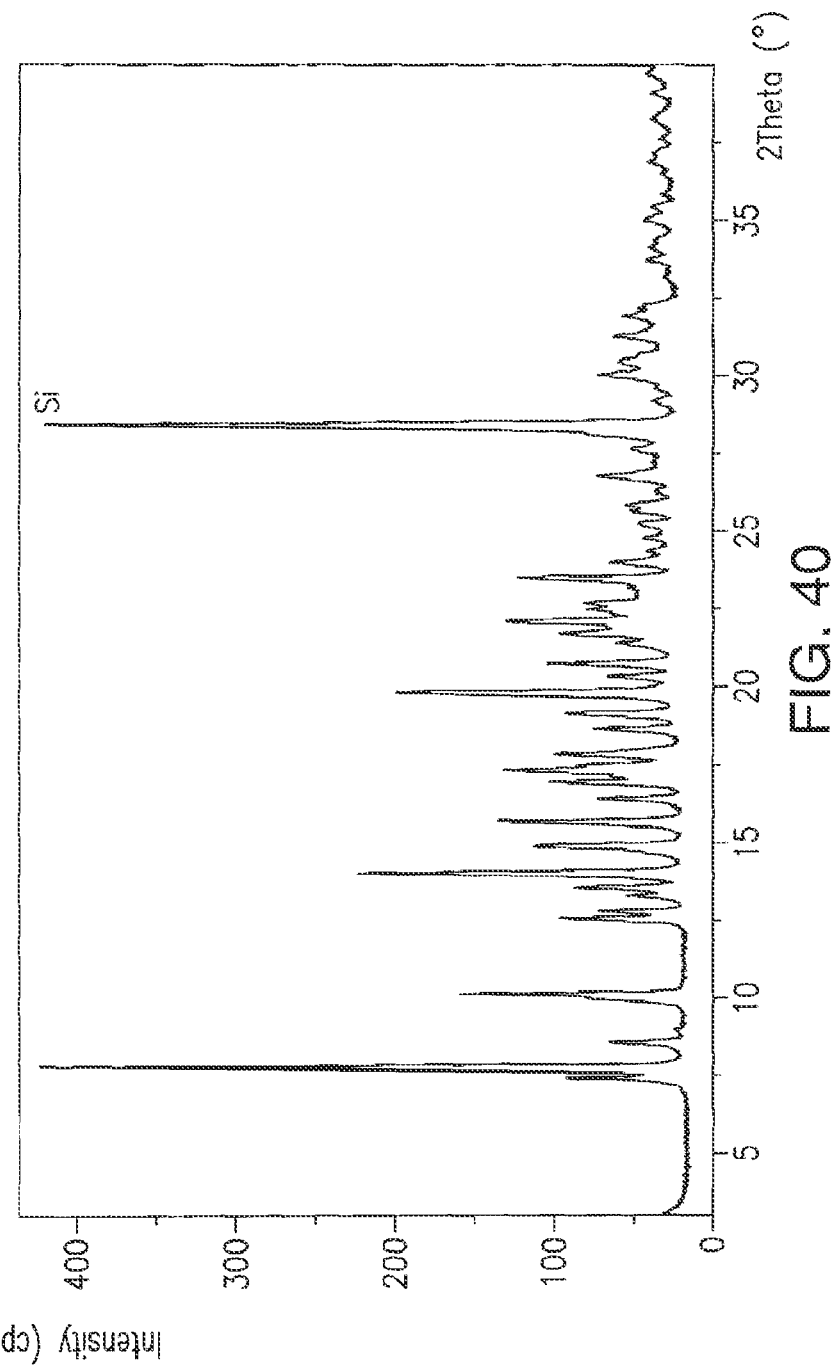
FIG. 40 shows a PXRD pattern for crystalline Cabazitaxel form XVIII.

The present invention also encompasses a butyl acetate solvate of cabazitaxel. Particularly, the present invention encompasses crystalline Cabazitaxel butyl acetate designated as Form XVIII. Form XVIII can be characterized by data selected from one or more of the following: a powder X-ray diffraction pattern having peaks at 8.6, 13.6, 14.0, 19.2 and 19.8 degrees two theta±0.1 degrees two theta; by a powder X-ray diffraction pattern substantially as depicted in FIG. 40, and by a combination of these data.

Form XVIII, characterized by a powder X-ray diffraction pattern having peaks at 8.6, 13.6, 14.0, 19.2 and 19.8 degrees two theta±0.1 degrees two theta, can be further characterized by a powder X-ray diffraction pattern having no peak in the area from 10.5 to 12.1 degrees two theta.

Form XVIII, characterized by a powder X-ray diffraction pattern having peaks at 8.6, 13.6, 14.0, 19.2 and 19.8 degrees two theta±0.1 degrees two theta, can be further characterized by an additional one, two, three, four or five PXRD peaks selected from 7.5, 7.8, 10.2, 14.9 and 15.7 degrees two theta±0.1 degrees two theta.

Figure 41:
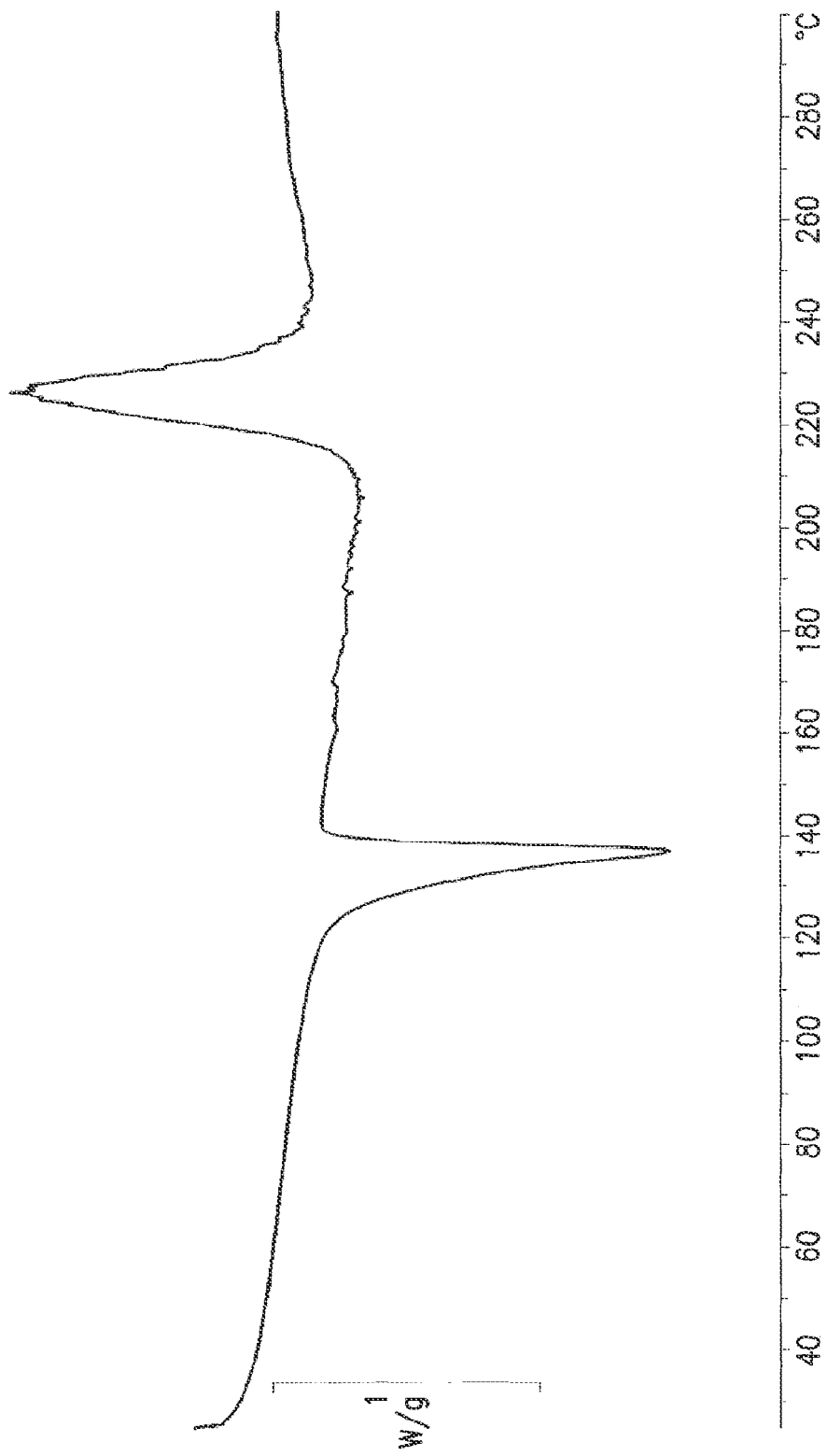
FIG. 41 shows a DSC thermogram for crystalline Cabazitaxel form XVIII.
Figure 42:
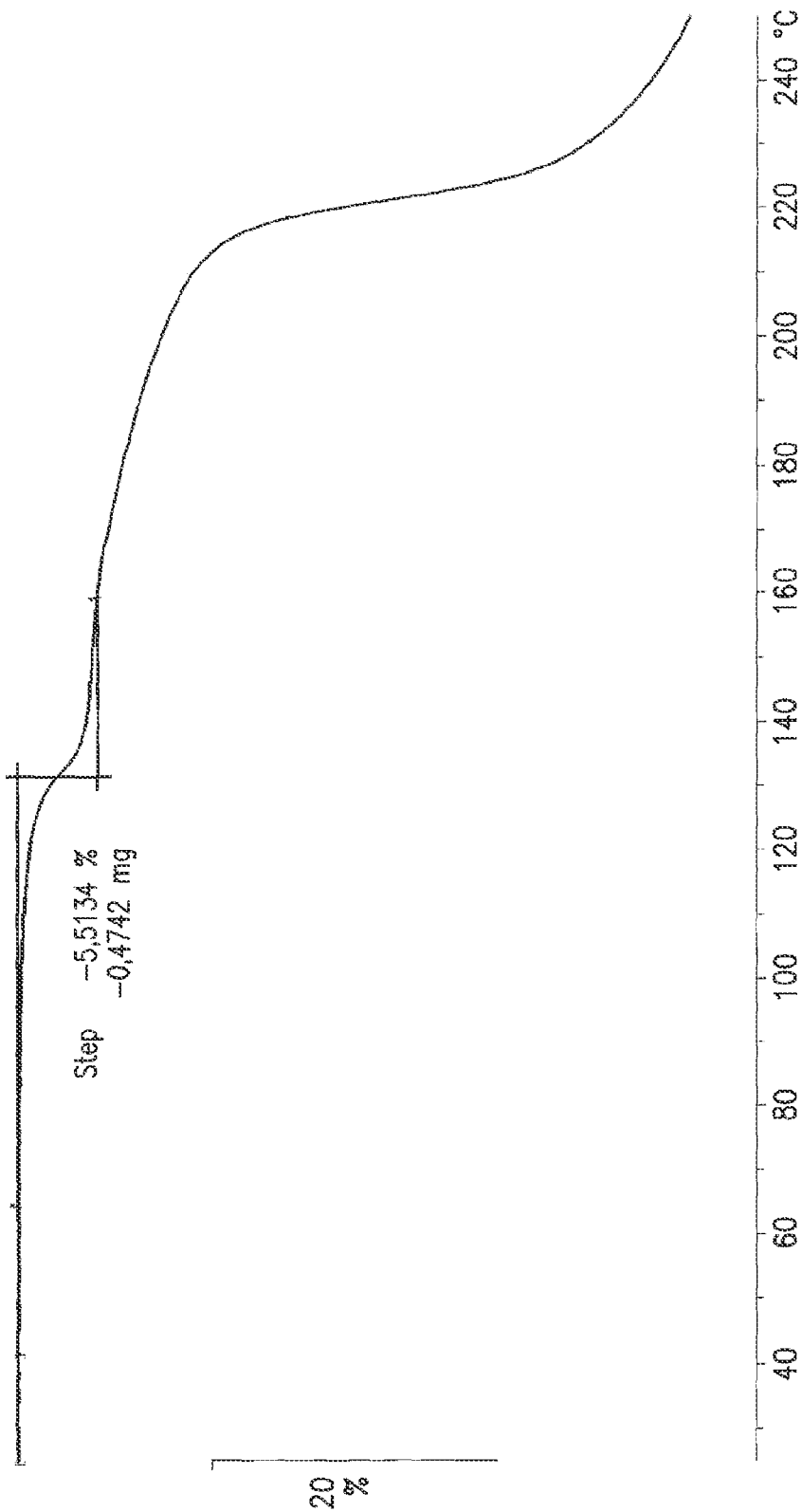
FIG. 42 shows a TGA thermogram for crystalline Cabazitaxel form XVIII.

Form XVIII can be further characterized by data selected from one or more of the following: a DSC thermogram substantially as depicted in FIG. 41; a DSC melting peak at about 136.6±4° C.; a DSC melting onset at about 130.1±4° C.; a TGA thermogram substantially as depicted in FIG. 42; and by combinations of these data. The theoretical content of butyl acetate for a monosolvate of cabazitaxel is about 12.2% w/w. For example, the content of the butyl acetate can be about 5.5%±2 w/w as determined by TGA.

Form XVIII can be characterized by any combination of the above data.

Figure 43:
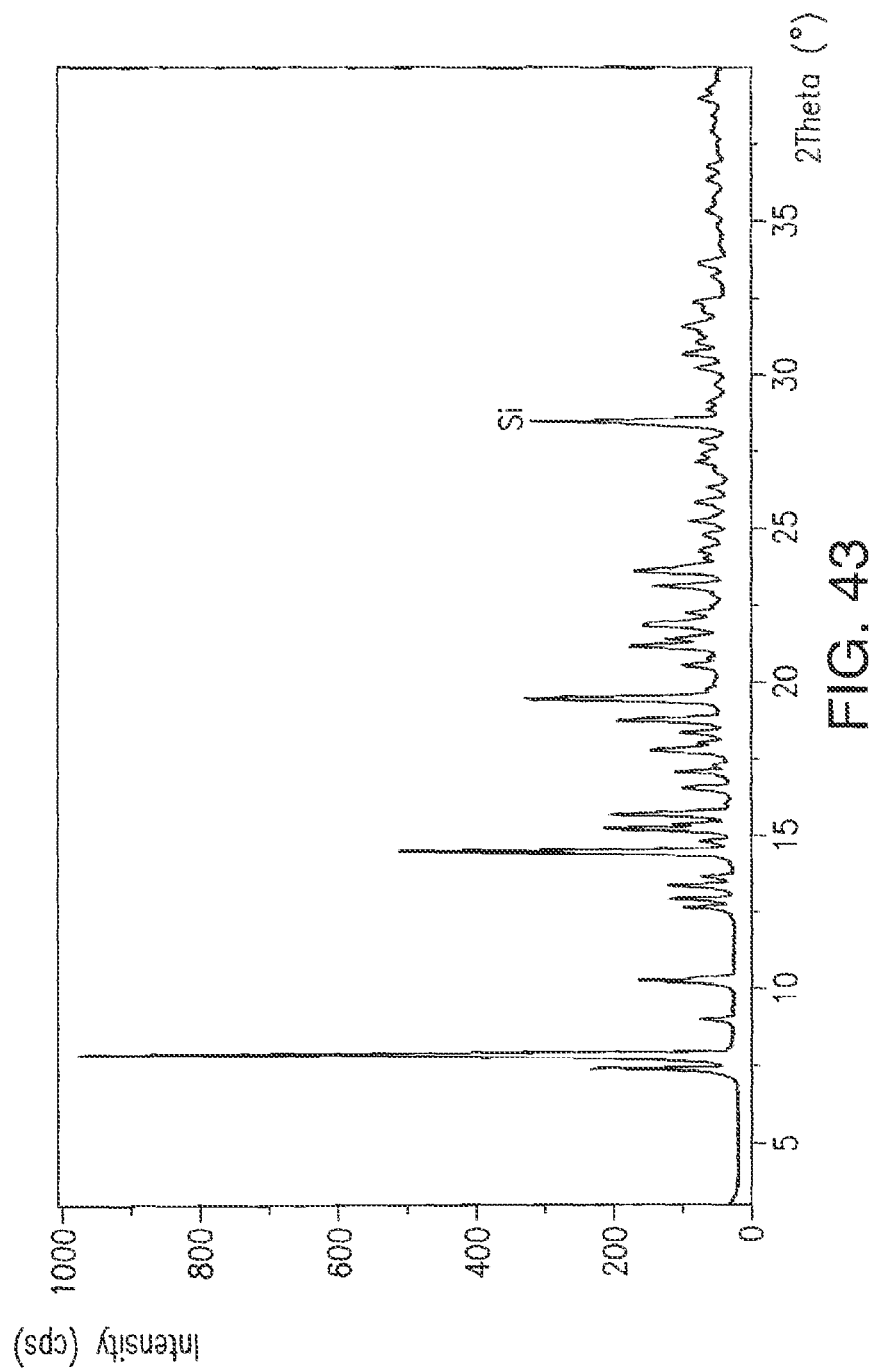
FIG. 43 shows a PXRD pattern for crystalline Cabazitaxel form XIX.

The present invention also encompasses a 1,2-propanediol solvate of cabazitaxel. Particularly, the present invention encompasses crystalline Cabazitaxel 1,2-propanediol designated as Form XIX. Form XIX can be characterized by data selected from one or more of the following: a powder X-ray diffraction pattern having peaks at 9.0, 14.5, 15.2, 15.7 and 16.5 degrees two theta±0.1 degrees two theta; by a powder X-ray diffraction pattern substantially as depicted in FIG. 43, and by a combination of these data.

Form XIX, characterized by a powder X-ray diffraction pattern having peaks at 9.0, 14.5, 15.2, 15.7 and 16.5 degrees two theta±0.1 degrees two theta, can be further characterized by a powder X-ray diffraction pattern having no peak in the area from 10.5 to 12.1 degrees two theta.

Form XIX, characterized by a powder X-ray diffraction pattern having peaks at 9.0, 14.5, 15.2, 15.7 and 16.5 degrees two theta±0.1 degrees two theta, can be further characterized by an additional one, two, three, four or five PXRD peaks selected from 7.4, 7.9, 10.3, 12.9 and 13.3 degrees two theta±0.1 degrees two theta.

Figure 44:
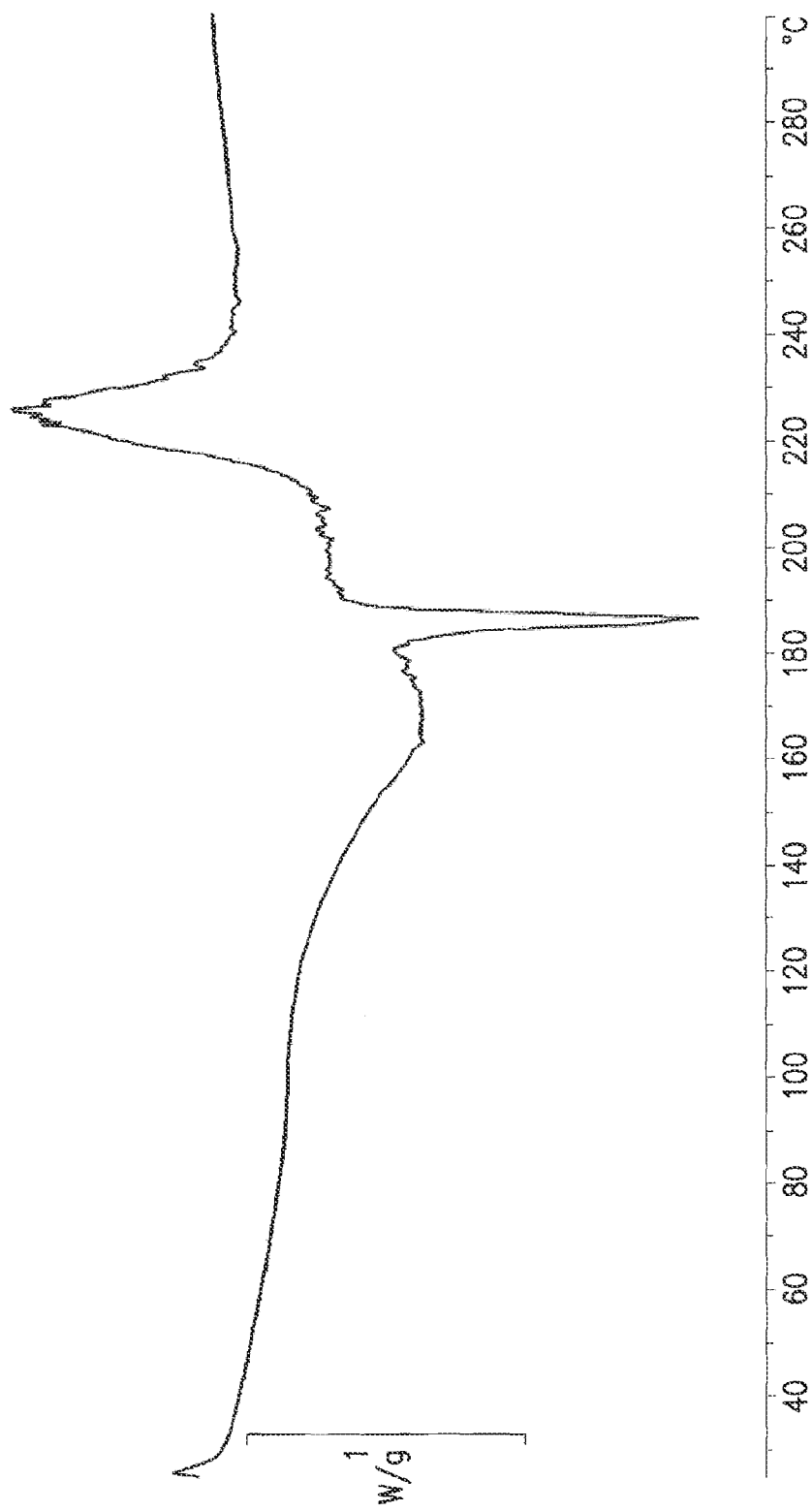
FIG. 44 shows a DSC thermogram for crystalline Cabazitaxel form XIX.
Figure 45:
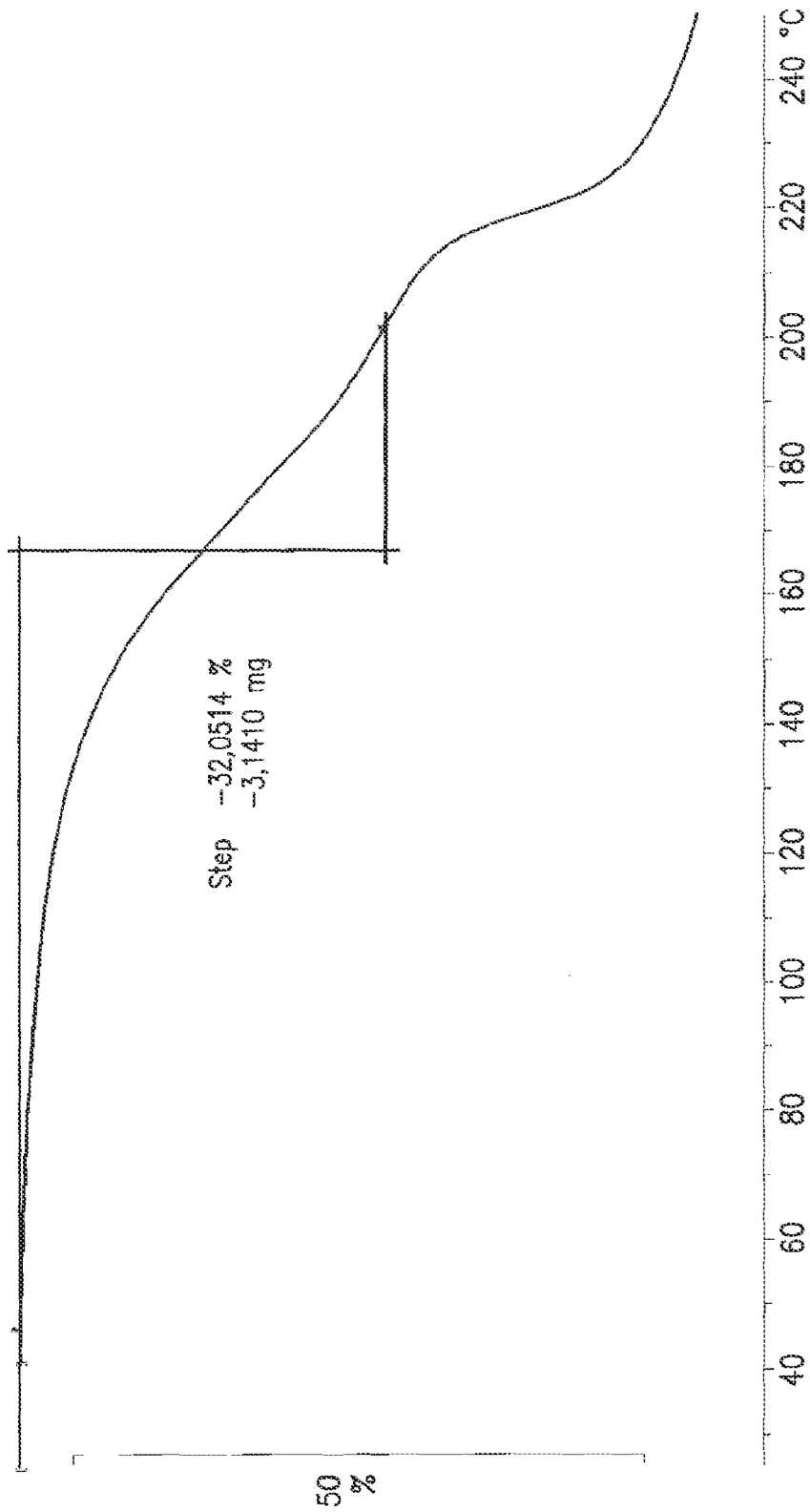
FIG. 45 shows a TGA thermogram for crystalline Cabazitaxel form XIX.

Form XIX can be further characterized by data selected from one or more of the following: a DSC thermogram substantially as depicted in FIG. 44; a DSC melting peak at about 186.0±4° C.; a DSC melting onset at about 183.5±4° C.; a TGA thermogram substantially as depicted in FIG. 45; and by combinations of these data. The theoretical content of 1,2-propanediol for a monosolvate of cabazitaxel is about 8.3% w/w.

Form XIX can be characterized by any combination of the above data.

Figure 46:
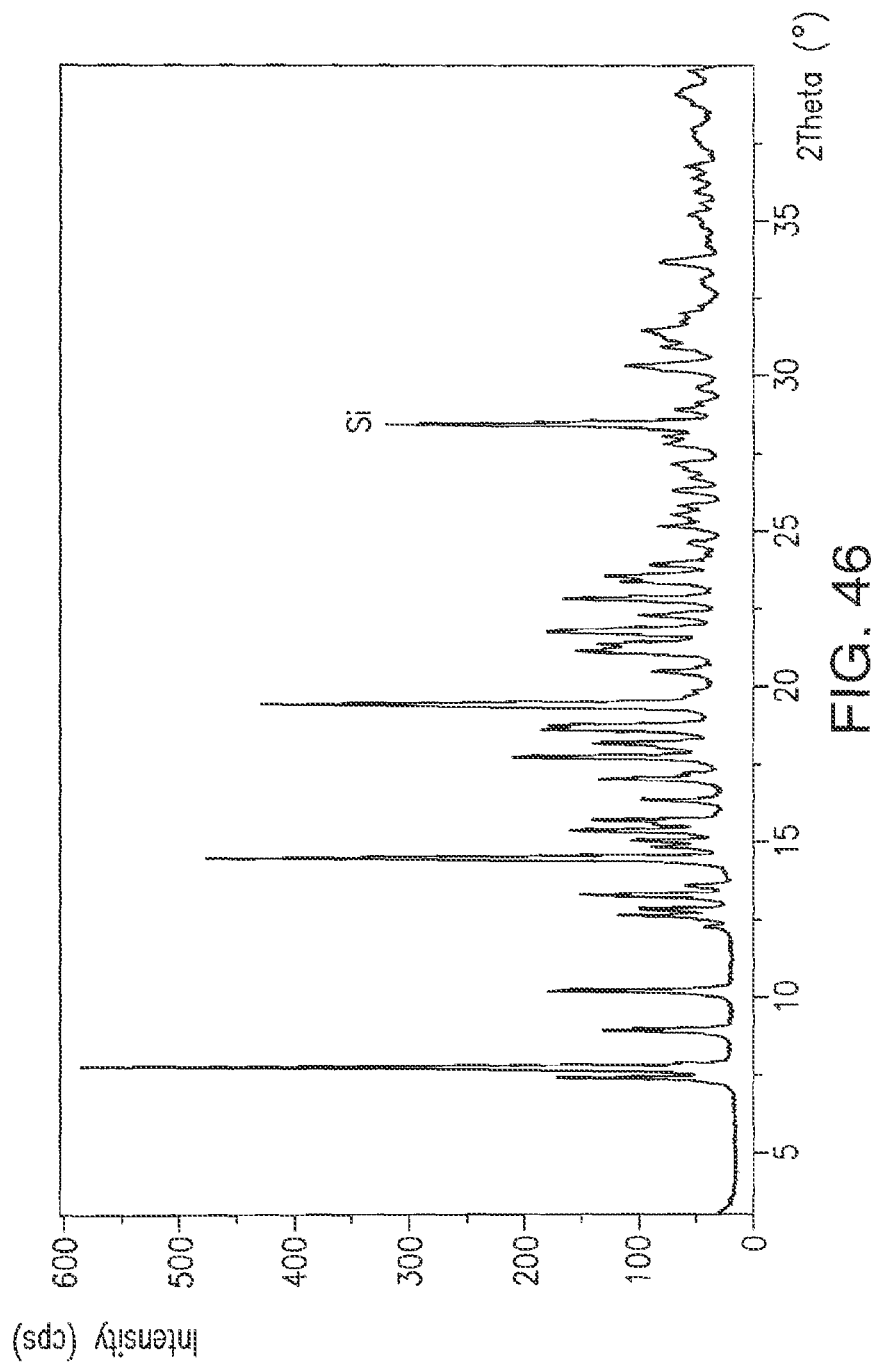
FIG. 46 shows a PXRD pattern for crystalline Cabazitaxel form XX.

The present invention also encompasses a glycerol formal solvate of cabazitaxel. Particularly, the present invention encompasses crystalline Cabazitaxel glycerol formal designated as Form XX. Form XX can be characterized by data selected from one or more of the following: a powder X-ray diffraction pattern having peaks at 8.9, 13.3, 14.5, 16.3 and 18.1 degrees two theta±0.1 degrees two theta; by a powder X-ray diffraction pattern substantially as depicted in FIG. 46, and by a combination of these data.

Form XX, characterized by a powder X-ray diffraction pattern having peaks at 8.9, 13.3, 14.5, 16.3 and 18.1 degrees two theta±0.1 degrees two theta, can be further characterized by a powder X-ray diffraction pattern having no peak in the area from 10.5 to 12.1 degrees two theta.

Form XX, characterized by a powder X-ray diffraction pattern having peaks at 8.9, 13.3, 14.5, 16.3 and 18.1 degrees two theta±0.1 degrees two theta, can be further characterized by an additional one, two, three, four or five PXRD peaks selected from 7.4, 7.8, 10.2, 12.2 and 19.4 degrees two theta±0.1 degrees two theta.

Figure 47:
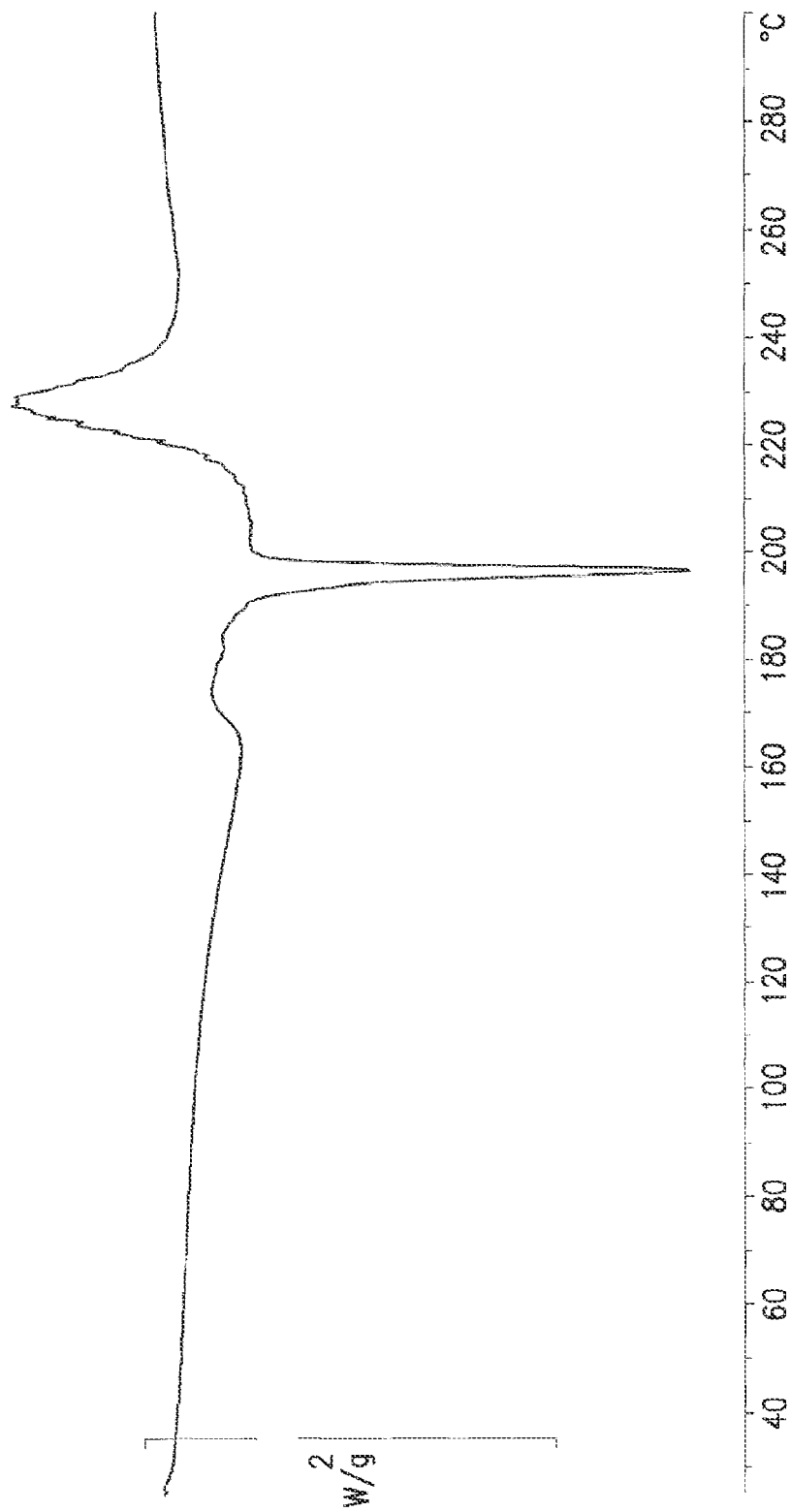
FIG. 47 shows a DSC thermogram for crystalline Cabazitaxel form XX.
Figure 48:
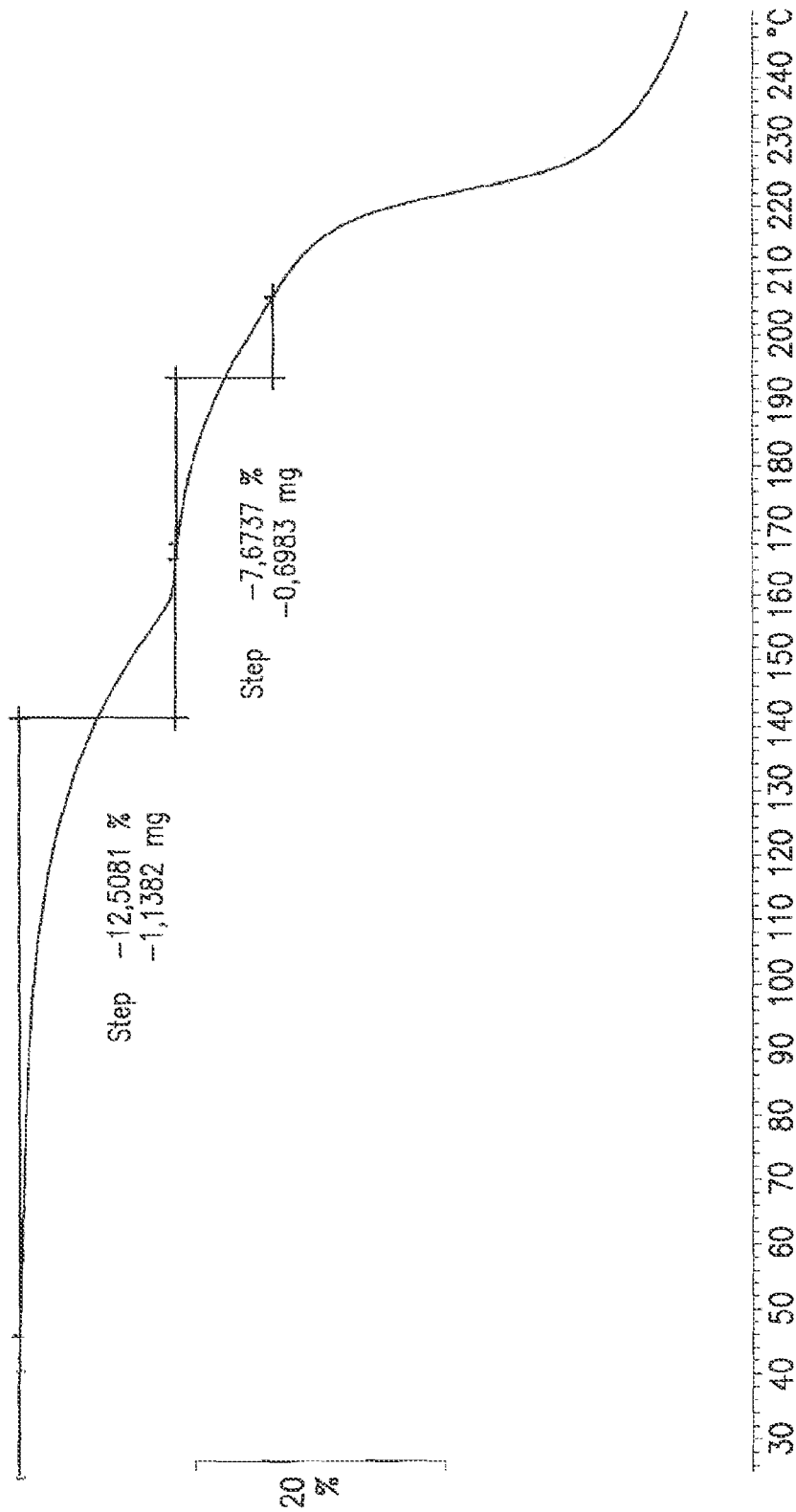
FIG. 48 shows a TGA thermogram for crystalline Cabazitaxel form XX.

Form XX can be further characterized by data selected from one or more of the following: a DSC thermogram substantially as depicted in FIG. 47; a DSC melting peak at about 196.2±4° C.; a DSC melting onset at about 193.7±4° C.; a TGA thermogram substantially as depicted in FIG. 48; and by combinations of these data. The theoretical content of glycerol formal for a monosolvate of cabazitaxel is about 11.1% w/w.

Form XX can be characterized by any combination of the above data.

Figure 49:
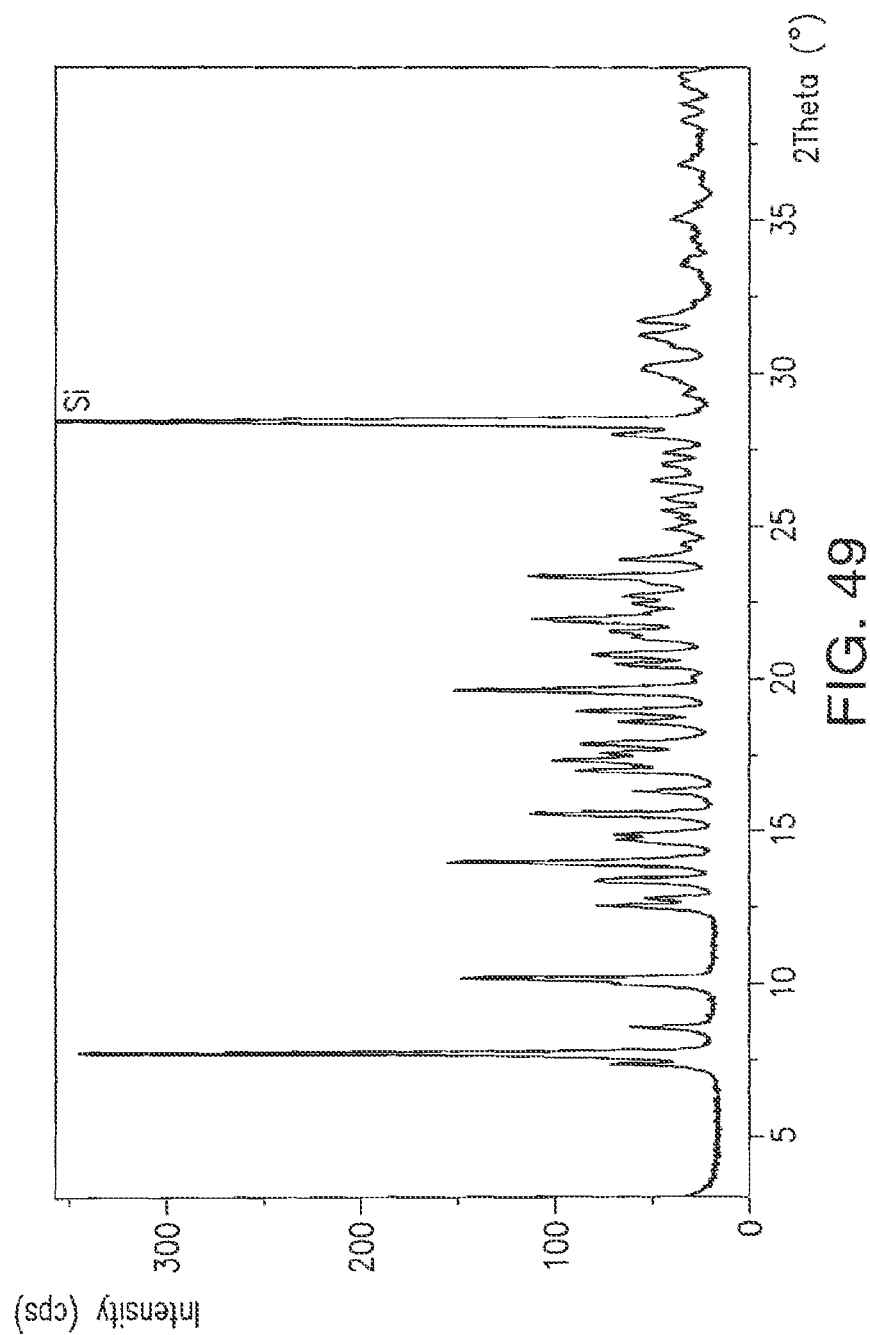
FIG. 49 shows a PXRD pattern for crystalline Cabazitaxel form XXI.

The present invention also encompasses an isobutyl acetate solvate of cabazitaxel. Particularly, the present invention encompasses crystalline Cabazitaxel isobutyl acetate designated as Form XXI. Form XXI can be characterized by data selected from one or more of the following: a powder X-ray diffraction pattern having peaks at 8.6, 14.0, 15.6, 16.3 and 19.6 degrees two theta±0.1 degrees two theta; by a powder X-ray diffraction pattern substantially as depicted in FIG. 49, and by a combination of these data.

Form XXI, characterized by a powder X-ray diffraction pattern having peaks at 8.6, 14.0, 15.6, 16.3 and 19.6 degrees two theta±0.1 degrees two theta, can be further characterized by a powder X-ray diffraction pattern having no peak in the area from 10.5 to 12.1 degrees two theta.

Form XXI, characterized by a powder X-ray diffraction pattern having peaks at 8.6, 14.0, 15.6, 16.3 and 19.6 degrees two theta±0.1 degrees two theta, can be further characterized by an additional one, two, three, four or five PXRD peaks selected from 7.4, 7.8, 10.2, 12.6 and 13.4 degrees two theta±0.1 degrees two theta.

Figure 50:
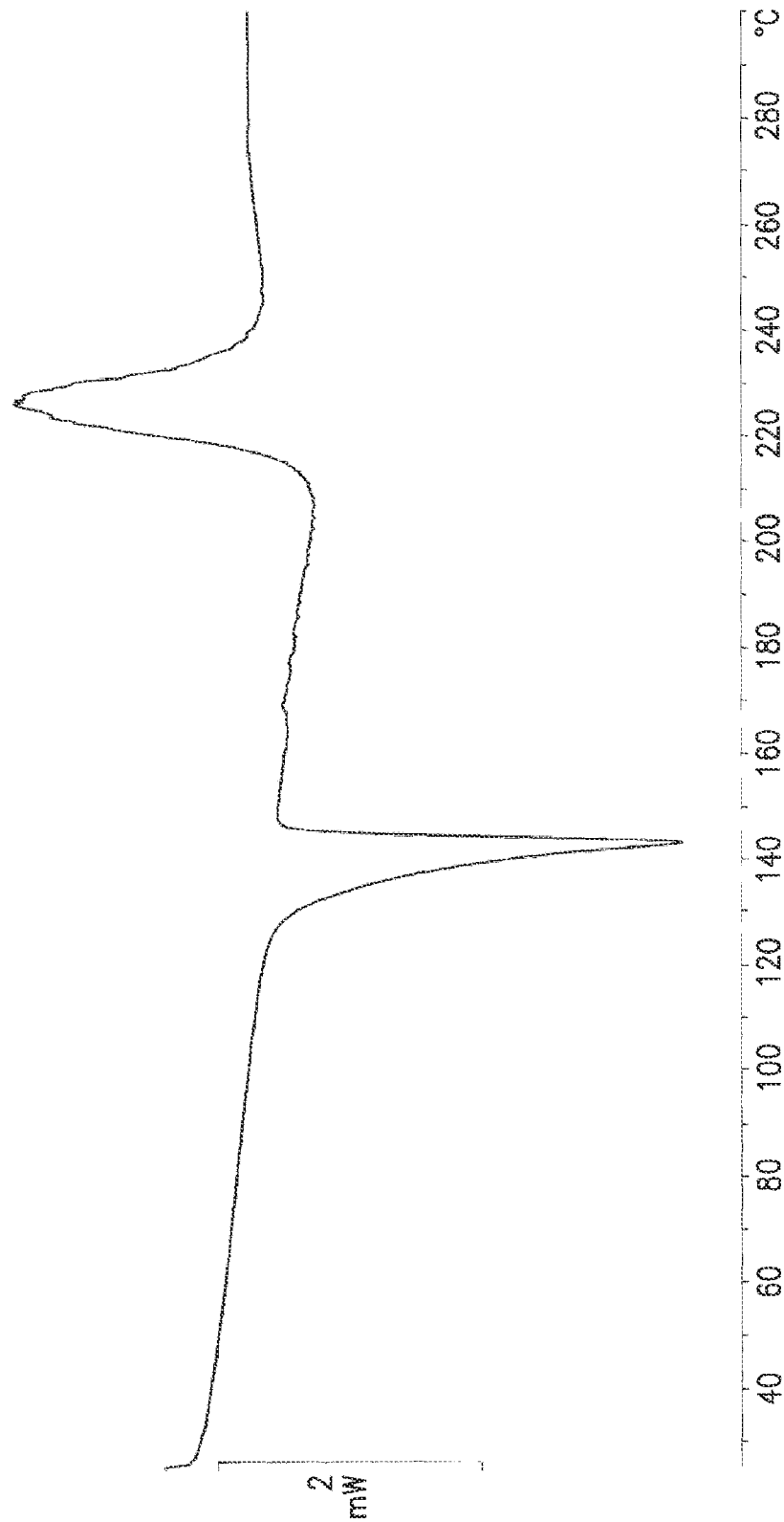
FIG. 50 shows a DSC thermogram for crystalline Cabazitaxel form XXI.
Figure 51:
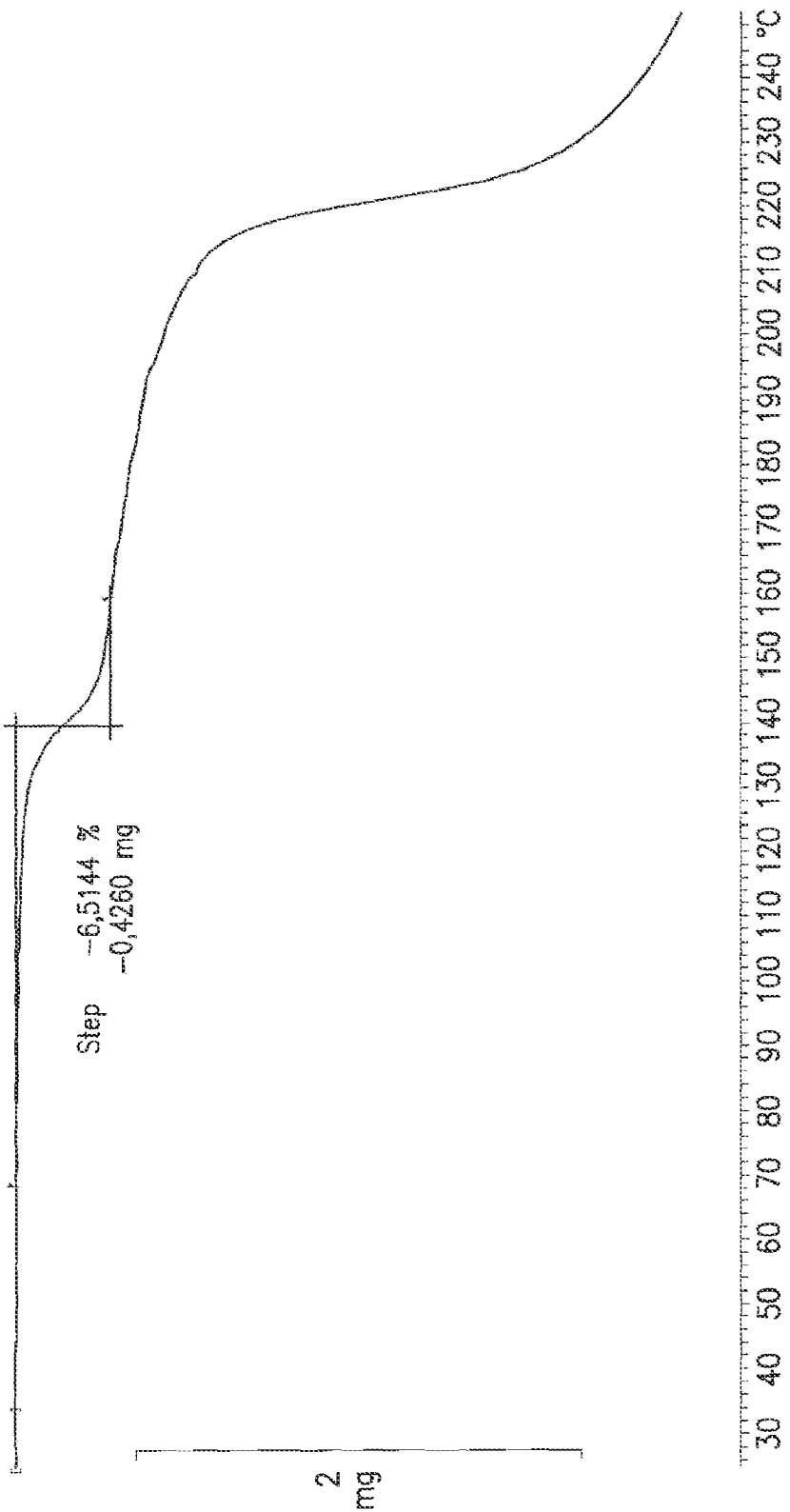
FIG. 51 shows a TGA thermogram for crystalline Cabazitaxel form XXI.

Form XXI can be further characterized by data selected from one or more of the following: a DSC thermogram substantially as depicted in FIG. 50; a DSC melting peak at about 142.8±4° C.; a DSC melting onset at about 136.9±4° C.; a TGA thermogram substantially as depicted in FIG. 51; and by combinations of these data. The theoretical content of isobutyl acetate for a monosolvate of cabazitaxel is about 12.2% w/w. For example, the content of the isobutyl acetate can be about 6.5%±2 w/w as determined by TGA.

Form XXI can be characterized by any combination of the above data.

Figure 52:
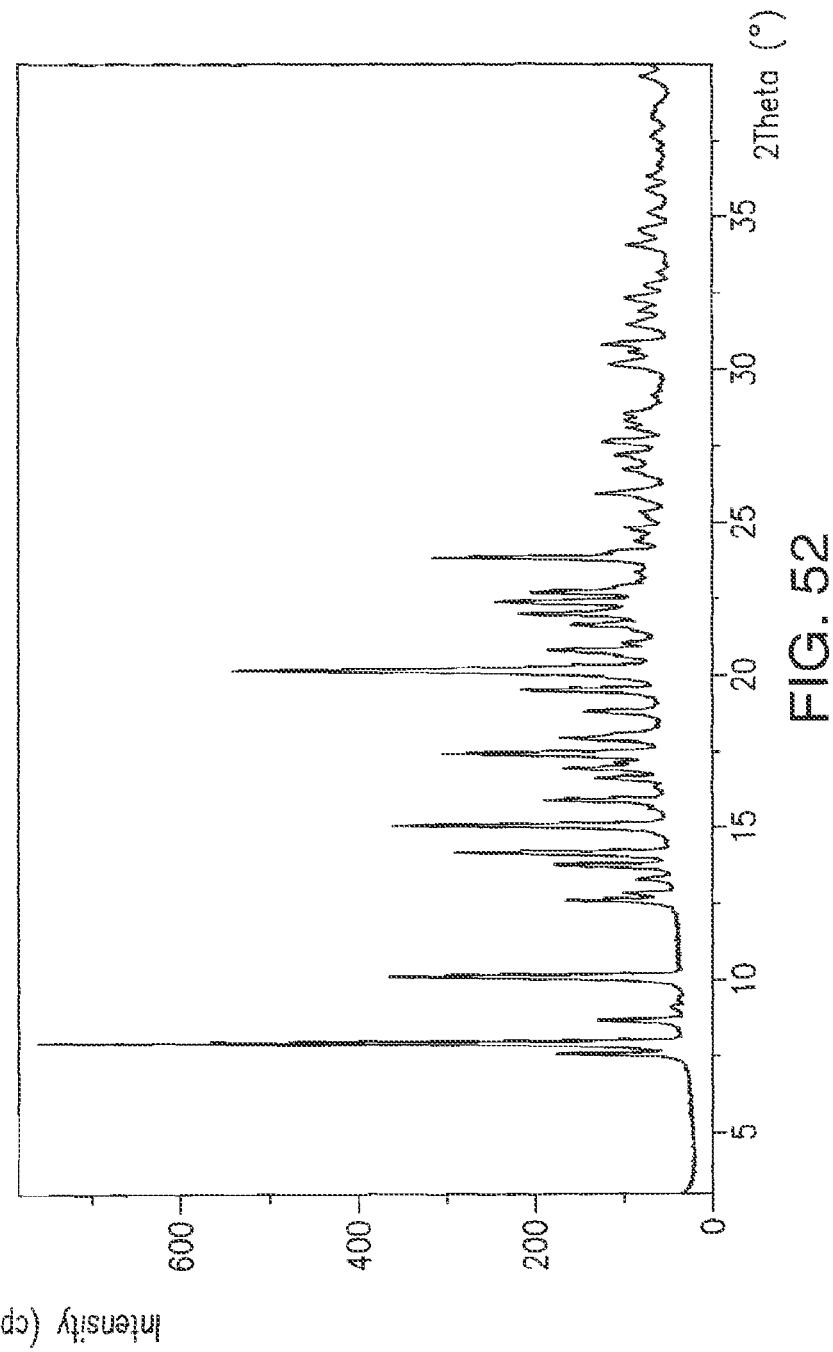
FIG. 52 shows a PXRD pattern for crystalline Cabazitaxel form XXII.

The present invention also encompasses an DMI (1,3-Dimethyl-2-imidazolidinone) solvate of cabazitaxel. Particularly, the present invention encompasses crystalline Cabazitaxel DMI (1,3-Dimethyl-2-imidazolidinone) solvate designated as Form XXII. Form XXII can be characterized by data selected from one or more of the following: a powder X-ray diffraction pattern having peaks at 7.6, 8.0, 8.7, 10.1, 12.6, 12.8, 14.2, 15.1, 15.9, 17.4 and 20.1 degrees two theta±0.1 degrees two theta; by a powder X-ray diffraction pattern substantially as depicted in FIG. 52, and by a combination of these data.

Figure 53:
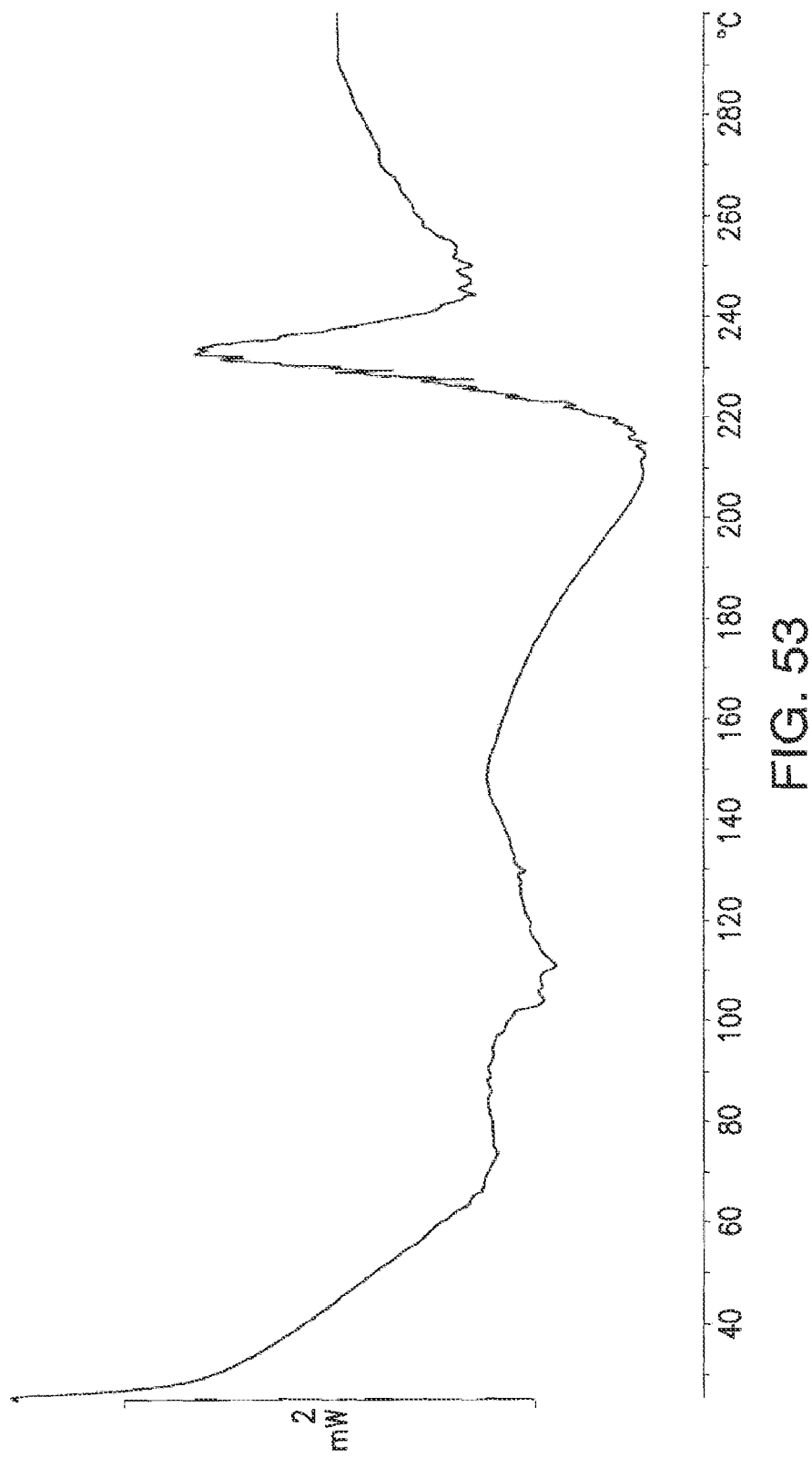
FIG. 53 shows a DSC thermogram for crystalline Cabazitaxel form XXII.
Figure 54:
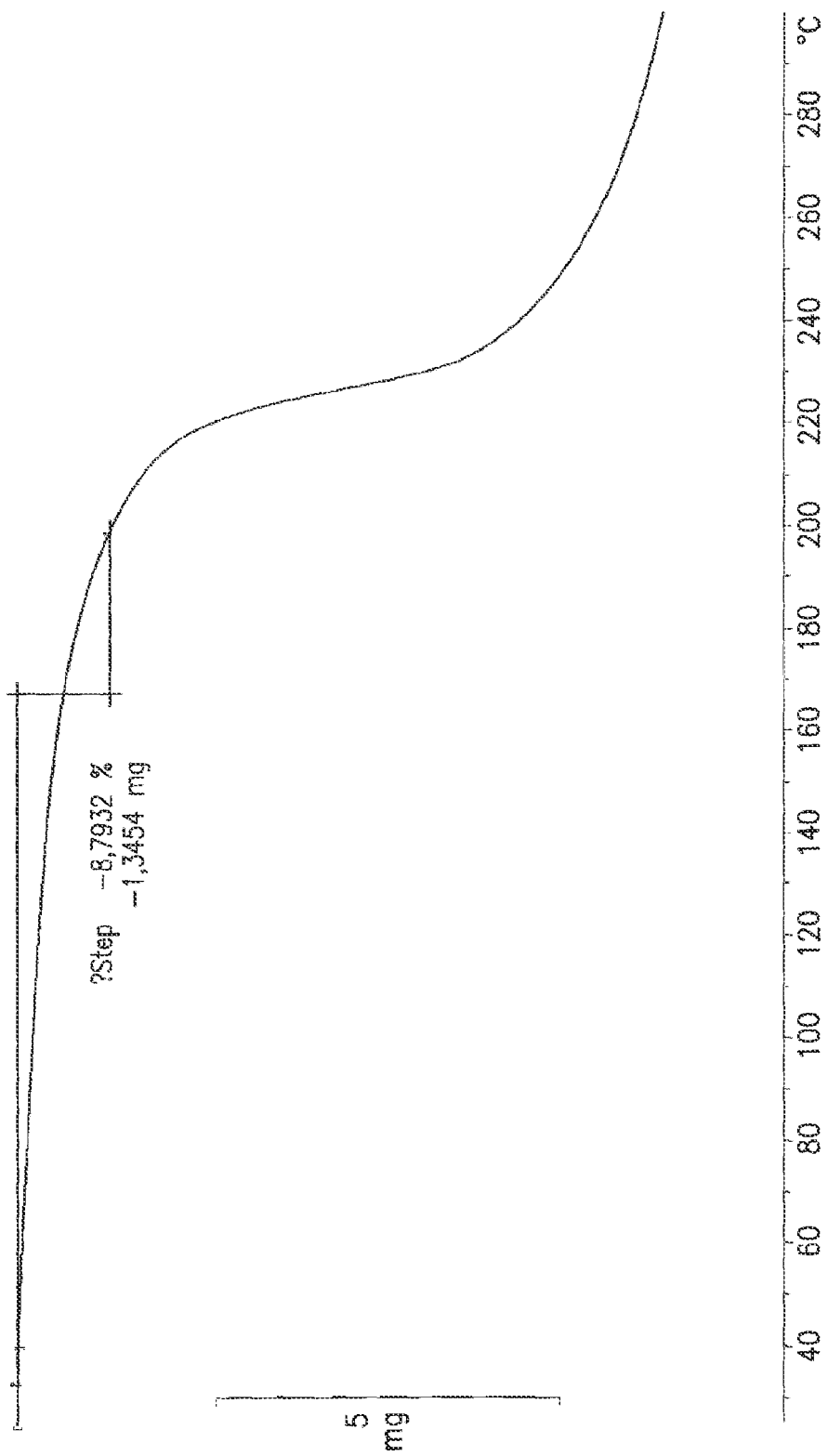
FIG. 54 shows a TGA thermogram for crystalline Cabazitaxel form XXII.

Form XXII can be further characterized by data selected from one or more of the following: a DSC thermogram substantially as depicted in FIG. 53; a TGA thermogram substantially as depicted in FIG. 54; and by combinations of these data. The theoretical content of DMI (1,3-Dimethyl-2-imidazolidinone) for a monosolvate of cabazitaxel is about 12.0% w/w. For example, the content of the DMI (1,3-Dimethyl-2-imidazolidinone) can be about 8.8%±2 w/w as determined by TGA.

Form XXII can be characterized by any combination of the above data.

The above solid state forms can be used to prepare pharmaceutical compositions and pharmaceutical formulations.

The present invention hence further encompasses 1) a pharmaceutical composition comprising one or more of the solid state forms described herein; 2) a pharmaceutical formulation comprising one or more of the solid state forms described herein, and at least one pharmaceutically acceptable excipient; 3) a process to prepare such formulations comprising combining the above-described solid state forms and at least one pharmaceutically acceptable excipient; 4) the use of one or more of the above-described solid state forms, in the manufacture of a pharmaceutical composition, and 4) a method of treating prostate cancer, e.g., hormone refractory prostate cancer comprising administering a therapeutically effective amount of one or more of the solid state forms described herein, optionally in the form of a pharmaceutical composition or formulation. The pharmaceutical composition can be used for preparing a medicament. The present invention also provides crystalline forms as described above for use as a medicament. The present invention also encompasses a formulation comprising a pharmaceutical composition according to the invention.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Powder X-Ray Diffraction (PXRD) Method

Powder X-ray Diffraction was performed on an X-Ray powder diffractometer: PanAlytical X'pert Pro; CuKα radiation ($\lambda$=1.5418 Å); X'Celerator detector with active length 2.122 degrees 2-theta; laboratory temperature 22-25° C.; zero background sample holders. Prior to analysis, the samples were gently ground using a mortar and pestle to obtain a fine powder. The ground sample was adjusted into a cavity of the sample holder and the surface of the sample was smoothed using a cover glass.

A silicon powder internal standard was used to calibrate the peak positions and to eliminate an effect of the sample preparation. The internal standard possesses a diffraction pattern with defined position at 28.44 degrees 2-theta. The internal standard powder can be mixed with a sample The PXRD diffractogram is then acquired and the current position of the aforementioned internal standard diffraction peak is determined. The difference between the current position of the diffraction and its nominal value of 28.44 degrees 2-theta is calculated. The current positions of all relevant sample peaks are then corrected using the above difference to obtain the true positions of the sample diffractions. The confidence interval for the peak positions was determined to be ±0.1 degrees 2-theta.

Measurement Parameters:
Scan range: 3-40 degrees 2-theta;
Scan mode: continuous;
Step size: 0.0167 degrees;
Time per step: 42 s;
Sample spin: 16 rpm;
Sample holder: zero background silicon plate.

Differential Scanning Calorimetry (DSC) Method

DSC measurements were performed on a Differential Scanning calorimeter DSC823e (Mettler Toledo). Aluminum crucibles 40 µl with pin-holed lids were used for sample preparation. Typical sample weight was between 1 and 5 mg. Program parameters: temperature range at least 30-250° C.; heating rate 10° C./min; nitrogen flow 50 ml/min.

Thermogravimetric Analysis (TGA) Method

TGA measurements were performed on a Thermogravimetric analyzer TGA851e (Mettler Toledo). Alumina crucibles 70 µl were used for sample preparation. Usual weight of sample was between 7 and 13 mg.
Program parameters: temperature range at least 30-250° C.; heating rate 10° C./min; nitrogen flow 50° C./min.

Gas Chromatography (GC) Method

Residual solvents were determined by gas chromatography using head-space sampling. Head-space instrument HP7694 coupled with gas chromatograph A6890 equipped with FID detector (Agilent technologies) were used for the analyses.

$^{13}$C Solid-State NMR

Solid-state $^{13}$C NMR spectra were recorded with variable amplitude cross polarization, magic angle spinning and high power proton decoupling using a BRUKER Avance II+ spectrometer operating at 125 MHz and ambient temperature (about 25° C. —not controlled). A probe using 4 mm o.d. zirconia rotors was employed. The operation conditions were: contact time: 2 ms; acquisition time, recycle delay: 2 s, 2048 scans; spin rate: 11 kHz. Chemical shifts were referenced via a replacement sample of glycine (carboxyl carbon chemical shift assigned as 176.03 ppm relative to the signal of tetramethylsilane).

Single Crystal Analysis

Data was collected on Xcalibur PX, Cu K$_\alpha$ using combined φ and ω scans, data collection runs were optimized for absolute configuration analysis. Positional and anisotropical thermal parameters of all non-hydrogen atoms were refined.

Hygroscopicity Test Procedure:

About 150 mg of a sample was placed to a cell with controlled relative humidity. The samples were exposed to 60%, 80% and 100% relative humidity for a period of two days. XRPD analysis and water content by coulometric Karl-Fischer titration were carried out before and after the exposure to the defined relative humidity.

Coulometric Karl-Fischer Titration:

Water was determined by KF Oven method (832 KF Thermoprep connected to 831 KF Coulometer). Water from the sample (50 mg of cabazitaxel) was released by nitrogen stream at 130° C. Extraction time was 10 minutes.

EXAMPLES

Example 1

General Procedure for the Preparation of Crude Cabazitaxel

A solution of lithium bis(trimethylsilyl)amide (LHMDS, 23% in THF, 8.73 g, 12 mmol) was added to a stirred suspension of 7,10-dimethoxy-10-DAB (5.73 g, 10 mmol) and N-Boc-O-EE-beta-lactam (4.02 g, 12 mmol) in dry THF (30 ml) at room temperature over 20 min. When the reaction was complete (about 3 h), formic acid (20 ml) was added and the resulting mixture was stirred for 20 h. The reaction mixture was then partitioned between methyl-tert-butyl ether (MTBE) (80 ml) and water (100 ml). The separated organic phase was extracted with water (2×50 ml), separated, and concentrated to provide a syrup.

Example 2

Preparation of Cabazitaxel Form III

Cabazitaxel (toluene solvate form I prepared as described in example 20, 1.2 g) was dissolved in isopropanol ("i-PrOH") (20 ml) at reflux, and the solution was then allowed to cool. The product started to precipitate at 35-40° C. The mixture was cooled to 22° C. and was maintained for 20 h. The product was then separated by filtering, washed with i-PrOH and dried on filter.

Solid State NMR Peaks:
173.51, 171.14, 166.09, 155.63, 139.84, 138.27, 135.20, 133.59, 129.31, 127.84, 125.08, 85.68, 83.52, 82.53, 82.11, 79.53, 79.06, 75.99, 73.79, 73.5, 70.18, 63.39, 57.80, 57.19, 56.4, 53.72, 48.83, 42.92, 34.30, 29.13, 28.57, 27.93, 25.44, 23.53, 22.12, 20.23, 15.44 and 11.54 ppm±0.2 ppm.

Example 3

Preparation of Cabazitaxel Form V

Cabazitaxel (form I prepared as described in WO2012142117, toluene solvate, 1 g) was dissolved in 1-propanol (15 ml) at reflux and the solution was allowed to cool to room temperature. The product started to precipitate after 2 hrs of stirring at 22° C. The mixture was stirred for 3 more hours at 22° C. The product was then separated by filtering, washed with 1-propanol and dried on the filter.

Example 4

Preparation of Cabazitaxel Form VII

Cabazitaxel form III (80 mg) (isopropanol solvate) was suspended in 0.5 ml of ethyl acetate, heated up to 75° C. during 60 min, stirred at 75° C. for additional 30 min and then cooled down to (−5)° C. The suspension was stirred for an additional 2 hours. The solid matter was filtered off and dried in nitrogen stream at about room temperature.

Example 5

Preparation of Cabazitaxel Form VIII

Cabazitaxel form III (80 mg) (isopropanol solvate) was suspended in 0.5 ml of isopropyl acetate, heated up to 75° C. during 60 min, stirred at 75° C. for additional 30 min and then cooled down to (−5)° C. The suspension was stirred for an additional 2 hours. The solid matter was filtered off and dried in nitrogen stream at about room temperature.

Example 6

Preparation of Cabazitaxel Form IX

Cabazitaxel form III (80 mg, isopropanol solvate) was suspended in 0.5 ml of methyl ethyl ketone, heated up to 75°

C. during 60 min, stirred at 75° C. for additional 30 min and then cooled down to (−5)° C. The suspension was stirred for an additional 2 hours. The solid matter was filtered off and dried in nitrogen stream at about room temperature.

Example 7

Preparation of Cabazitaxel Form X 80 mg Cabazitaxel form III (80 mg, isopropanol solvate) was suspended in 0.5 ml of methyl isobutyl ketone, heated up to 75° C. during 60 min, stirred at 75° C. for additional 30 min and then cooled down to (−5)° C. The suspension was stirred for an additional 2 hours. The solid matter was filtered off and dried in nitrogen stream at about room temperature.

Example 8

Preparation of Cabazitaxel Form XI

Cabazitaxel form III (80 mg, isopropanol solvate) was suspended in 0.5 ml of 2-butanol, heated up to 95° C. during 60 min, stirred at 75° C. for additional 30 min and then cooled down to (−5)° C. The suspension was stirred for an additional 2 hours. The solid matter was filtered off and dried in nitrogen stream at about room temperature.

Example 9

Preparation of Cabazitaxel Form XII

Cabazitaxel form III (80 mg, isopropanol solvate) was suspended in 0.5 ml of isobutanol, heated up to 95° C. during 60 min, stirred at 75° C. for additional 30 min and then cooled down to (−5)° C. The suspension was stirred for an additional 2 hours. The solid matter was filtered off and dried in nitrogen stream at about room temperature.

Example 10

Preparation of Cabazitaxel Form XIII

Cabazitaxel form III (80 mg, isopropanol solvate) was suspended in 0.5 ml of 1-pentanol, heated up to 95° C. during 60 min, stirred at 75° C. for additional 30 min and then cooled down to (−5)° C. The suspension was stirred for an additional 2 hours. The solid matter was filtered off and dried in nitrogen stream at about room temperature.

Example 11

Preparation of Cabazitaxel Form XIV

Cabazitaxel (450 mg, isopropanol solvate form III) was dissolved in dioxolane (1.5 ml) and the solution was added slowly to vigorously stirred n-heptane 60 ml at 20° C. The suspension was stirred for additional 10 min and the solid matter was recovered by filtration, then washed with petroleum ether (10 ml) and dried in a nitrogen stream.

Example 12

Preparation of Cabazitaxel Form XV

Cabazitaxel (230 mg, isopropanol solvate form III) was dissolved in dioxane (5 ml) by heating for 5 min to 50° C. and n-heptane (8 ml) was added with stirring. The resulting clear solution was allowed to cool spontaneously and then crystallized at 15° C. for 24 hours. Well developed white crystals were recovered by filtration, washed with petroleum ether (10 ml) and dried on air.

Example 13

Preparation of Cabazitaxel Form XVI

Cabazitaxel (600 mg, form III IPA solvate) was dissolved in ethanol (10 ml), polysorbate was added (10 ml, Tween 20) and water (20 ml) was added to this mixture with stirring providing thus viscous solution. The solution was allowed to stand 1 week at 20° C., but crystallization was not observed. Additional amount of water (20 ml) was then added with stirring and the solution was allowed to stand again for 1 week. Additional portion of water (30 ml) was added with stirring and solution was allowed to stand again. After 1 week, few white crystals were observed at the bottom of flask and within about 3 days the amount of crystals grew exponentially. The crystals were recovered by filtration, washed 10 times with about 50 ml of water and dried in an air stream for 2 h. Yield 421 mg.

Example 14

Preparation of Cabazitaxel Form XVII

Cabazitaxel form III (80 mg, isopropanol solvate) was suspended in 0.5 ml of methyl acetate. The suspension was heated to 95° C. over 60 min, and then stirred at 75° C. for an additional 30 min, and then cooled to (−5)° C. The cooled suspension was stirred for an additional 2 hours. The solid matter which precipitated was filtered off and dried in a nitrogen stream at about room temperature.

Example 15

Preparation of Cabazitaxel Form XVIII

Cabazitaxel form III (80 mg, isopropanol solvate) was suspended in 0.5 ml of butyl acetate. The suspension was heated to 95° C. during 60 min, and then stirred at 75° C. for an additional 30 min, and then cooled to (−5)° C. The cooled suspension was stirred for an additional 2 hours. The solid matter that precipitated was filtered off and dried in a nitrogen stream at about room temperature.

Example 16

Preparation of Cabazitaxel Form XIX

Cabazitaxel form III (80 mg, isopropanol solvate) was suspended in 0.5 ml of 1,2-propanediol. The suspension was heated to 95° C. over 60 min, then stirred at 75° C. for an additional 30 min, and then cooled to (−5)° C. The cooled suspension was stirred for an additional 2 hours. The solid matter that precipitated was filtered off and dried in a nitrogen stream at about room temperature.

Example 17

Preparation of Cabazitaxel Form XX

Cabazitaxel form III (80 mg, isopropanol solvate) was suspended in 0.5 ml of glycerol formal. The suspension was heated to 95° C. over 60 min, then stirred at 75° C. for an additional 30 min, and then cooled to (−5)° C. The cooled suspension was stirred for an additional 2 hours. The solid matter that precipitated was filtered off and dried in nitrogen stream at about room temperature.

Example 18

Preparation of Cabazitaxel Form XXI

Cabazitaxel form III (80 mg, isopropanol solvate) was suspended in 0.5 ml of isobutyl acetate. The suspension was heated to 95° C. over 60 min, then stirred at 75° C. for an additional 30 min, and then cooled to (−5)° C. The cooled suspension was then stirred for an additional 2 hours. The solid matter that precipitated was filtered off and dried in a nitrogen stream at about room temperature.

Example 19

Preparation of Cabazitaxel Form XXII

Cabazitaxel (2 g isopropanol solvate form III) was suspended in 5 ml of DMI (1,3-dimethyl-2-imidazolidinone). The solid dissolved at room temperature. It was stirred in a 100 ml glass reactor (magnetic stirring) at 20° C. for 10 min. Then 10 ml of water was added. A white precipitate appeared. The suspension was stirred with water for 15 min, then it was filtered off and dried for 2 hours in a drier at 50° C. under $N_2$. Rubber-like material was obtained.

Example 20

Preparation of Cabazitaxel Form I

Cabazitaxel (8 g, prepared as described in example 1) was dissolved in a mixture containing 10% MTBE in toluene (150 ml) and slowly concentrated under slightly reduced pressure at 45-50° C. When the product started to precipitate, the vacuum was disconnected, and the mixture was stirred at 45-50° C. for 1 h, then cooled to 22° C., and stirred for 3 h and then filtered. The collected product was washed twice with toluene and dried on the filter.

Solid State NMR Peaks:
173.50, 171.23, 166.98, 156.23, 140.08, 139.25, 138.67, 136.35, 135.31, 131.05, 130.18, 129.37, 126.17, 85.63, 84.38, 82.95, 82.10, 80.73, 75.98, 74.82, 71.79, 59.05, 57.37, 55.38, 50.16, 44.21, 35.51, 30.86, 28.72, 22.85, 21.42, 16.47, and 12.58 ppm±0.2 ppm.

What is claimed is:

1. A crystalline Cabazitaxel alkyl acetate solvate selected from:
a) Crystalline Cabazitaxel ethyl acetate solvate, designated as Form VII, characterized by data selected from one or more of the following: a powder X-ray diffraction pattern having peaks at 7.9, 8.6, 10.0, 10.2 and 15.8 degrees two theta±0.1 degrees two theta, and also having no peak in the area from 10.5 to 12.1 degrees two theta; a powder X-ray diffraction pattern as depicted in FIG. 1; or combinations of these data;
b) Crystalline isopropyl acetate solvate of cabazitaxel, designated as Form VIII, characterized by data selected from one or more of the following: a powder X-ray diffraction pattern having peaks at 7.9, 8.6, 10.0, 10.2 and 16.6 degrees two theta±0.1 degrees two theta, and also having no peak in the area from 10.5 to 12.1 degrees two theta; a powder X-ray diffraction pattern as depicted in FIG. 4; or combination of these data;
c) Crystalline Cabazitaxel methyl acetate solvate, designated as Form XVII, characterized by data selected from one or more of the following: a powder X-ray diffraction pattern having peaks at 8.0, 8.7, 14.2, 15.1 and 15.9 degrees two theta±0.1 degrees two theta; a powder X-ray diffraction pattern as depicted in FIG. 37; or combination of these data;
d) Crystalline Cabazitaxel butyl acetate solvate, designated as Form XVIII, characterized by data selected from: a powder X-ray diffraction pattern having peaks at 8.6, 13.6, 14.0, 19.2 and 19.8 degrees two theta±0.1 degrees two theta; a powder X-ray diffraction pattern as depicted in FIG. 40; or a combination of these data; or
e) Crystalline Cabazitaxel isobutyl acetate, designated as Form XXI, characterized by data selected from one or more of the following: a powder X-ray diffraction pattern having peaks at 8.6, 14.0, 15.6, 16.3 and 19.6 degrees two theta±0.1 degrees two theta; a powder X-ray diffraction pattern as depicted in FIG. 49; or a combination of these data.

2. A crystalline Cabazitaxel ketone solvate selected from:
a) Crystalline Cabazitaxel methyl ethyl ketone ("MEK") solvate, designated as Form IX, characterized by data selected from one or more of the following: a powder X-ray diffraction pattern having peaks at 7.9, 8.8, 10.2, 13.5 and 19.8 degrees two theta±0.1 degrees two theta and also having no peak in the area from 10.5 to 12.1 degrees two theta; a powder X-ray diffraction pattern as depicted in FIG. 7; or a combination of these data; or
b) Crystalline Cabazitaxel methyl isobutyl ketone solvate, designated as Form X, characterized by data selected from one or more of the following: a powder X-ray diffraction pattern having peaks at 7.7, 8.7, 13.4, 14.2 and 15.6 degrees two theta±0.1 degrees two theta and also having no peak in the area from 10.5 to 12.1 degrees two theta; a powder X-ray diffraction pattern as depicted in FIG. 10; or a combination of these data.

3. A crystalline Cabazitaxel alcohol solvate selected from:
a) Crystalline Cabazitaxel 2-butanol solvate, designated as Form XI, characterized by data selected from one or more of the following: a powder X-ray diffraction pattern having peaks at 7.9, 10.2, 10.4, 12.6 and 16.5 degrees two theta±0.1 degrees two theta and also having no peak in the area from 10.5 to 12.1 degrees two theta; a powder X-ray diffraction pattern as depicted in FIG. 13; or a combination of these data;
b) crystalline Cabazitaxel isobutanol solvate, designated as Form XII, characterized by data selected from one or more of the following: a powder X-ray diffraction pattern having peaks at 7.8, 10.2, 13.3, 14.5 and 17.7 degrees two theta±0.1 degrees two theta and also having no peak in the area from 10.5 to 12.1 degrees two theta; a powder X-ray diffraction pattern as depicted in FIG. 16; or combinations of these data; or
c) crystalline Cabazitaxel amyl alcohol solvate, designated as Form XIII, characterized by data selected from one or more of the following: a powder X-ray diffraction pattern having peaks at 7.8, 10.1, 10.2, 13.4 and 14.4 degrees two theta±0.1 degrees two theta and also having no peak in the area from 10.5 to 12.1 degrees two theta; a powder X-ray diffraction pattern as depicted in FIG. 19; or a combination of these data.

4. The crystalline Form VII of claim 1, characterized by a powder X-ray diffraction pattern having peaks at 7.9, 8.6, 10.0, 10.2 and 15.8 degrees two theta±0.1 degrees two theta, and also having no peak in the area from 10.5 to 12.1 degrees two theta, and further characterized by an additional one, two, three, four or five PXRD peaks selected from 7.5, 13.8, 14.1, 15.0 or 18.0 degrees two theta±0.1 degrees two theta.

5. The crystalline Form VII of claim 1, further characterized by data selected from one or more of the following: a DSC thermogram as depicted in FIG. 2; a DSC melting peak at about 162.0±4° C. and DSC melting onset at about 157.2±4° C.; a TGA thermogram as depicted in FIG. 3; or combinations of these data.

6. The crystalline Form VIII of claim 1, characterized by a powder X-ray diffraction pattern having peaks at 7.9, 8.6, 10.0, 10.2 and 16.6 degrees two theta±0.1 degrees two theta, and also having no peak in the area from 10.5 to 12.1 degrees two theta, and further characterized by an additional one, two, three, four or five PXRD peaks selected from 7.5, 12.6, 14.0, 14.9 or 15.8 degrees two theta±0.1 degrees two theta.

7. The crystalline Form VIII of claim 1, further characterized by data selected from one or more of the following: a DSC thermogram as depicted in FIG. 5; DSC melting peak at about 159.1±4° C. and DSC melting onset at about 155.7±4° C.; a TGA thermogram as depicted in FIG. 6; or combinations of these data.

8. The crystalline Form IX of claim 2, characterized by a powder X-ray diffraction pattern having peaks at 7.9, 8.8, 10.2, 13.5 and 19.8 degrees two theta±0.1 degrees two theta and also having no peak in the area from 10.5 to 12.1 degrees two theta, and further characterized by data selected from: an additional one, two, three, four or five PXRD peaks selected from 7.5, 12.6, 12.9, 15.2 or 17.0 degrees two theta±0.1 degrees two theta.

9. The crystalline Form IX of claim 2, further characterized by data selected from one or more of the following: a DSC thermogram as depicted in FIG. 8; a DSC melting peak at about 162.1±4° C. and a DSC melting onset at about 154.6±4° C.; a TGA thermogram as depicted in FIG. 9; or combinations of these data.

10. The crystalline Form X of claim 2, characterized by a powder X-ray diffraction pattern having peaks at 7.7, 8.7, 13.4, 14.2 and 15.6 degrees two theta±0.1 degrees two theta and also having no peak in the area from 10.5 to 12.1 degrees two theta, and further characterized by an additional one, two, three, four or five PXRD peaks selected from 7.4, 10.2, 12.6, 12.8 or 18.9 degrees two theta±0.1 degrees two theta.

11. The crystalline Form X of claim 2, further characterized by data selected from one or more of the following: a DSC thermogram as depicted in FIG. 11; a DSC double peak having maxima at about 158.4±4° C. and 162.1±4° C. and a DSC melting onset at about 154.2±4° C.; a TGA thermogram as depicted in FIG. 12; or combinations of these data.

12. The crystalline Form XI of claim 3, characterized by a powder X-ray diffraction pattern having peaks at 7.9, 10.2, 10.4, 12.6 and 16.5 degrees two theta±0.1 degrees two theta and also having no peak in the area from 10.5 to 12.1 degrees two theta, and further characterized by an additional one, two, three, four or five PXRD peaks selected from 7.4, 9.0, 12.2, 13.3 or 14.5 degrees two theta±0.1 degrees two theta.

13. The crystalline Form XI of claim 3, further characterized by data selected from one or more of the following: a DSC thermogram as depicted in FIG. 14; a DSC double peak having maxima at about 170.1±4° C. and 179.6±4° C. and a DSC melting onset at about 160.4±4° C.; a TGA thermogram as depicted in FIG. 15; or combinations of these data.

14. The crystalline Form XII of claim 3, characterized by a powder X-ray diffraction pattern having peaks at 7.8, 10.2, 13.3, 14.5 and 17.7 degrees two theta±0.1 degrees two theta and also having no peak in the area from 10.5 to 12.1 degrees two theta, and further characterized by an additional one, two, three, four or five PXRD peaks selected from 7.4, 9.0, 12.2, 12.6 or 19.4 degrees two theta±0.1 degrees two theta.

15. The crystalline Form XII of claim 3, further characterized by data selected from one or more of the following: a DSC thermogram as depicted in FIG. 17; a DSC double peak having maxima at about 169.5±4° C. and 182.7±4° C. and a DSC melting onset at about 159.8±4° C.; a TGA thermogram as depicted in FIG. 18; or combinations of these data.

16. The crystalline Form XIII of claim 3, characterized by a powder X-ray diffraction pattern having peaks at 7.8, 10.1, 10.2, 13.4 and 14.4 degrees two theta±0.1 degrees two theta and also having no peak in the area from 10.5 to 12.1 degrees two theta, and further characterized by an additional one, two, three, four or five PXRD peaks selected from 7.4, 8.7, 12.6, 15.6 or 19.7 degrees two theta±0.1) degrees two theta.

17. The crystalline Form XIII of claim 3, further characterized by additional data selected from one or more of the following: a DSC thermogram as depicted in FIG. 20; a DSC double peak having maxima at about 154.8±4° C. and 164.7±4° C. and a DSC melting onset at about 147.3±4° C.; a TGA thermogram as depicted in FIG. 21; or combinations of these data.

18. The crystalline Form XVII of claim 1, characterized by a powder X-ray diffraction pattern having peaks at 8.0, 8.7, 14.2, 15.1 and 15.9 degrees two theta±0.1 degrees two theta, and further characterized by an additional one, two, three, four or five PXRD peaks selected from 7.5, 10.1, 12.6, 12.9 or 20.1 degrees two theta±0.1 degrees two theta.

19. The crystalline Form XVII of claim 1, further characterized by data selected from one or more of the following: a DSC thermogram as depicted in FIG. 38; a DSC melting double peak at about 154.9±4° C. and 163.1±4° C.; a DSC melting onset at about 143.2±4° C.; a TGA thermogram as depicted in FIG. 39; or combinations of these data.

20. The crystalline Form XVIII of claim 1, characterized by a powder X-ray diffraction pattern having peaks at 8.6, 13.6, 14.0, 19.2 and 19.8 degrees two theta±0.1 degrees two theta, and further characterized by an additional one, two, three, four or five PXRD peaks selected from 7.5, 7.8, 10.2, 14.9 or 15.7 degrees two theta±0.1 degrees two theta.

21. The crystalline Form XVIII of claim 1, further characterized by data selected from one or more of the following: a DSC thermogram as depicted in FIG. 41; a DSC melting peak at about 136.6±4° C.; a DSC melting onset at about 130.1±4° C.; a TGA thermogram as depicted in FIG. 42; or combinations of these data.

22. The crystalline Form XXI of claim 1, characterized by a powder X-ray diffraction pattern having peaks at 8.6, 14.0, 15.6, 16.3 and 19.6 degrees two theta±0.1 degrees two theta, and further characterized by an additional one, two, three, four or five PXRD peaks selected from 7.4, 7.8, 10.2, 12.6 or 13.4 degrees two theta±0.1 degrees two theta.

23. The crystalline Form XXI of claim 1, further characterized by data selected from one or more of the following: a DSC thermogram as depicted in FIG. 50; a DSC melting peak at about 142.8±4° C.; a DSC melting onset at about 136.9±4° C.; a TGA thermogram as depicted in FIG. 51; or combinations of these data.

24. Crystalline Cabazitaxel designated as Form XVI, characterized by data selected from one or more of the following: a powder X-ray diffraction pattern having peaks at 4.0, 4.4, 9.3, 11.6 and 14.7 degrees two theta±0.1 degrees two theta; a powder X-ray diffraction pattern as depicted in FIG. 28; or a combination of these data.

25. The crystalline Form XVI of claim 24, characterized by a powder X-ray diffraction pattern having peaks at 4.0, 4.4, 9.3, 11.6 and 14.7 degrees two theta±0.1 degrees two theta, and further characterized by an additional one, two, three, four or five PXRD peaks selected from 7.5, 7.7, 12.6, 12.8 or 13.7 degrees two theta±0.1 degrees two theta.

26. The crystalline Form XVI of claim 24, further characterized by data selected from one or more of the following: a DSC thermogram as depicted in FIG. 29; a DSC melting peak at about 189.7±4° C. and a DSC melting onset at about 183.0±4° C.; a TGA thermogram as depicted in FIG. 30; or combinations of these data.

27. The crystalline Form XVI of claim 24, wherein said form is an anhydrous form.

28. A process for preparing cabazitaxel, or their solid state forms, comprising preparing any one of the crystalline form of cabazitaxel according to any one of claim 1, 2, 3, or 24, and converting said form to cabazitaxel, or their solid state forms.

29. A pharmaceutical composition comprising one or more crystalline cabazitaxel according to any one of claim 1, 2, 3, or 24.

30. A pharmaceutical formulation comprising one or more crystalline cabazitaxel forms according to any one of claim 1, 2, 3, or 24, and at least one pharmaceutically acceptable excipient.

31. A process for preparing a pharmaceutical formulation comprising combining one or more crystalline cabazitaxel forms according to any one of claim 1, 2, 3, or 24 and at least one pharmaceutically acceptable excipient.

32. A method of treating hormone-refractory prostate cancer in a person comprising administering a therapeutically effective amount of a crystalline cabazitaxel form according to any one of claim 1, 2, 3, or 24.

33. A method of treating hormone-refractory prostate cancer in a person comprising administering a therapeutically effective amount of a pharmaceutical composition according to claim 29.

* * * * *